US010000442B2

(12) United States Patent
Narine et al.

(10) Patent No.: US 10,000,442 B2
(45) Date of Patent: *Jun. 19, 2018

(54) CERTAIN METATHESIZED NATURAL OIL TRIACYLGLYCEROL POLYOLS FOR USE IN POLYURETHANE APPLICATIONS AND THEIR RELATED PROPERTIES

(71) Applicant: Trent University, Peterborough (CA)

(72) Inventors: Suresh Narine, Peterborough (CA); Prasanth Kumar Sasidharan Pillai, Peterborough (CA); Shaojun Li, Peterborough (CA); Laziz Bouzidi, Peterborough (CA); Ali Mahdevari, Peterborough (CA)

(73) Assignee: Trent University, Peterborough, Ontario (CA)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/670,125

(22) Filed: Mar. 26, 2015

(65) Prior Publication Data
US 2015/0299099 A1   Oct. 22, 2015

Related U.S. Application Data

(60) Provisional application No. 62/107,404, filed on Jan. 24, 2015, provisional application No. 61/971,475, filed on Mar. 27, 2014.

(51) Int. Cl.
| | |
|---|---|
| *C08G 18/36* | (2006.01) |
| *C07C 69/675* | (2006.01) |
| *C07C 69/34* | (2006.01) |
| *C11C 3/00* | (2006.01) |
| *C08J 9/00* | (2006.01) |
| *C08G 18/76* | (2006.01) |
| *C08G 18/32* | (2006.01) |
| *C08J 9/12* | (2006.01) |
| *C09D 175/04* | (2006.01) |
| *C08G 101/00* | (2006.01) |

(52) U.S. Cl.
CPC ........ *C07C 69/675* (2013.01); *C08G 18/3206* (2013.01); *C08G 18/36* (2013.01); *C08G 18/7664* (2013.01); *C08J 9/0014* (2013.01); *C08J 9/0042* (2013.01); *C08J 9/12* (2013.01); *C11C 3/00* (2013.01); *C08G 2101/0008* (2013.01); *C08G 2101/0025* (2013.01); *C08G 2101/0083* (2013.01); *C08J 2203/06* (2013.01); *C08J 2205/06* (2013.01); *C08J 2205/10* (2013.01); *C08J 2375/04* (2013.01); *C09D 175/04* (2013.01); *C11C 3/006* (2013.01)

(58) Field of Classification Search
CPC ............ C08G 18/36; C11C 3/006; B01J 2231/54–2231/543; B01J 2231/70–2231/72; C07C 69/675
See application file for complete search history.

(56) References Cited

U.S. PATENT DOCUMENTS

| | | | |
|---|---|---|---|
| 4,545,941 A | 10/1985 | Rosenburg | |
| 4,997,858 A * | 3/1991 | Jourquin | C08J 9/142 521/118 |
| 5,312,940 A | 5/1994 | Grubbs et al. | |
| 5,342,909 A | 8/1994 | Grubbs et al. | |
| 5,710,298 A | 1/1998 | Grubbs et al. | |
| 5,728,785 A | 3/1998 | Grubbs et al. | |
| 5,728,917 A | 3/1998 | Grubbs et al. | |
| 5,750,815 A | 5/1998 | Grubbs et al. | |
| 5,831,108 A | 11/1998 | Grubbs et al. | |
| 5,922,863 A | 7/1999 | Grubbs et al. | |
| 6,306,988 B1 | 10/2001 | Grubbs et al. | |
| 6,414,097 B1 | 7/2002 | Grubbs et al. | |
| 6,696,597 B2 | 2/2004 | Pederson et al. | |
| 6,794,534 B2 | 9/2004 | Grubbs et al. | |
| 7,102,047 B2 | 9/2006 | Grubbs et al. | |
| 7,378,528 B2 | 5/2008 | Herrmann et al. | |
| 7,745,652 B2 | 6/2010 | Lysenko et al. | |
| 2009/0264672 A1 | 10/2009 | Abraham et al. | |
| 2010/0145086 A1 | 6/2010 | Schrodi et al. | |
| 2010/0160506 A1 | 6/2010 | Wu et al. | |

FOREIGN PATENT DOCUMENTS

| | | |
|---|---|---|
| CA | 2531977 A1 | 7/2007 |
| WO | WO99/21900 A1 | 5/1999 |
| WO | WO2007/103398 A1 | 9/2007 |
| WO | WO2008/048520 A2 | 4/2008 |
| WO | WO2008/088624 A2 | 7/2008 |
| WO | WO2009020667 | 2/2009 |
| WO | WO2011/133208 A2 | 10/2011 |

OTHER PUBLICATIONS

Zlatanic, A.; Petrovic, Z. S.; Dusek, K. Structure and properties of triolein-based polyurethane networks. Biomacromolecules, 2002, vol. 3, pp. 1048-1056.*

Luong, T. M.; Schriftman, H.; Swern, D. Direct hydroxylation of fats and derivatives with a hydrogen peroxide tungstic acid system. Journal of the American Oil Chemists' Society, 1967, vol. 44, pp. 316-320.*

Damiani, P.; Burini, G. Determination of the triglyceride composition of olive oil by a multistep procedure. Journal of Agricultural and Food Chemistry, 1980, vol. 28, pp. 1232-1236.*

Scholnick, F.; Saggese, E. J.; Wrigley, A. N.; Ault, W. C.; Monroe Jr., H. A.; Zubillaga, M. Urethane foams from animal fats. IV. Rigid foams from epoxidized glycerides. Journal of the American Oil Chemists' Society, 1968, pp. 76-77.*

(Continued)

*Primary Examiner* — Stephen E Rieth
(74) *Attorney, Agent, or Firm* — Bereskin & Parr LLP/S.E.N.C.R.L., s.r.l.; Michael Fenwick

(57) ABSTRACT

Metathesized triacylglycerol polyols derived from certain natural oils, including canola oil, and their related physical properties are disclosed. Such metathesized triacylglycerol polyols are also used as a component of polyurethane applications, including polyurethane foams.

18 Claims, 30 Drawing Sheets

(56) References Cited

OTHER PUBLICATIONS

Dunkle, M. N.; David, F.; Sandra, P.; Vollmer, M. Analysis of triglycerides in vegetable oils using the Agilent 1260 Infinity Analytical SFC System with evaporative light scattering detection. Agilent Technologies. Aug. 1, 2015.*
Rouhi, A. M. Olefin Metathesis: Big-Deal Reaction. Chemical & Engineering News, 2002, vol. 80, No. 51, pp. 29-33.*
J.C. Mol. Application of olefin metathesis in oleochemistry: an example of green chemistry. Green Chem. 4:5-13, 2002.
T. Gibson and L.Tulich. Novel Synthesis of Long-chain Primary Alkyl Compounds. J. Org. Chem. 46:1821-1823, 1981.
G. Doyle. Olefin Metatheesis Catalyzed by Zero-Valent, Anionic Group VI Metal Comounds. J. Catal. 30:118-127, 1973.
R. Spronk and J.C. Mol. Metathesis of 1-alkenes in the liquid phase over a Re2O7/gamma-Al2O3 caatalyst. Applied Catalysis 70:295-306, 1991.
Harold H. Fox, Richard R. Schrock,. and Rick O'Dell. Coupling of Terminal Olefins by Molybdenum(V1) Imido Alkylidene Complexes. Organometallics 13:635-639, 1994.
K.J. Ivin and J.C. Mol. Olefin Metathesis and Metathesis Polyermization. Survey of Catalyst Systems, Chapter 2, pp. 12-49, 1997.

* cited by examiner

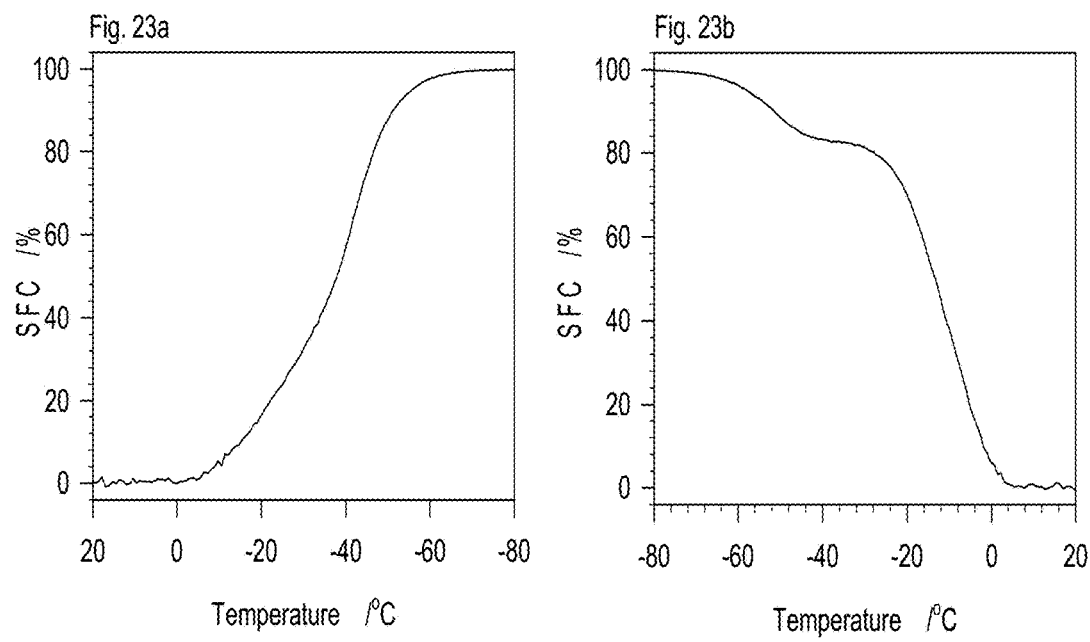
Figure 23a-b
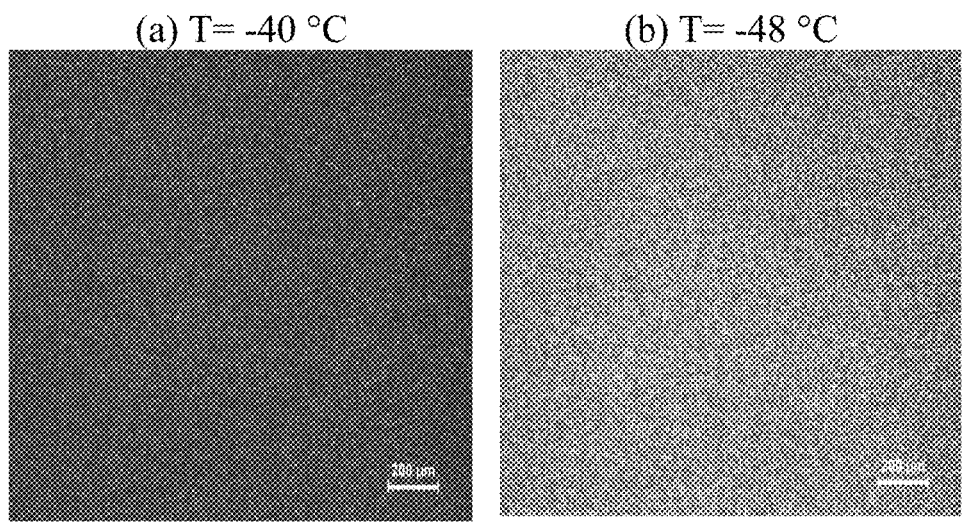
Figures 24a-b

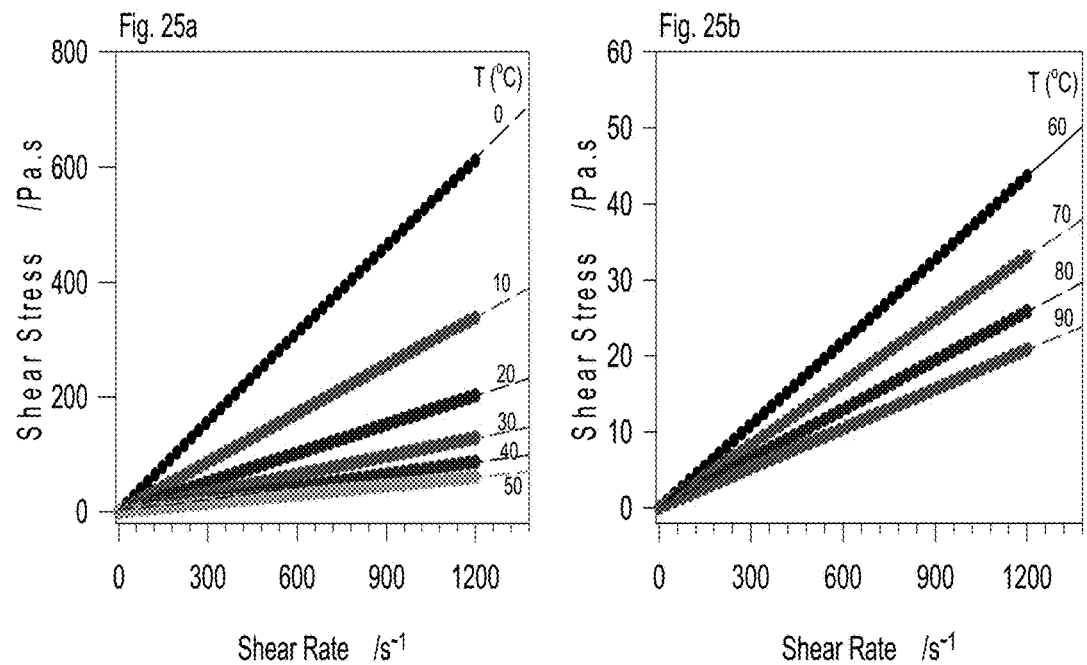
Figures 25a-b
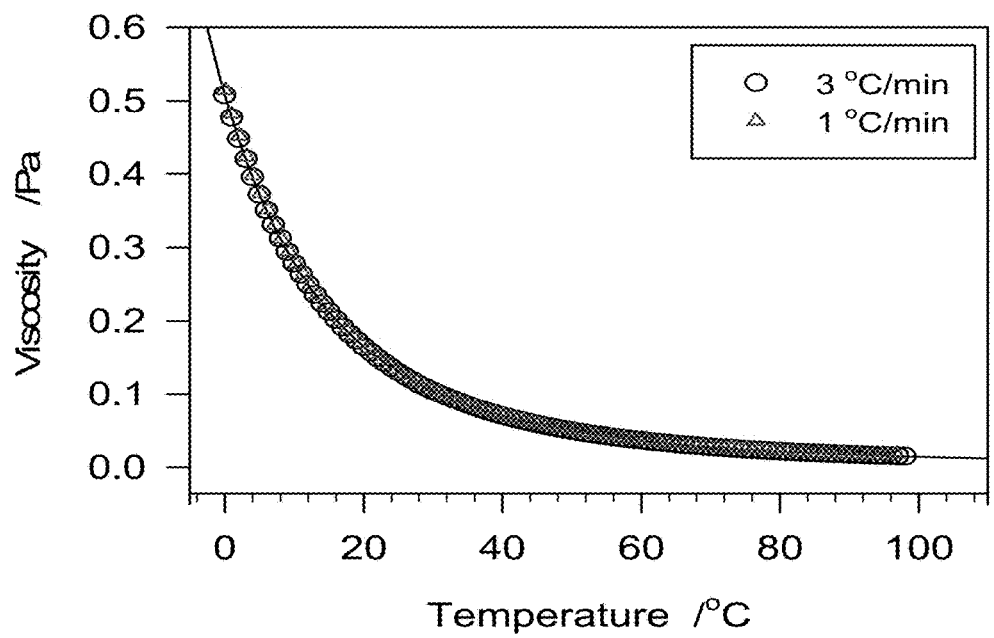
Figure 26

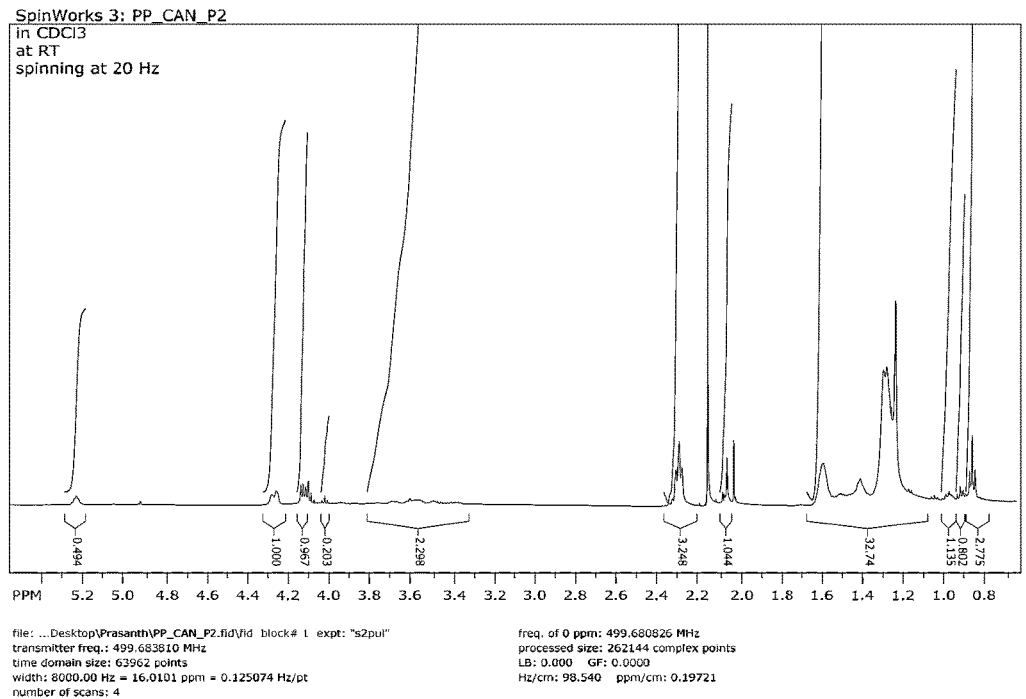
Figure 29
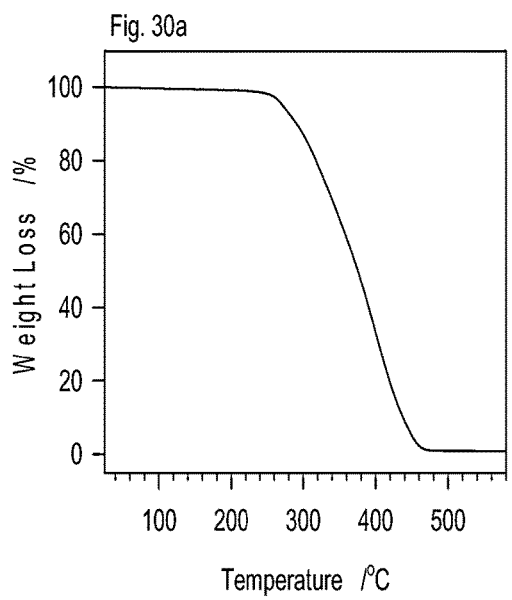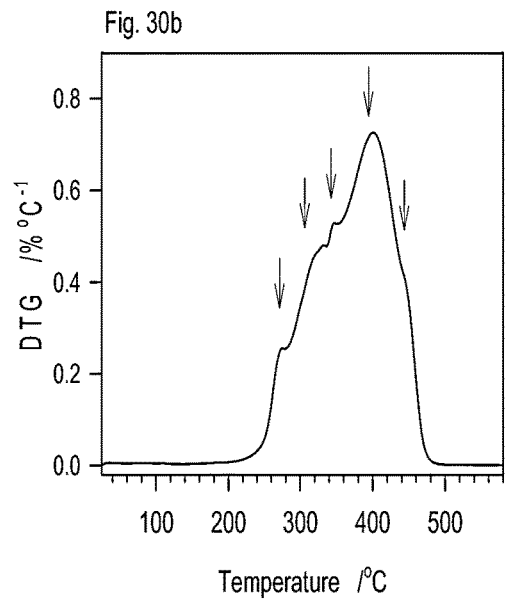
Figures 30a-b

Figure 34a-b

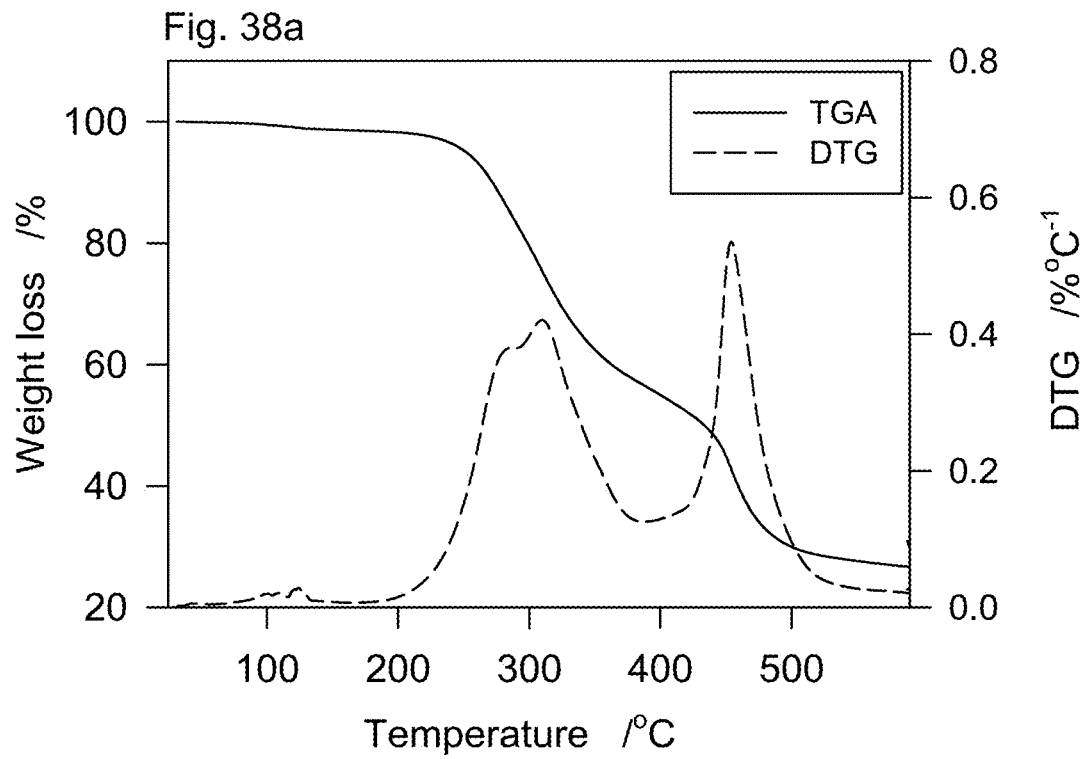
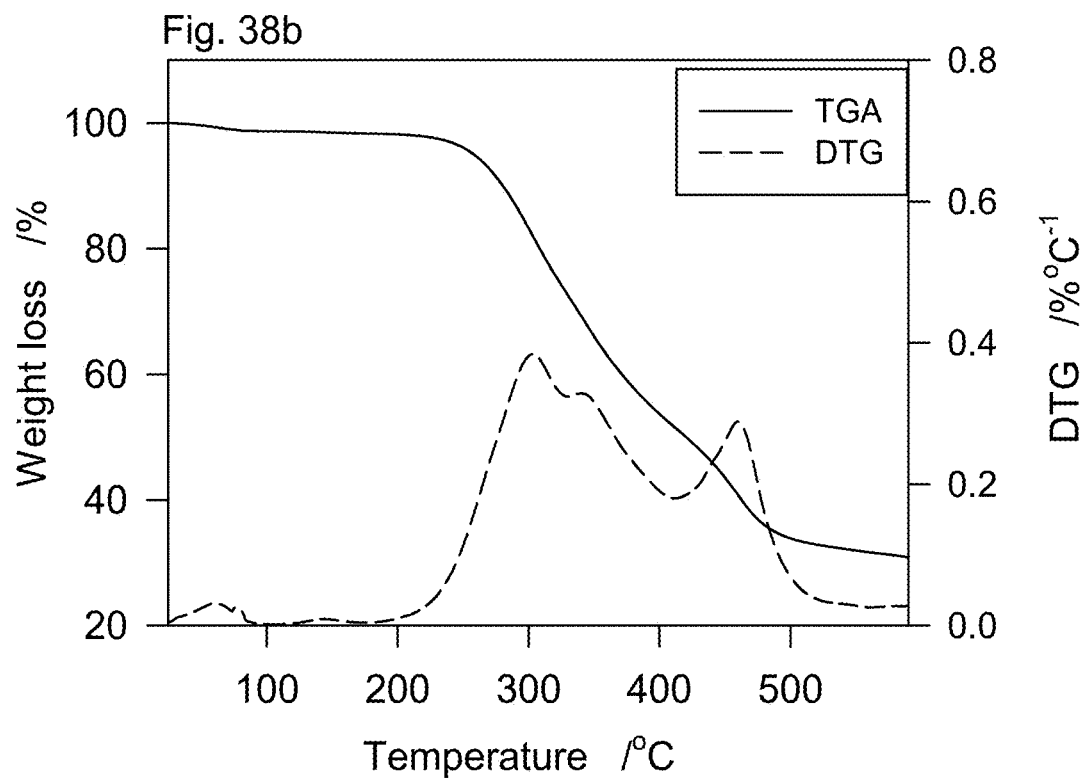
Figures 38a-b

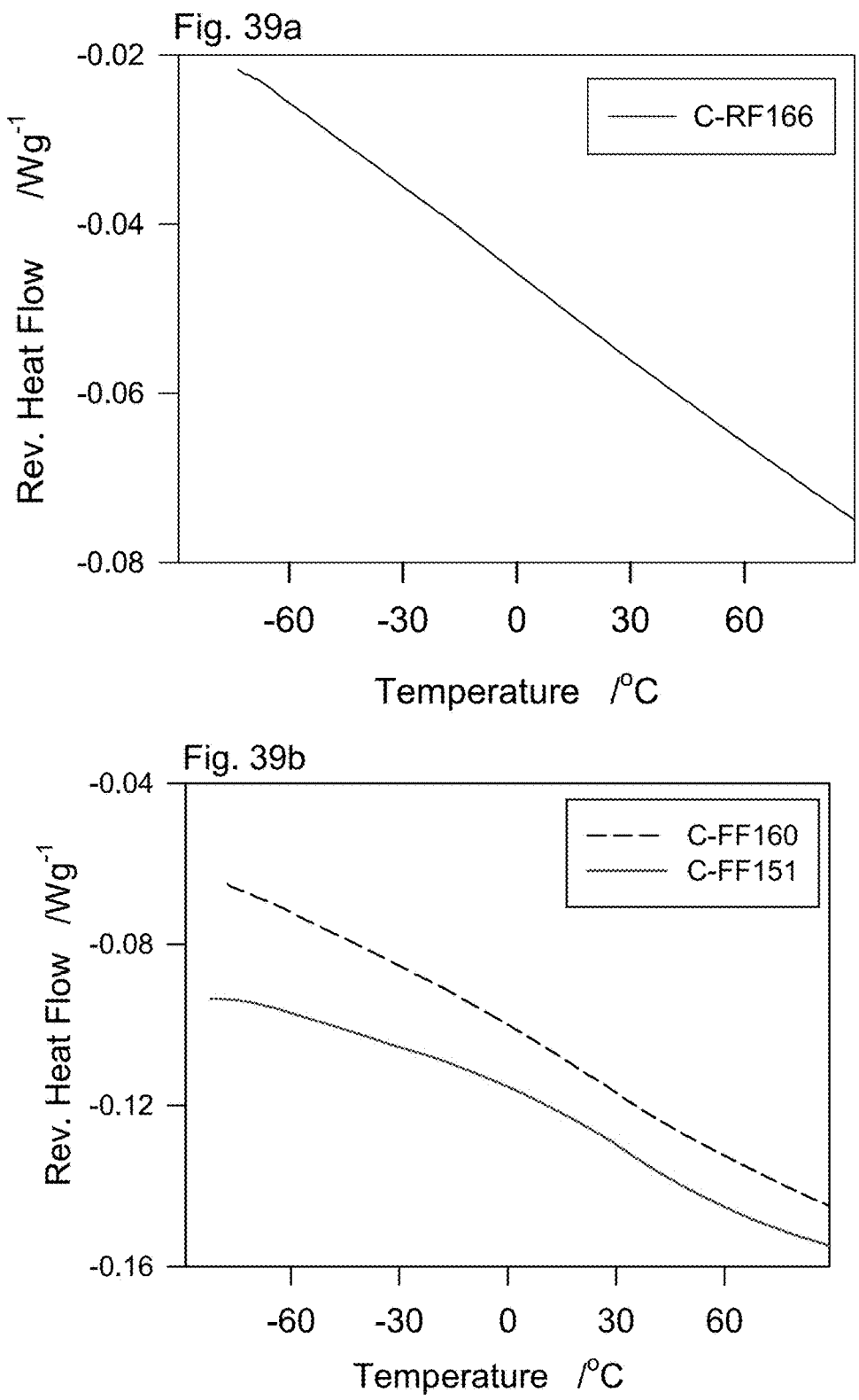
Figures 39a-b ature of the Invention

CERTAIN METATHESIZED NATURAL OIL TRIACYLGLYCEROL POLYOLS FOR USE IN POLYURETHANE APPLICATIONS AND THEIR RELATED PROPERTIES

CROSS REFERENCE TO RELATED APPLICATIONS

A claim of priority for this application under 35 U.S.C. § 119(e) is hereby made to the following U.S. Provisional Patent Applications: U.S. Ser. No. 62/107,404 filed Jan. 24, 2015; and U.S. Ser. No. 61/971,475 filed Mar. 27, 2014; and these applications are incorporated herein by reference in their entireties.

TECHNICAL FIELD

This application relates to certain metathesized natural oil triacylglycerol polyols and their related physical properties. Such metathesized triacylglycerol polyols are also used as a component in polyurethane applications, including polyurethane foams.

BACKGROUND

Polyurethanes are one of the most versatile polymeric materials with regards to both processing methods and mechanical properties. Polyurethanes are formed either based on the reaction of NCO groups and hydroxyl groups, or via non-isocyanate pathways, such as the reaction of cyclic carbonates with amines, self-polycondensation of hydroxyl-acyl azides or melt transurethane methods. The most common method of urethane production is via the reaction of a polyol and an isocyanate which forms the backbone urethane group. Cross-linking agents, chain extenders, blowing agents and other additives may also be added as needed. The proper selection of reactants enables a wide range of polyurethane elastomers, sheets, foams, and the like.

Traditionally, petroleum-derived polyols have been widely used in the manufacturing of polyurethane foams. However, there has been an increased interest in the use of renewable resources in the manufacturing of polyurethane foams. This has led to research into developing natural oil-based polyols for use in the manufacturing of foams. The present effort details the synthesis of certain natural oil based metathesized triacylglycerols (MTAG) and polyols thereof. Such natural oils may include canola, rapeseed, olive, soy, sunflower, safflower, linseed, tung, mustard, camelina, hemp, algal, castor, and canola oil, and such canola oil based metathesized triacylglycerols may be referred to as canola oil MTAG or CMTAG. Any polyols derived from such metathesized triacylglycerols may be utilized in polyurethane applications, such as rigid and flexible polyurethane foams. The present effort also discloses physical and thermal properties of such polyols, and the formulation of polyurethane applications (such as foams) using such polyols as a component.

BRIEF DESCRIPTION OF THE DRAWINGS

FIG. 23a depicts SFC versus temperature curves of CMTAG obtained during cooling at 5° C./min.
FIG. 23b depicts SFC versus temperature curves of CMTAG obtained during subsequent heating at 5° C./min.
FIG. 24a depicts PLM images (100×) of CMTAG taken during cooling (5° C./min) from the melt at T=−40° C.

FIG. 24b depicts PLM images (100×) of CMTAG taken during cooling (5° C./min) from the melt at T=−48° C.

FIG. 25a depicts shear rate versus shear stress curves of CMTAG measured at 0 to 50° C., FIG. 25b depicts shear rate versus shear stress curves of CMTAG measured at 60° C. to 90° C.

FIG. 26 depicts viscosity versus temperature curves obtained during cooling of CMTAG at (○) 3° C./min and (Δ) 1° C./min. Solid line is a guide for the eye.

FIG. 29 depicts $^1$H-NMR spectrum of CMTAG Polyol produced by the epoxidation and hydrogenation synthesis route.

FIG. 30a depicts TGA (10° C./min) of CMTAG Polyol.

FIG. 30b depicts DTG profiles of CMTAG Polyol.

FIG. 38a depicts TGA (10° C./min) and DTG curves of rigid CMTAG Polyol foam.

FIG. 38b depicts TGA (10° C./min) and DTG curves of flexible CMTAG Polyol foam.

FIG. 39a depicts DSC thermograms of rigid CMTAG Polyol foam.

FIG. 39b depicts DSC thermograms of flexible CMTAG Polyol foam.

C-RF166: Rigid CMTAG Polyol foam with density of 166 kg/m$^3$.

Figure 41:
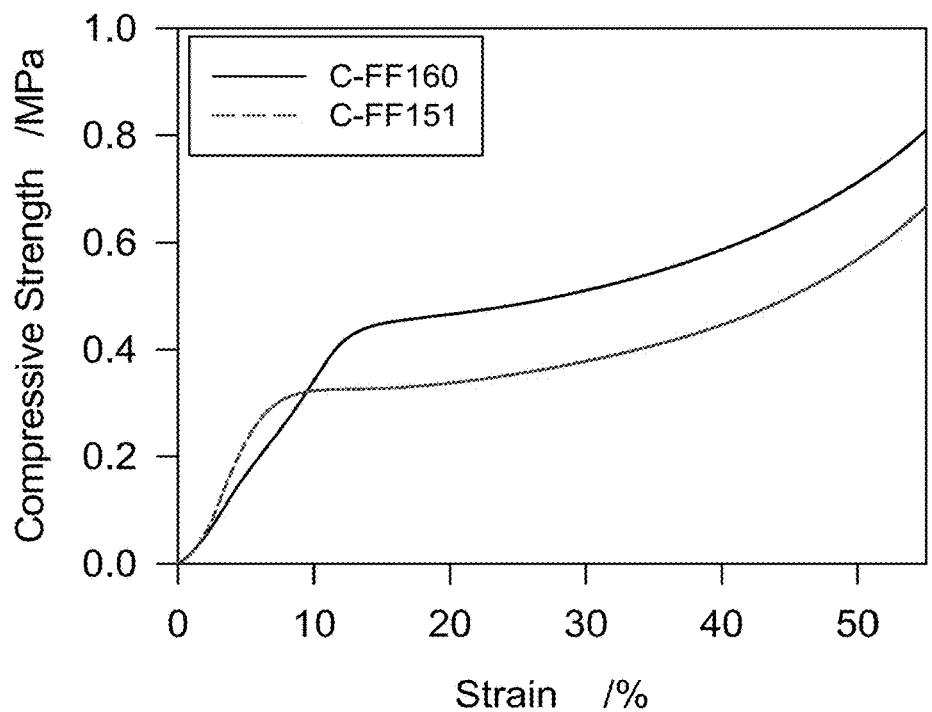

FIG. 41 depicts compressive strength versus strain of flexible CMTAG Polyol foams.

C-FF160 and C-FF151: Flexible Canola MTAG Polyol foam with density of 160 and 151 kg/m$^3$, respectively.

Figure 42:
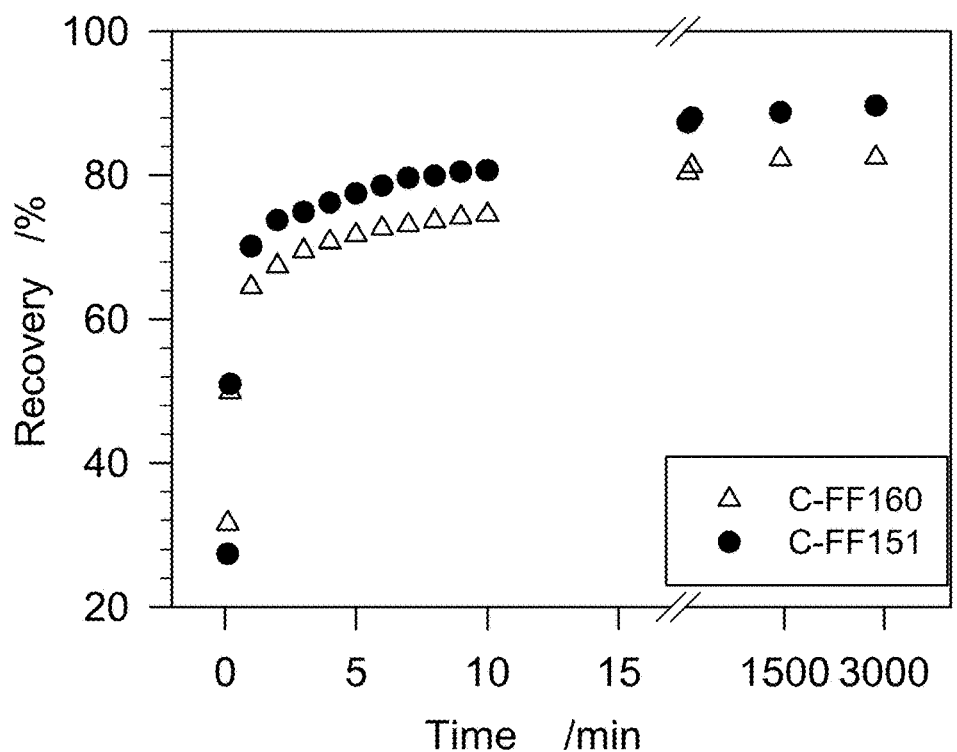

FIG. 42 depicts % Recovery of flexible CMTAG Polyol foams as a function of time. C-FF160 and C-FF151: flexible Canola MTAG Polyol foam with density of 160 and 151 kg/m$^3$, respectively.

Figure 43:
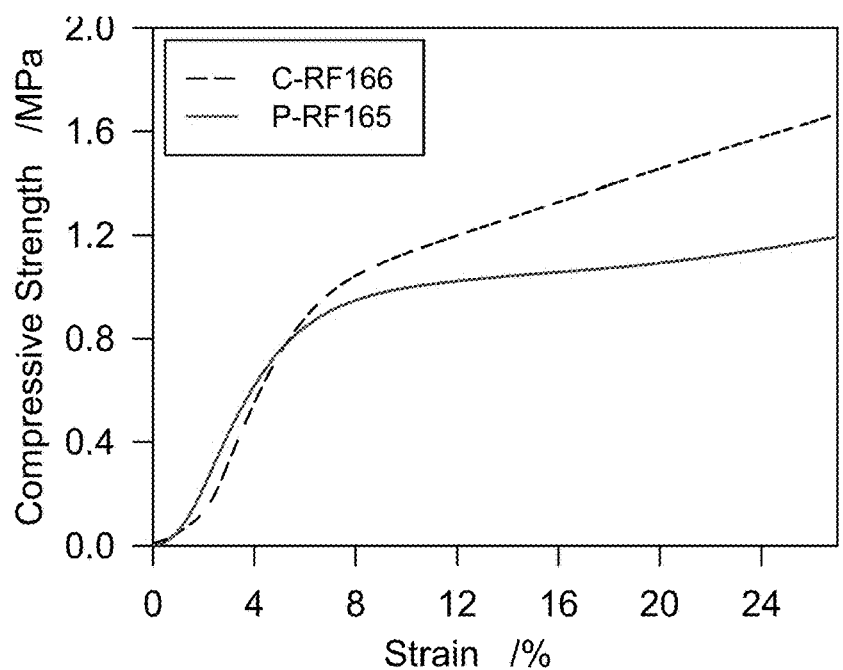

FIG. 43 depicts stress versus strain curves of rigid CMTAG Polyol foam (C-RF166, density=166 kg/m$^3$) and rigid PMTAG foam (P-RF165, density=165 kg/m$^3$).

Figure 44:
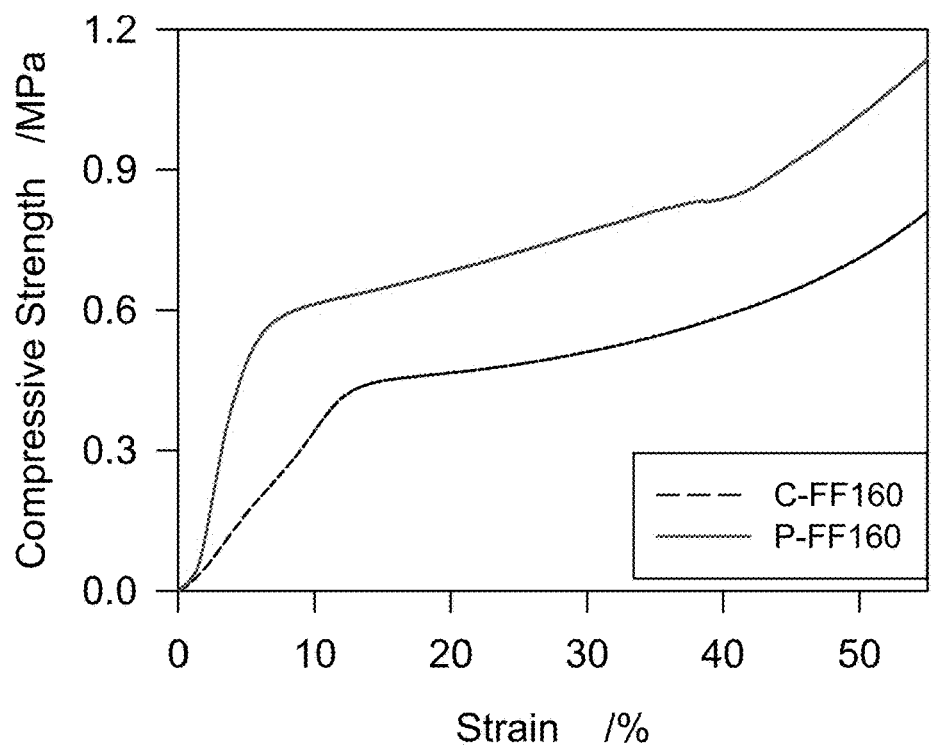

FIG. 44 depicts compressive strength versus strain of flexible CMTAG Polyol and PMTAG Polyol foams. C-FF160: flexible CMTAG Polyol foam having density of 160 kg/m$^3$, and P-FF160: flexible PMTAG Polyol foam having density of 160 kg/m$^3$.

Figure 45:
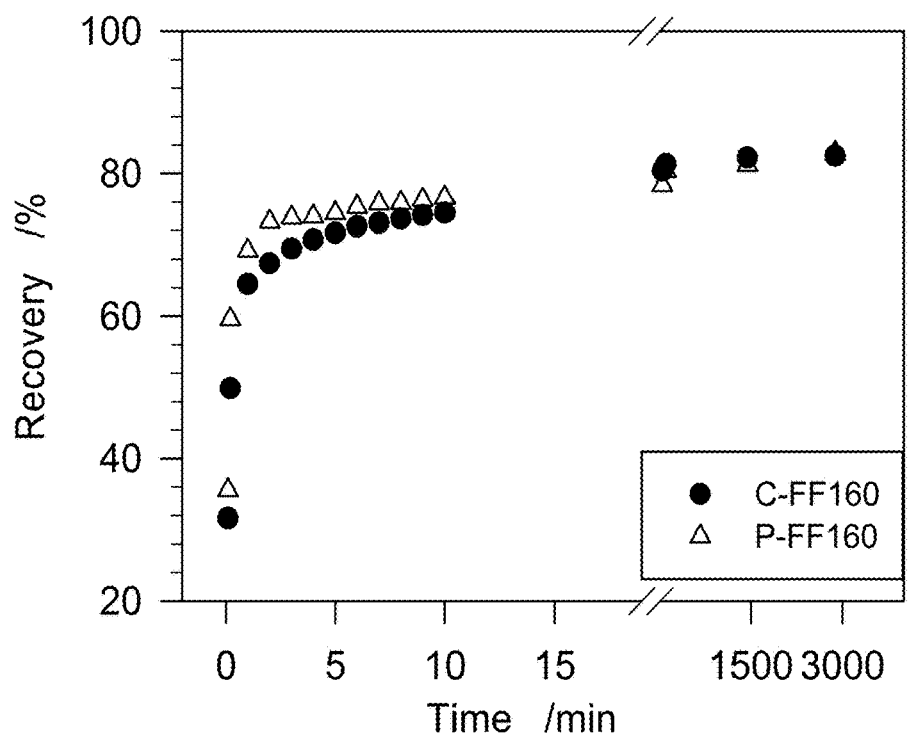

FIG. 45 depicts the recovery (%) of flexible CMTAG Polyol and PMTAG Polyol foams (C-FF160 and P-FF164, respectively) as a function of time. C-FF160: flexible CMTAG Polyol foam having density of 160 kg/m$^3$, and P-FF160: flexible PMTAG Polyol foam having density of 160 kg/m$^3$.

DETAILED DESCRIPTION

A. Metathesized Triacylglycerols of Certain Natural Oils

Synthesis of Metathesized Triacylglycerols for Production of Polyols

The synthesis of rigid and flexible polyurethane foams and other polyurethanes from certain natural oils (such as canola, rapeseed, olive, soy, sunflower, safflower, linseed, tung, mustard, camelina, hemp, algal, castor, and canola oil, for example) based metathesized triacylglycerols (including canola oil MTAG or CMTAG) and polyols thereof, begins with the initial synthesis of the CMTAGs themselves. A general definition of a metathesized triacylglycerol is the product formed from the metathesis reaction (self-metathesis or cross-metathesis) of an unsaturated triacylglycerol in the presence of a metathesis catalyst to form a product including one or more metathesis monomers, oligomers, or polymers.

Metathesis is a catalytic reaction that involves the interchange of alkylidene units among compounds containing one or more double bonds (i.e., olefinic compounds) via the formation and cleavage of the carbon-carbon double bonds. The metathesis catalyst in this reaction may include any catalyst or catalyst system that catalyzes a metathesis reaction. Generally, cross metathesis may be represented schematically as shown in Scheme 1 below:

Scheme 1.

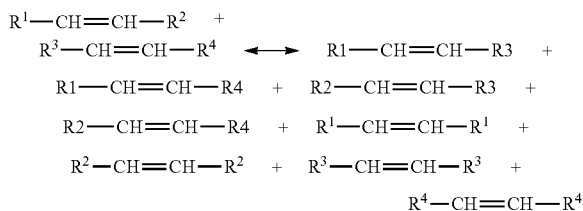

Representation of cross-metathesis reaction. Wherein R$^1$, R$^2$, R$^3$, and R$^4$ are organic groups. Suitable homogeneous metathesis catalysts include combinations of a transition metal halide or oxo-halide (e.g., WOCl$_4$ or WCl$_6$) with an alkylating cocatalyst (e.g., Me$_4$Sn). Homogeneous catalysts include well-defined alkylidene (or carbene) complexes of transition metals, particularly Ru, Mo, or W. These include first and second-generation Grubbs catalysts, Grubbs-Hoveyda catalysts, and the like. Suitable alkylidene catalysts have the general structure:

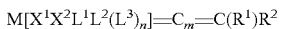

where M is a Group 8 transition metal, L$^1$, L$^2$, and L$^3$ are neutral electron donor ligands, n is 0 (such that L$^3$ may not be present) or 1, m is 0, 1, or 2, X$^1$ and X$^2$ are anionic ligands, and R$^1$ and R$^2$ are independently selected from H, hydrocarbyl, substituted hydrocarbyl, heteroatom-containing hydrocarbyl, substituted heteroatom-containing hydrocarbyl, and functional groups. Any two or more of X$^1$, X$^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086 ("the '086 publication"), the teachings of which related to all metathesis catalysts are incorporated herein by reference. Second-generation Grubbs catalysts also have the general formula described above, but $L^1$ is a carbene ligand where the carbene carbon is flanked by N, O, S, or P atoms, e.g., by two N atoms. The carbene ligand may be part of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like. In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. A neutral oxygen or nitrogen may coordinate to the metal while also being bonded to a carbon that is α-, β-, or γ- with respect to the carbene carbon to provide the bidentate ligand. Examples of suitable Grubbs-Hoveyda catalysts appear in the '086 publication.

The structures below (Scheme 2) provide just a few illustrations of suitable catalysts that may be used:

Scheme 2. Structures of few metathesis catalysts

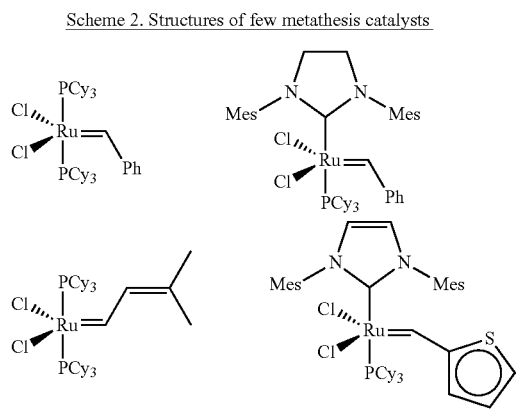

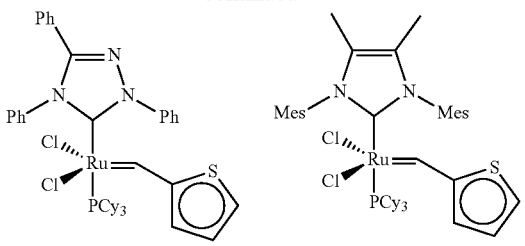

Heterogeneous catalysts suitable for use in the self- or cross-metathesis reactions include certain rhenium and molybdenum compounds as described, e.g., by J.C. Mol in *Green Chem.* 4 (2002) 5 at pp. 11-12. Particular examples are catalyst systems that include $Re_2O_7$ on alumina promoted by an alkylating cocatalyst such as a tetraalkyl tin lead, germanium, or silicon compound. Others include $MoCl_3$ or $MoCl_5$ on silica activated by tetraalkyltins. For additional examples of suitable catalysts for self- or cross-metathesis, see U.S. Pat. No. 4,545,941, the teachings of which are incorporated herein by reference, and references cited therein. See also *J. Org. Chem.* 46 (1981) 1821; *J. Catal.* 30 (1973) 118; *Appl. Catal.* 70 (1991) 295; *Organometallics* 13 (1994) 635; *Olefin Metathesis and Metathesis Polymerization* by Ivin and Mol (1997), and *Chem. & Eng. News* 80(51), Dec. 23, 2002, p. 29, which also disclose useful metathesis catalysts. Illustrative examples of suitable catalysts include ruthenium and osmium carbene catalysts as disclosed in U.S. Pat. Nos. 5,312,940, 5,342,909, 5,710,298, 5,728,785, 5,728,917, 5,750,815, 5,831,108, 5,922,863, 6,306,988, 6,414,097, 6,696,597, 6,794,534, 7,102,047, 7,378,528, and U.S. Pat. Appl. Publ. No. 2009/0264672 A1, and PCT/US2008/009635, pp. 18-47, all of which are incorporated herein by reference. A number of metathesis catalysts that may be advantageously employed in metathesis reactions are manufactured and sold by Materia, Inc. (Pasadena, Calif.).

As a non-limiting aspect, a route to obtain CMTAG may be via the cross metathesis of a natural oil (canola oil) with a lower weight olefin. As a non-limiting aspect, reaction routes using triolein with 1,2-butene and triolein with ethylene are shown below in Scheme 3a and 3b, respectively.

Scheme 3a. Metathesis reaction of triolein with 1,2-butylene.

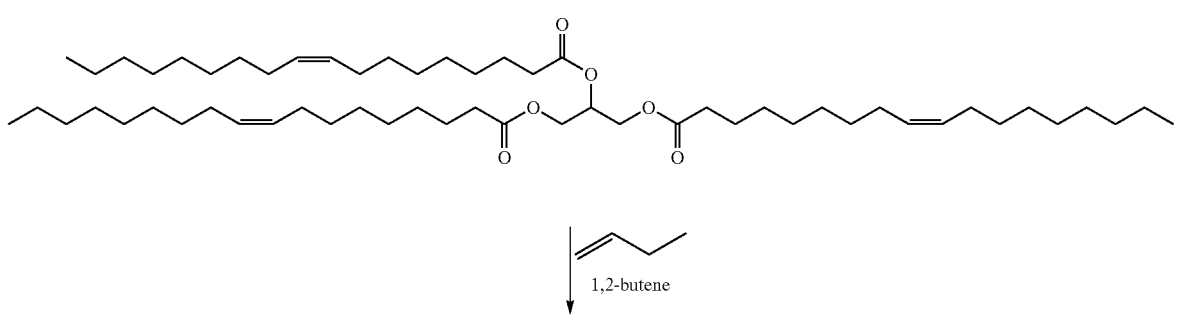

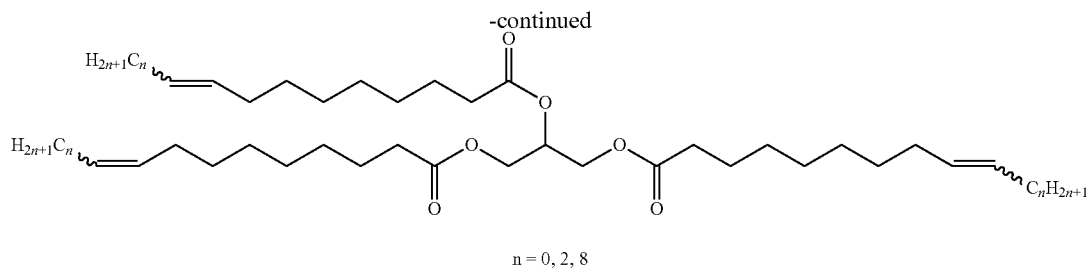

n = 0, 2, 8 n = 0, the fatty acid is 9-denenoic acid (D), n = 2, the fatty acid is 9-dodecenoic acid (Dd) and n = 8, the fatty acid is oleic acid (O).

Scheme 3b. Metathesis reaction of triolein with ethylene.

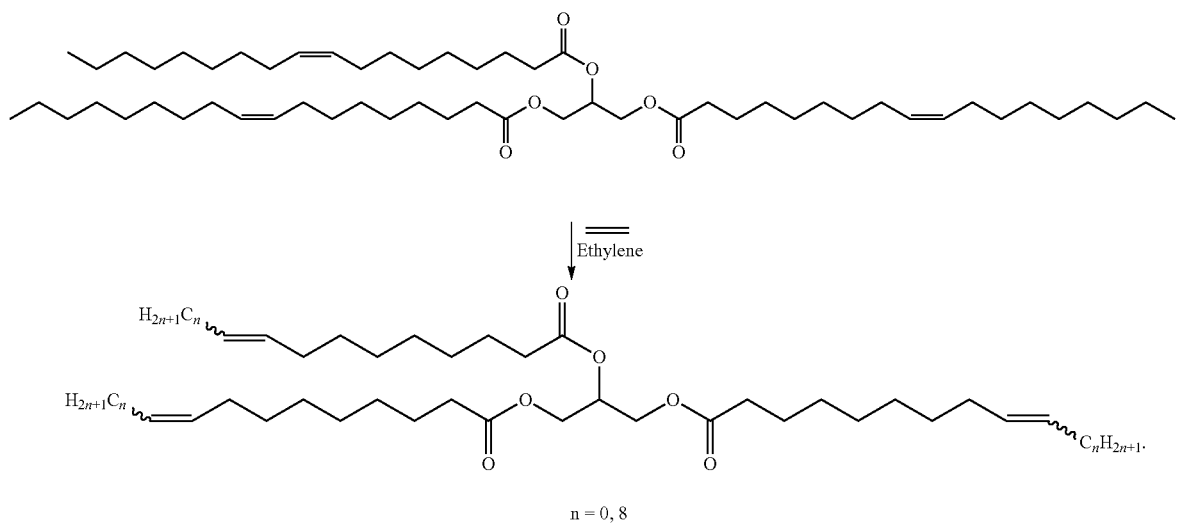

n = 0, 8 n = 0, the fatty acid is 9-denenoic acid (D), and n = 8, the fatty acid is oleic acid (O)

As used herein, the term "lower weight olefin" may refer to any one or a combination of unsaturated straight, branched, or cyclic hydrocarbons in the $C_2$ to $C_{14}$ range. Lower weight olefins include "alpha-olefins" or "terminal olefins," wherein the unsaturated carbon-carbon bond is present at one end of the compound. Lower weight olefins may also include dienes or trienes. Examples of low weight olefins in the $C_2$ to $C_6$ range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Other possible low weight olefins include styrene and vinyl cyclohexane. In certain embodiments, a mixture of olefins may be used, the mixture including linear and branched low weight olefins in the $C_4$-$C_{10}$ range. In one embodiment, a mixture of linear and branched $C_4$ olefins may be used (e.g., combinations of: 1-butene, 2-butene, and/or isobutene). In other embodiments, a higher range of $C_{11}$-$C_{14}$ may be used.

As used herein, the term "natural oil" may refer to oil derived from plants or animal sources. The term "natural oil" includes natural oil derivatives, unless otherwise indicated. Examples of natural oils include, but are not limited to, vegetable oils, algal oils, animal fats, tall oils, derivatives of these oils, combinations of any of these oils, and the like. Representative non-limiting examples of vegetable oils include canola oil, rapeseed oil, coconut oil, corn oil, cottonseed oil, jojoba oil, olive oil, palm oil, peanut oil, safflower oil, sesame oil, soybean oil, sunflower oil, linseed oil, palm kernel oil, tung oil, jatropha oil, mustard oil, camelina oil, pennycress oil, hemp oil, algal oil, and castor oil. Representative non-limiting examples of animal fats include lard, tallow, poultry fat, yellow grease, and fish oil. Tall oils are by-products of wood pulp manufacture. In certain embodiments, the natural oil is selected from the group consisting of canola, rapeseed, olive, soy, sunflower, safflower, linseed, tung, mustard, camelina, hemp, algal, and castor oil. In certain embodiments, the natural oil may be refined, bleached, and/or deodorized. In some embodiments, the natural oil may be partially or fully hydrogenated. In some embodiments, the natural oil is present individually or as mixtures thereof.

Natural oils may include triacylglycerols of saturated and unsaturated fatty acids. Suitable fatty acids may be saturated or unsaturated (monounsaturated or polyunsaturated) fatty acids, and may have carbon chain lengths of 3 to 36 carbon atoms. Such saturated or unsaturated fatty acids may be aliphatic, aromatic, saturated, unsaturated, straight chain or branched, substituted or unsubstituted and mono-, di-, tri-, and/or poly-acid variants, hydroxy-substituted variants, aliphatic, cyclic, alicyclic, aromatic, branched, aliphatic- and alicyclic-substituted aromatic, aromatic-substituted aliphatic and alicyclic groups, and heteroatom substituted variants thereof. Any unsaturation may be present at any suitable isomer position along the carbon chain as would be obvious to a person skilled in the art.

Some non-limiting examples of saturated fatty acids include propionic, butyric, valeric, caproic, enanthic, caprylic, pelargonic, capric, undecylic, lauric, tridecylic, myristic, pentadecanoic, palmitic, margaric, stearic, nonadecyclic, arachidic, heneicosylic, behenic, tricosylic, lignoceric, pentacoyslic, cerotic, heptacosylic, carboceric, montanic, nonacosylic, melissic, lacceroic, psyllic, geddic, ceroplastic acids.

Some non-limiting examples of unsaturated fatty acids include butenoic, pentenoic, hexenoic, pentenoic, octenoic, nonenoic acid, decenoic acid, undecenoic acid, dodecenoic acid, tridecenoic, tetradecenoic, pentadecenoic, palmitoleic, palmitelaidic, oleic, ricinoleic, vaccenic, linoleic, linolenic, elaidic, eicosapentaenoic, behenic and erucic acids. Some unsaturated fatty acids may be monounsaturated, diunsaturated, triunsaturated, tetraunsaturated or otherwise polyunsaturated, including any omega unsaturated fatty acids.

In a triacylglycerol, each of the carbons in the triacylglycerol molecule may be numbered using the stereospecific numbering (sn) system. Thus one fatty acyl chain group is attached to the first carbon (the sn-1 position), another fatty acyl chain is attached to the second, or middle carbon (the sn-2 position), and the final fatty acyl chain is attached to the third carbon (the sn-3 position). The triacylglycerols described herein may include saturated and/or unsaturated fatty acids present at the sn-1, sn-2, and/or sn-3 position In some embodiments, the natural oil is a canola oil. Canola oil may be a liquid at room temperature and includes approximately 6% saturated fatty acids and approximately 94% unsaturated fatty acids, mainly of oleic acid and linoleic acid with ~60% and ~20.1%, respectively. Canola oil may include predominately fatty acid triacylglycerols, although monoacylglycerols and diacylglycerols may also be present in small amounts. The fatty acids may have chain lengths ranging from C14 to C22. Representative saturated fatty acids include, for example, C14:0, C16:0, C18:0, C20:0, and C22:0 saturated fatty acids. Representative unsaturated fatty acids include, for example, C16:1, C18:1, C18:2, C18:3, C20:1, and C22:1 unsaturated fatty acids. As used herein, metathesized triacylglycerols derived from canola oil may be referred to interchangeably as "canola oil MTAG," "CMTAG," or "MTAG of/from canola oil."

The fatty acid and triacylglycerol (TAG) profiles of canola oil are listed in Table 1 and Table 2, respectively.

TABLE 1

Fatty acid profile of canola oil.

| SFA | C14:0 | C16:0 | C18:0 | C20:0 | C22:0 |
|---|---|---|---|---|---|
| Content (%) | 0.1 | 3.5 | 1.5 | 0.6 | 0.3 |

| UFA | C16:1 | C18:1 | C18:2 | C18:3 | C20:1 | C22:1 |
|---|---|---|---|---|---|---|
| Content (%) | 0.2 | 60.1 | 20.1 | 9.6 | 1.4 | 0.2 |

SFA: Saturated fatty acid;
UFA: Unsaturated fatty acid

TABLE 2

TAG profiles of canola oil.

| TAG | LLLn | OLnLn | LOLn | LLL | LPLn | LLO | LnOO | LLP | LnOP |
|---|---|---|---|---|---|---|---|---|---|
| Content (%) | 1.0 | 1.1 | 1.1 | 5.3 | 0.4 | 8.5 | 8.9 | 1.0 | 1.2 |
| TAG | LOO | LOP | SLnP | OOO | OOP | OPP | OOS | | |
| Content (%) | 24.3 | 3.6 | 1.2 | 33.0 | 5.6 | 1.7 | 2.2 | | |

(L: linoleic acid; Ln: linolenic acid; O: oleic acid; P: palmitic acid; S: stearic acid).

Analytical Methods for Canola Oil MTAG

The canola oil MTAG was analyzed using different techniques. These techniques can be broken down into: (i) chemistry characterization techniques, including iodine value, acid value, nuclear magnetic resonance (NMR), and high pressure liquid chromatography (HPLC); and (ii) physical characterization methods, including thermogravimetric analysis (TGA), differential scanning calorimetry (DSC), rheology, solid fat content (SFC), and polarized light microscopy (PLM).

Chemistry Characterization Techniques

Iodine and acid values of the CMTAG was determined according to ASTM D5554-95 and ASTM D4662-03, respectively.

$^1$H-NMR spectra were recorded on a Varian Unity-INOVA at 499.695 MHz. $^1$H chemical shifts are internally referenced to $CDCl_3$ (7.26 ppm) for spectra recorded in $CDCl_3$. All spectra were obtained using an 8.6 μs pulse with 4 transients collected in 16 202 points. Datasets were zero-filled to 64 000 points, and a line broadening of 0.4 Hz was applied prior to Fourier transforming the sets. The spectra were processed using ACD Labs NMR Processor, version 12.01.

HPLC analysis was performed on a Waters Alliance (Milford, Mass.) e2695 HPLC system fitted with a Waters ELSD 2424 evaporative light scattering detector. The HPLC system was equipped with an inline degasser, a pump, and an auto-sampler. The ELSD nitrogen flow was set at 25 psi with nebulization and drifting tube maintained at 12° C. and 55° C., respectively. Gain was set at 500. All solvents were HPLC grade and obtained from VWR International, Mississauga, ON. Waters Empower Version 2 software was used for data collection and data analysis. Purity of eluted samples was determined using the relative peak area. The analysis was performed on a C18 column (150 mm×4.6 mm, 5.0 μm, X-Bridge column, Waters Corporation, MA) maintained at 30° C. by column oven (Waters Alliance) at a flow rate of 1 ml/min. The mobile phase was chloroform:acetonitrile (10:90)v run for 25 min, then progressively increased to 40:60 for 15 min then kept constant for another 15 min. The ratio was progressively increased to 70:30 for 10 min and then kept constant for 15 min to wash column. 5 mg/ml (w/v) solution of crude sample in chloroform was filtered through single step filter vial (Thomson Instrument Company, 35540, CA) and 10 μL of CMTAG sample (or 5 μL of Fraction sample) was passed through the C18 column by reversed-phase in isocratic mode.

Physical Characterization Techniques

TGA was carried out on a TGA Q500 (TA Instruments, DE, USA) equipped with a TGA heat exchanger (P/N 953160.901). Approximately 8.0-15.0 mg of sample was loaded in the open TGA platinum pan. The sample was heated from 25 to 600° C. under dry nitrogen at a constant rate of 10° C./min.

DSC measurements were run on a Q200 model (TA Instruments, New Castle, Del.) under a nitrogen flow of 50 mL/min. TAG samples of 3.5 to 6.5 (±0.1) mg were run in hermetically sealed aluminum DSC pans. Crystallization and melting behavior of CMTAG was investigated using standard DSC. The sample was equilibrated at 90° C. for 10 min to erase thermal memory, and then cooled at a constant rate of 5.0° C./min to −90° C. where it was held isothermally for 5 min, and subsequently reheated at a constant rate of 5.0° C./min to 90° C. The "TA Universal Analysis" software was used to analyze the DSC thermograms and extract the peak characteristics. Characteristics of non-resolved peaks were obtained using the first and second derivatives of the differential heat flow.

SFC measurements were performed on a Bruker Minispec mq 20 pNMR spectrometer (Milton, ON, Canada) equipped with a combined high and low temperature probe supplied with $N_2$. The temperature was controlled with Bruker's BVT3000 temperature controller with an accuracy of ±0.1° C. The temperature was calibrated with commercial canola oil using a type K probe (TRP-K, Omega, Stamford, Conn.) immersed in the oil and an external data logger (Oakton, Eutech Instruments, Singapore). Approximately 0.57±0.05 ml of fully melted sample was quickly pipetted into the bottom portion of the NMR tube. The thermal protocol used in the DSC were also used in the NMR. Bruker's minispec V2.58 Rev. 12 and minispec plus V1.1 Rev. 05 software were used to collect SFC data as a function of time and temperature. The SFC values are reported as the ratio of the intensity of the NMR signal of the solid part to the total detected NMR signal in percent (labelled as SFC %).

A Leica DM2500P polarized light microscope (PLM) fitted with a Leica DFC420C digital camera (Leica Microsystems, Wetzlar, Germany) was used for image capture of the microstructure of the CMTAG. The samples were processed in a temperature-controlled stage (Linkam LTS 350) fitted to the PLM. The formation of the fat crystal network from the early crystallites through their growth and aggregation were observed in-situ under the PLM. The micrographs presented (100× and 500×) were captured at −90° C.

A temperature-controlled Rheometer (AR2000ex, TA Instruments, DE, USA) was used to measure the viscosity and flow property of CMTAG using a 40 mm 2° steel geometry. Temperature control was achieved by a Peltier attachment with an accuracy of 0.1° C. Shear Stress was measured at each temperature by varying the shear rate from 1 to 1200 $s^{-1}$. Measurements were taken at 10° C. intervals from high temperature (100° C.) to 10° C. below the DSC onset of crystallization temperature of each sample. Viscosities of samples were measured from each sample's melting point up to 110° C. at constant temperature rate (1.0 and 3.0° C./min) with constant shear rate (200 $s^{-1}$). Data points were collected at intervals of 1° C. The viscosity obtained in this manner was in very good agreement with the measured viscosity using the shear rate/share stress. The shear rate range was optimized for torque (lowest possible is 10 μNm) and velocity (maximum suggested of 40 rad/s).

The shear rate—shear stress curves were fitted with the Herschel-Bulkley equation (Eq. 1), a model commonly used to describe the general behavior of materials characterized by a yield stress.

$$\tau = \tau_0 + K\dot{\gamma}^n \qquad \text{Eq. 1}$$

where $\dot{\gamma}$ denotes the shear stress, $\tau_0$ is the yield stress below which there is no flow, K the consistency index and n the power index. n depends on constitutive properties of the material. For Newtonian fluids n=1, shear thickening fluids, n>1 and for shear thinning fluids, n<1.

Iodine value of Canola Oil MTAG

The Iodine values of the CMTAG determined according to ASTM D5554-95 was 119 g/100 g. The acid value of the CMTAG determined according to ASTM D4662-03 was 0.67 mg KOH/g.

Compositional Analysis of Canola Oil MTAG

The natural oil composition, and in particular, the fatty acid composition of canola oil was described previously, and the TAG profiles of canola oil were also described previously. The TAGs which can potentially compose MTAG based on canola oil (CMTAG) and the possible products of cross-metathesis of canola oil with 1-butylene are listed in Table 3, and their structures are presented in Table 4.

TABLE 3

Potential mono-TAG composition in CMTAG. D: 9-decenoic acid;
Dd: 9-dodecenioc acid; O, oleic acid; P, palmitic acid;
L, linoleic acid; Ln, Linolenic acid; S, stearic acid. There
are both trans- and cis- double bonds in the TAG

| TAGs in Canola oil | Potential TAG composition of CMTAG |
|---|---|
| LLLn | DDD, DDDd, DDdDd, DdDdDd, LDD, LDDd, LDdDd, LLDd, LLD, DdLLn, DLLn, DDLn, DDdLn, DdDdLn, LLLn and their isomers |
| OLnLn | DDD, DDDd, DDdDd, DdDdDd, ODD, ODDd, ODdDd, OLnDd, OLnD, DdLnLn, DLnLn, DDLn, DDdLn, DdDdLn, OLnLn, and their isomers |
| LOLn | DDD, DDDd, DDdDd, DdDdDd, LDD, LDDd, LDdDd, LODd, LOD, DdOLn, DOLn, DDLn, DDdLn, DdDdLn, LOLn, DOD, DdOD, DdODd and their isomers |
| LLL | DDD, DDDd, DDdDd, DdDdDd, LDD, LDDd, LDdDd, LLDd, LLD, LLL and their isomers |
| LLO | DDD, DDDd, DDdDd, DdDdDd, LDD, LDDd, LDdDd, LLDd, LLD, DdLO, DLO, DDO, DDdO, DdDdO, LLO and their isomers |
| LnOO | DDD, DDDd, DDdDd, DdDdDd, LnDD, LnDDd, LnDdDd, LnODd, LnOD, DdOO, DOO, DDO, DDdO, DdDdO, LnOO, , and their isomers |
| OOO | DDD, DDDd, DDdDd, DdDdDd, ODD, ODDd, ODdDd, OODd, OOD, DDO, DDdO, OOO, and their isomers |
| LPLn | DPD, DdPD, DdPDd, LPD, LPDd, LPLn, DPLn, DdPLn and their isomers |
| LLP | DDP, DLP, DDdP, DdDdP and their isomers |
| LOP | DDP, DOP, DDdP, DdDdP, LOP, DdOP, LDP, LDdP and their isomers |
| SLnP | SDP, SDdP, SLnP |
| OOP | POD, PODd, DDP, DdDP, DdDdP, OOP and their isomers |
| OPP | OPP, DPP, DdPP, |
| OOS | SOD, SODd, DDS, DdDS, DdDdS, OOS and their isomers |

TABLE 4

Structures of potential mono-TAGs in CMTAG

| Compound | Structure |
|---|---|
| OLL | 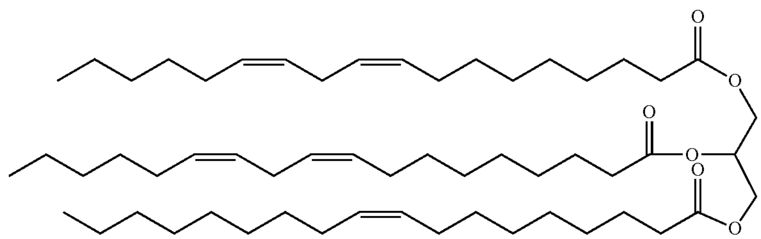 [SMILES: CCCCC/C=C\C/C=C\CCCCCCCC(=O)OCC(COC(=O)CCCCCCC/C=C\CCCCCCCC)OC(=O)CCCCCCC/C=C\C/C=C\CCCCC] |
| OLO | 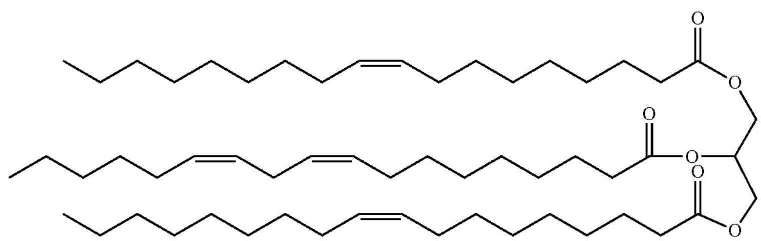 [SMILES: CCCCC/C=C\C/C=C\CCCCCCCC(=O)OC(COC(=O)CCCCCCC/C=C\CCCCCCCC)COC(=O)CCCCCCC/C=C\CCCCCCCC] |
| OOO | 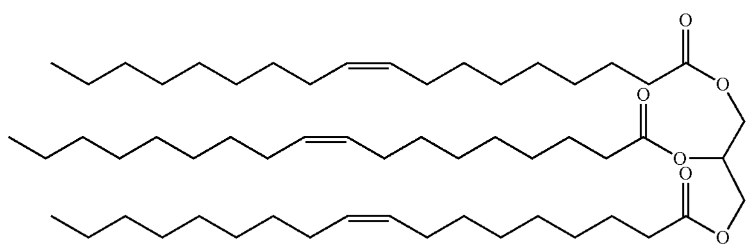 [SMILES: CCCCCCCC/C=C\CCCCCCCC(=O)OCC(COC(=O)CCCCCCC/C=C\CCCCCCCC)OC(=O)CCCCCCC/C=C\CCCCCCCC] |
| ODD | 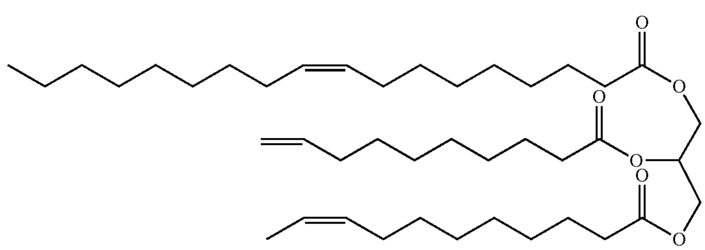 [SMILES: C=CCCCCCCCC(=O)OC(COC(=O)CCCCCCC/C=C\C)COC(=O)CCCCCCC/C=C\CCCCCCCC] |
| DDD | 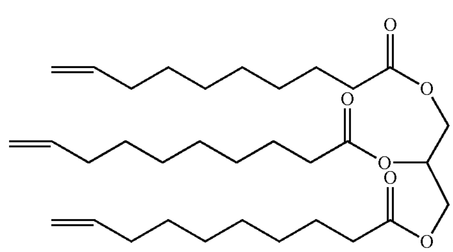 [SMILES: C=CCCCCCCCC(=O)OCC(COC(=O)CCCCCCCC=C)OC(=O)CCCCCCCC=C] |
| DDDd | 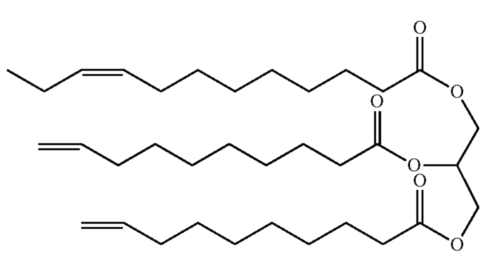 [SMILES: C=CCCCCCCCC(=O)OCC(COC(=O)CCCCCCC/C=C\CC)OC(=O)CCCCCCCC=C] |

TABLE 4-continued

Structures of potential mono-TAGs in CMTAG

| Compound | Structure |
|----------|-----------|
| DDdDd | 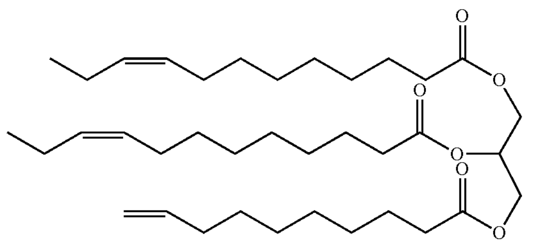 [SMILES: C=CCCCCCCCC(=O)OCC(COC(=O)CCCCCCC/C=C\CC)OC(=O)CCCCCCC/C=C\CC] |
| DLO | 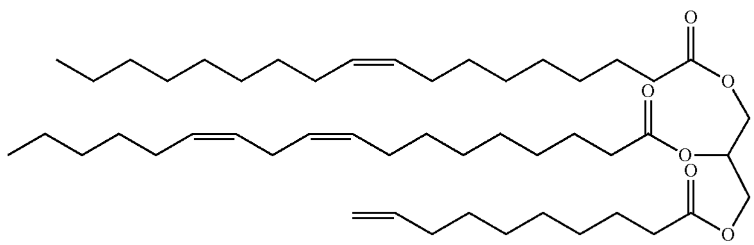 [SMILES: C=CCCCCCCCC(=O)OCC(COC(=O)CCCCCCC/C=C\CCCCCCCC)OC(=O)CCCCCCC/C=C\C/C=C\CCCCC] |
| DdLO | 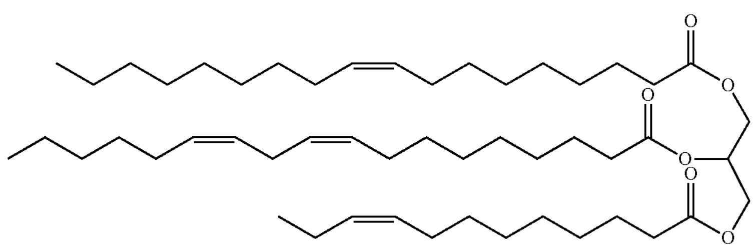 [SMILES: CC/C=C\CCCCCCCC(=O)OCC(COC(=O)CCCCCCC/C=C\CCCCCCCC)OC(=O)CCCCCCC/C=C\C/C=C\CCCCC] |
| OOD | 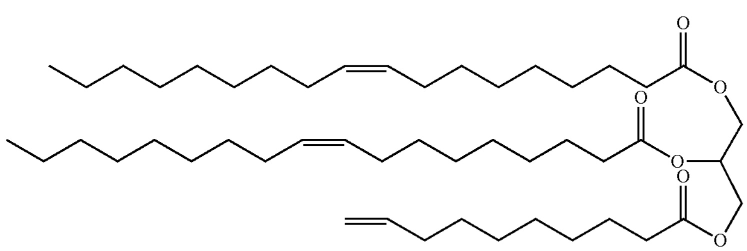 [SMILES: C=CCCCCCCCC(=O)OCC(COC(=O)CCCCCCC/C=C\CCCCCCCC)OC(=O)CCCCCCC/C=C\CCCCCCCC] |
| ODD | 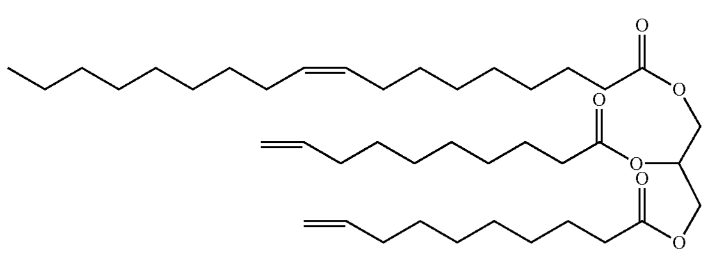 [SMILES: C=CCCCCCCCC(=O)OCC(COC(=O)CCCCCCC/C=C\CCCCCCCC)OC(=O)CCCCCCCC=C] |
| ODDd | 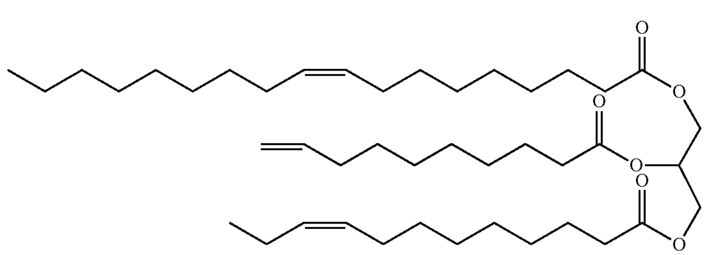 [SMILES: C=CCCCCCCCC(=O)OC(COC(=O)CCCCCCC/C=C\CC)COC(=O)CCCCCCC/C=C\CCCCCCCC] |

TABLE 4-continued
Structures of potential mono-TAGs in CMTAG
| Compound | Structure |
|---|---|
| ODdDd | 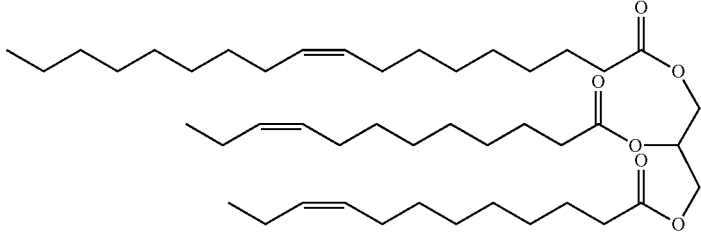 [SMILES: CC/C=C\CCCCCCCC(=O)OCC(COC(=O)CCCCCCC/C=C\CCCCCCCC)OC(=O)CCCCCCC/C=C\CC] |
| LDD | 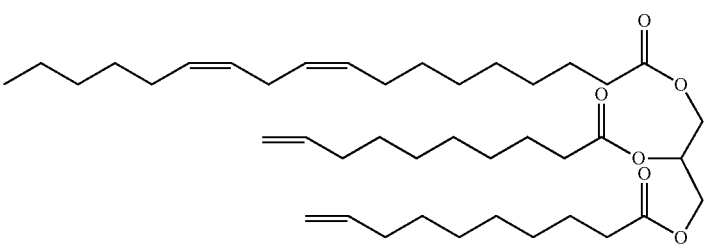 [SMILES: C=CCCCCCCCC(=O)OCC(COC(=O)CCCCCCC/C=C\C/C=C\CCCCC)OC(=O)CCCCCCCC=C] |
| LDDd | 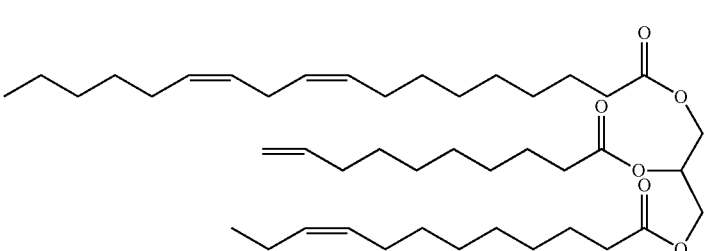 |
| LDdDd | 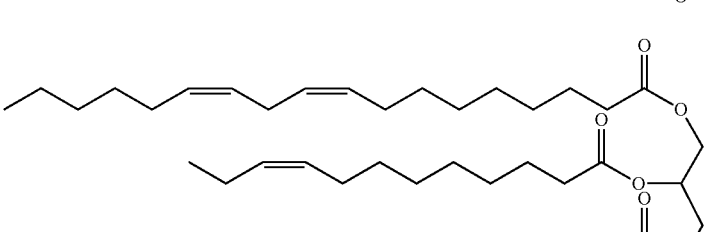 |
| LLD | 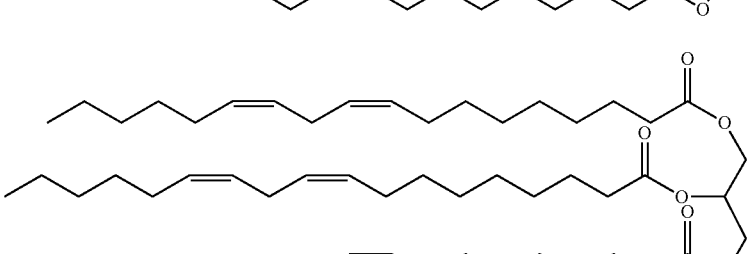 |
| LLDd | 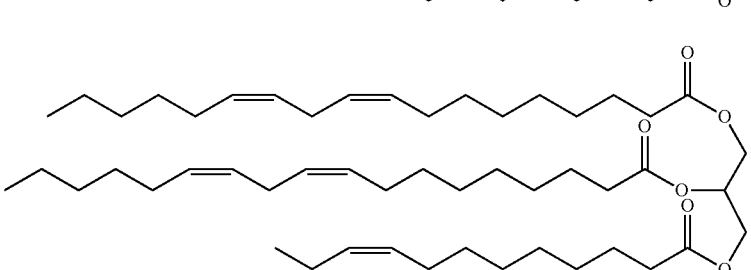 |

TABLE 4-continued

Structures of potential mono-TAGs in CMTAG

| Compound | Structure |
|---|---|
| DdLLn | 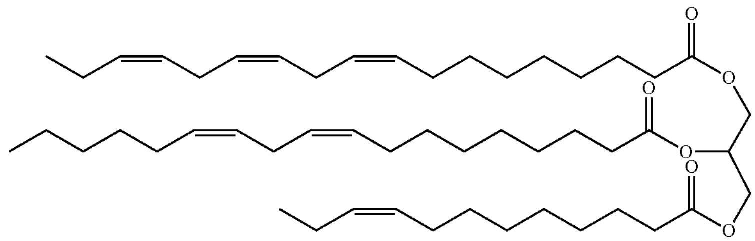 [SMILES: CC/C=C\C/C=C\C/C=C\CCCCCCCC(=O)OCC(COC(=O)CCCCCCC/C=C\CC)OC(=O)CCCCCCC/C=C\C/C=C\CCCCC] |
| DLLn | 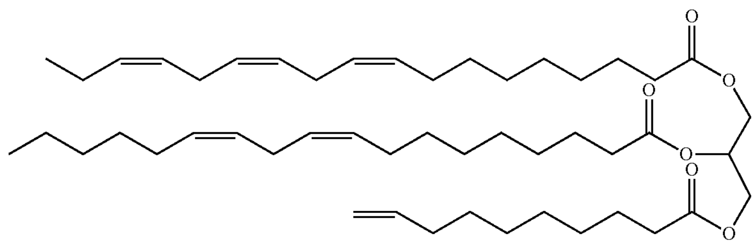 [SMILES: C=CCCCCCCCC(=O)OCC(COC(=O)CCCCCCC/C=C\C/C=C\C/C=C\CC)OC(=O)CCCCCCC/C=C\C/C=C\CCCCC] |
| DdDdLn | 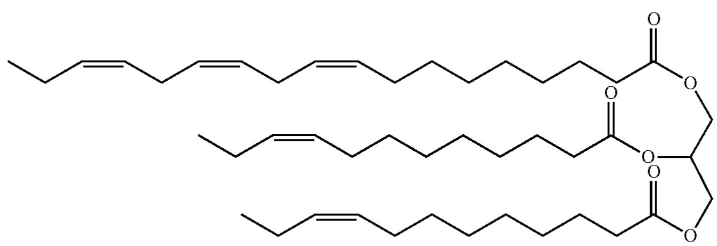 [SMILES: CC/C=C\C/C=C\C/C=C\CCCCCCCC(=O)OCC(COC(=O)CCCCCCC/C=C\CC)OC(=O)CCCCCCC/C=C\CC] |
| DDdLn | 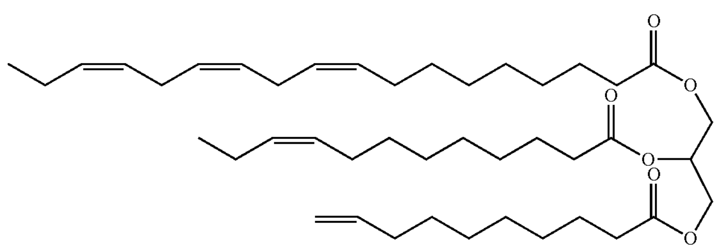 [SMILES: C=CCCCCCCCC(=O)OCC(COC(=O)CCCCCCC/C=C\C/C=C\C/C=C\CC)OC(=O)CCCCCCC/C=C\CC] |
| DDLn | 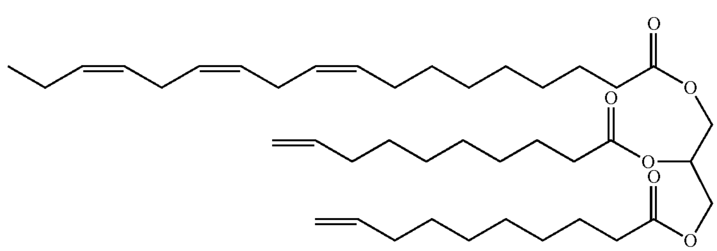 [SMILES: C=CCCCCCCCC(=O)OCC(COC(=O)CCCCCCC/C=C\C/C=C\C/C=C\CC)OC(=O)CCCCCCCC=C] |
| DdDdDd | 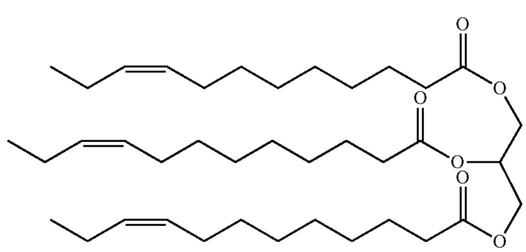 [SMILES: CC/C=C\CCCCCCCC(=O)OCC(COC(=O)CCCCCCC/C=C\CC)OC(=O)CCCCCCC/C=C\CC] |

TABLE 4-continued
Structures of potential mono-TAGs in CMTAG
| Compound | Structure |
|---|---|
| LLLn | 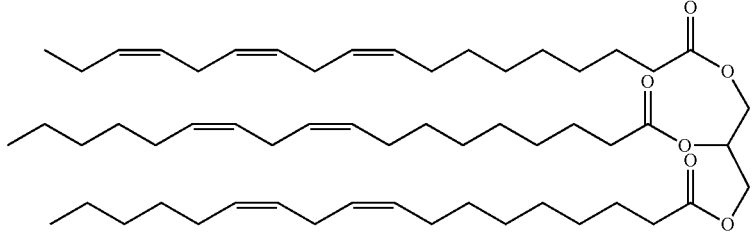 [SMILES: CC/C=C\C/C=C\C/C=C\CCCCCCCC(=O)OCC(COC(=O)CCCCCCC/C=C\C/C=C\CCCCC)OC(=O)CCCCCCC/C=C\C/C=C\CCCCC] |
| OLnLn | 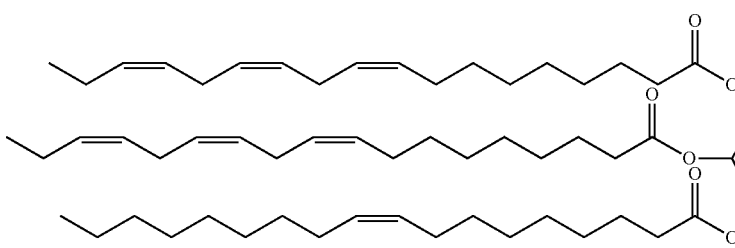 |
| OLnDd | 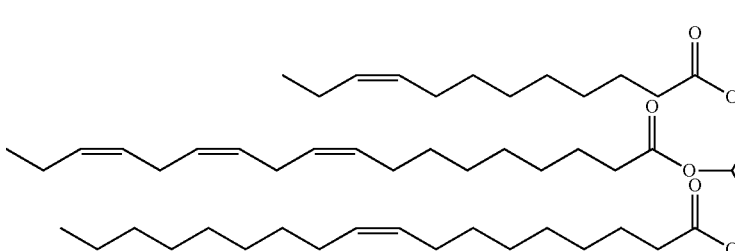 |
| OLnD | 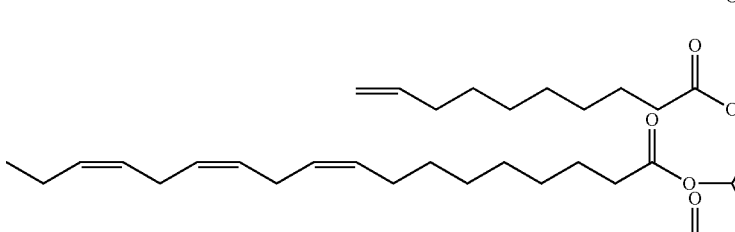 |
| DLnLn | 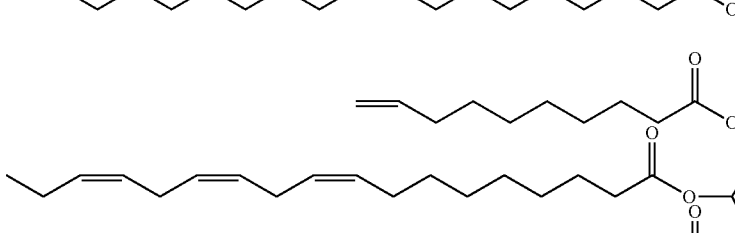 |
| DdLnLn | 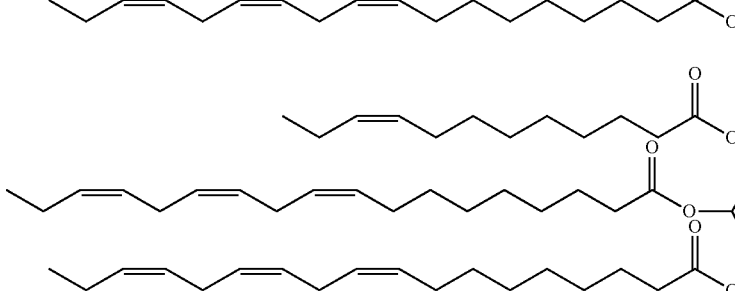 |

TABLE 4-continued
Structures of potential mono-TAGs in CMTAG
| Compound | Structure |
|---|---|
| LOLn | 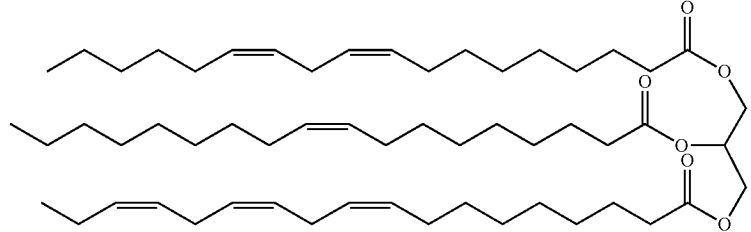 [SMILES: CC/C=C\C/C=C\C/C=C\CCCCCCCC(=O)OCC(COC(=O)CCCCCCC/C=C\C/C=C\CCCCC)OC(=O)CCCCCCC/C=C\CCCCCCCC] |
| LLL | 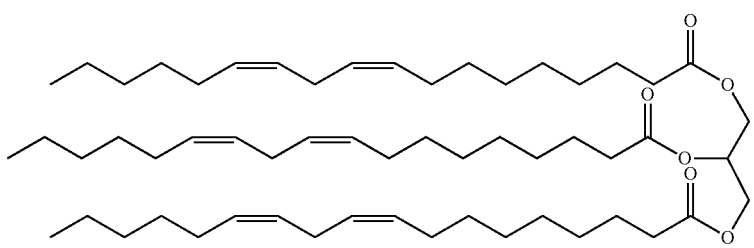 [SMILES: CCCCC/C=C\C/C=C\CCCCCCCC(=O)OCC(COC(=O)CCCCCCC/C=C\C/C=C\CCCCC)OC(=O)CCCCCCC/C=C\C/C=C\CCCCC] |
| LnOO | 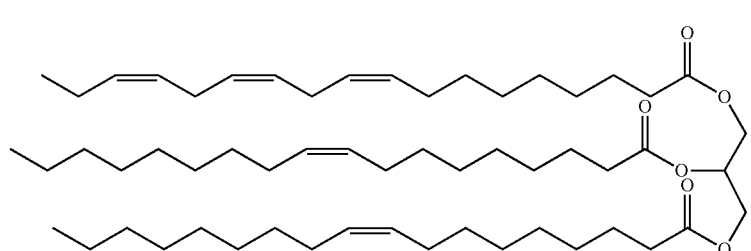 |
| DdOO | 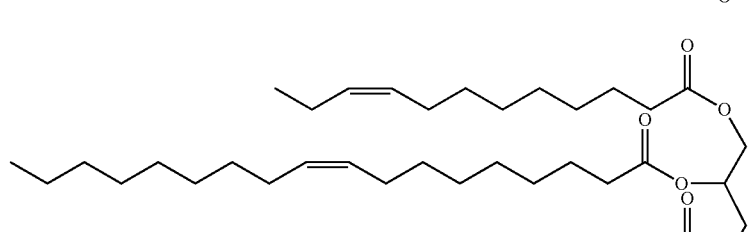 |
| DDdO | 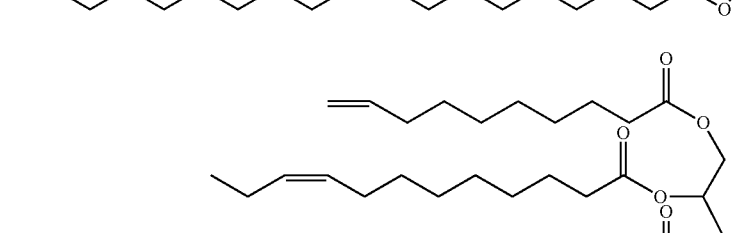 |
| LPLn | 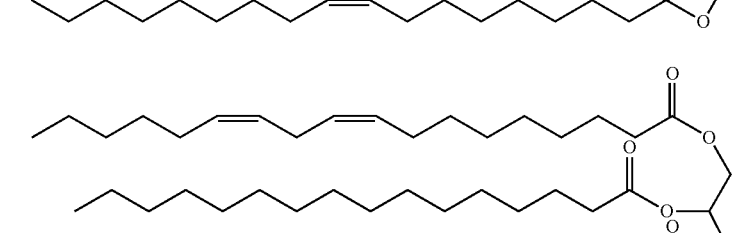 |

TABLE 4-continued
Structures of potential mono-TAGs in CMTAG
| Compound | Structure |
|---|---|
| DdPLn | 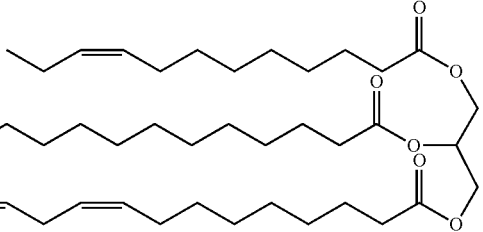 |
| DPLn | 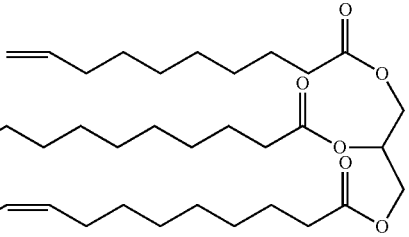 |
| DPDn | 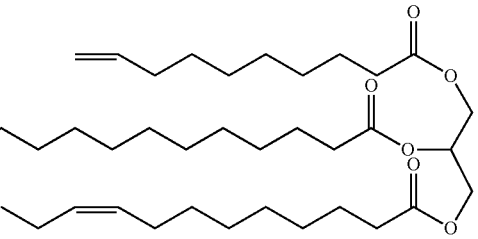 |
| DPD | 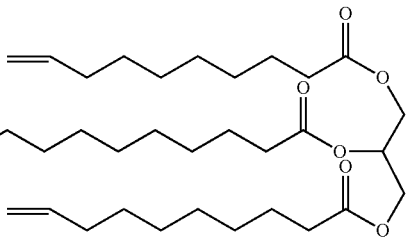 |
| DdPDd | 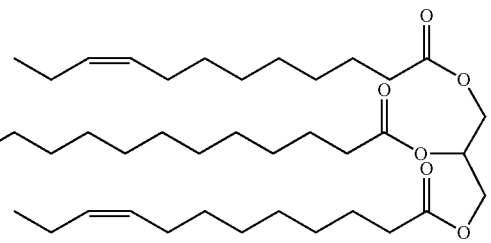 |
| LPDd | 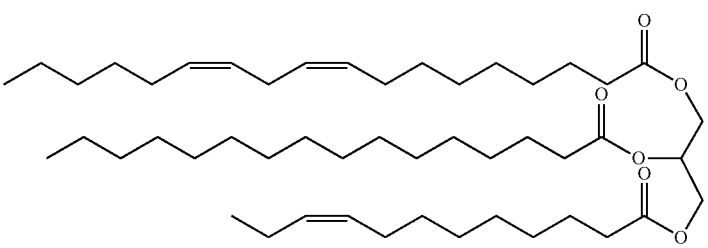 [SMILES: CC/C=C\CCCCCCCC(=O)OCC(COC(=O)CCCCCCC/C=C\C/C=C\CCCCC)OC(=O)CCCCCCCCCCCCCCC] |

TABLE 4-continued

Structures of potential mono-TAGs in CMTAG

| Compound | Structure |
|---|---|
| LPD | 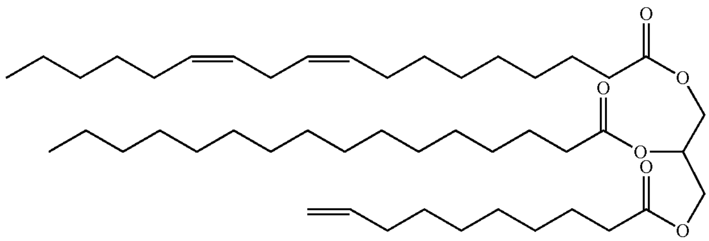 [SMILES: C=CCCCCCCCC(=O)OCC(COC(=O)CCCCCCC/C=C\C/C=C\CCCCC)OC(=O)CCCCCCCCCCCCCCC] |
| DdDdP | 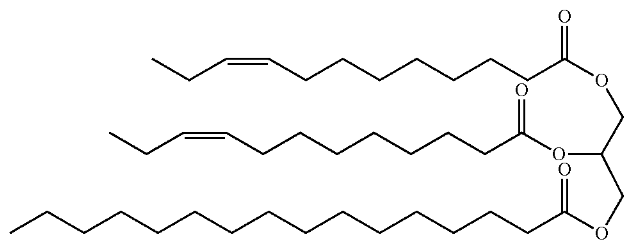 [SMILES: CC/C=C\CCCCCCCC(=O)OCC(COC(=O)CCCCCCCCCCCCCCC)OC(=O)CCCCCCC/C=C\CC] |
| DOP | 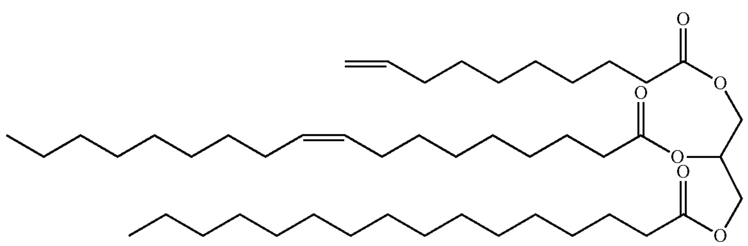 [SMILES: C=CCCCCCCCC(=O)OCC(COC(=O)CCCCCCCCCCCCCCC)OC(=O)CCCCCCC/C=C\CCCCCCCC] |
| DdOP | 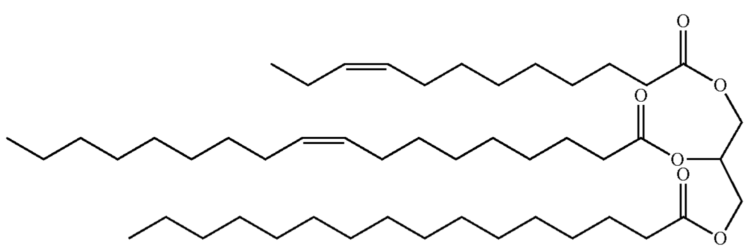 [SMILES: CC/C=C\CCCCCCCC(=O)OCC(COC(=O)CCCCCCCCCCCCCCC)OC(=O)CCCCCCC/C=C\CCCCCCCC] |
| LDP | 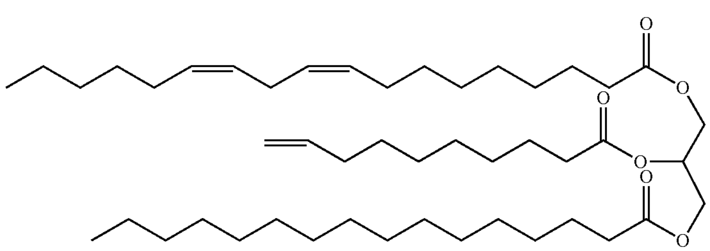 [SMILES: C=CCCCCCCCC(=O)OC(COC(=O)CCCCCCC/C=C\C/C=C\CCCCC)COC(=O)CCCCCCCCCCCCCCC] |
| PLL | 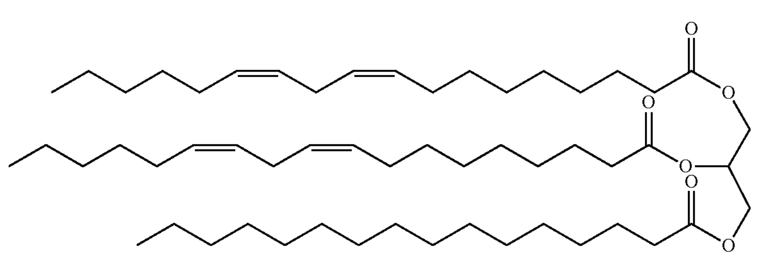 [SMILES: CCCCC/C=C\C/C=C\CCCCCCCC(=O)OCC(COC(=O)CCCCCCCCCCCCCCC)OC(=O)CCCCCCC/C=C\C/C=C\CCCCC] |

TABLE 4-continued

Structures of potential mono-TAGs in CMTAG

| Compound | Structure |
|---|---|
| SLnP | 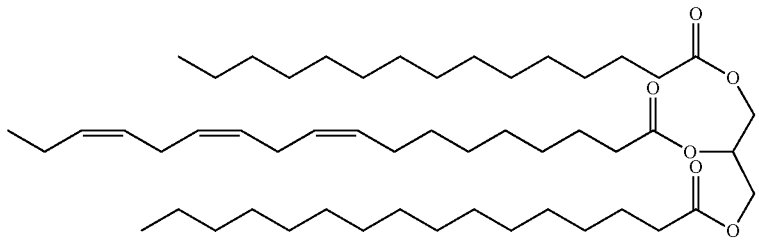 [SMILES: CC/C=C\C/C=C\C/C=C\CCCCCCCC(=O)OC(COC(=O)CCCCCCCCCCCCCC)COC(=O)CCCCCCCCCCCCCCC] |
| OPP | 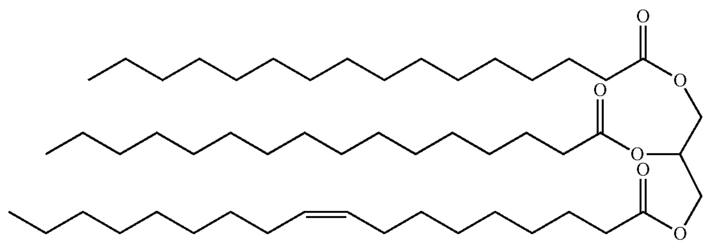 [SMILES: CCCCCCCC/C=C\CCCCCCCC(=O)OCC(COC(=O)CCCCCCCCCCCCCCC)OC(=O)CCCCCCCCCCCCCCC] |
| DdPP | 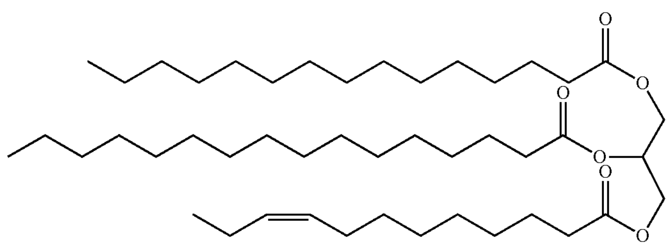 [SMILES: CC/C=C\CCCCCCCC(=O)OCC(COC(=O)CCCCCCCCCCCCCC)OC(=O)CCCCCCCCCCCCCCC] |
| DPP | 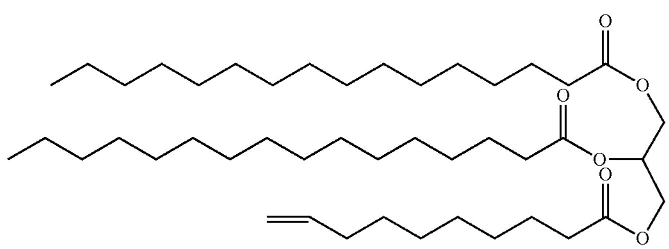 [SMILES: C=CCCCCCCCC(=O)OCC(COC(=O)CCCCCCCCCCCCCCC)OC(=O)CCCCCCCCCCCCCCC] |
| OOS | 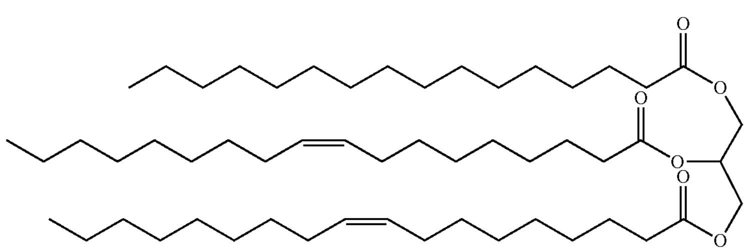 |
| PDD | 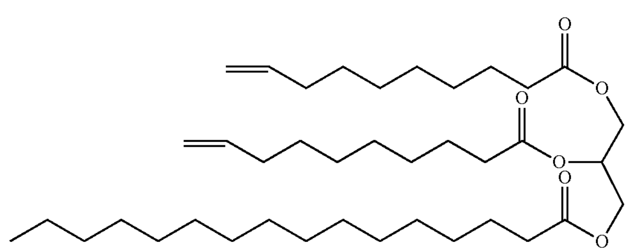 [SMILES: C=CCCCCCCCC(=O)OCC(COC(=O)CCCCCCCCCCCCCCC)OC(=O)CCCCCCCC=C] |

TABLE 4-continued

Structures of potential mono-TAGs in CMTAG

| Compound | Structure |
|---|---|
| PLD | 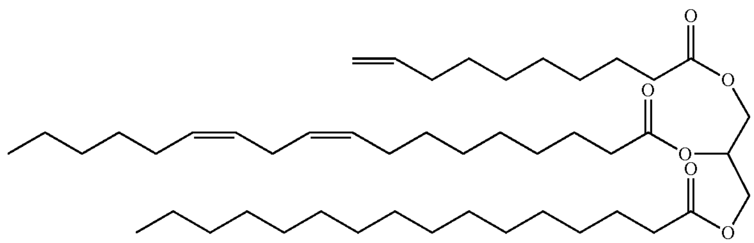 [SMILES: C=CCCCCCCCC(=O)OCC(COC(=O)CCCCCCCCCCCCCCC)OC(=O)CCCCCCC/C=C\C/C=C\CCCCC] |
| PDDd | 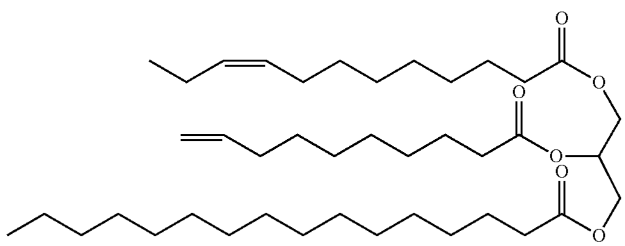 [SMILES: C=CCCCCCCCC(=O)OC(COC(=O)CCCCCCC/C=C\CC)COC(=O)CCCCCCCCCCCCCCC] |
| PLDd | 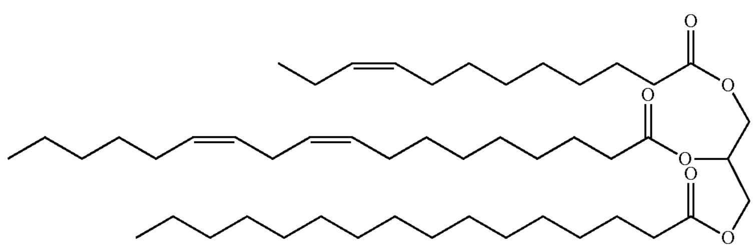 [SMILES: CC/C=C\CCCCCCCC(=O)OCC(COC(=O)CCCCCCCCCCCCCCC)OC(=O)CCCCCCC/C=C\C/C=C\CCCCC] |
| PDdDd | 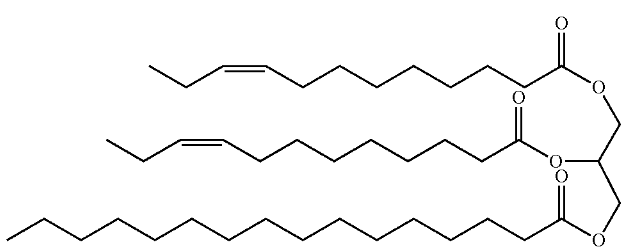 [SMILES: CC/C=C\CCCCCCCC(=O)OCC(COC(=O)CCCCCCCCCCCCCCC)OC(=O)CCCCCCC/C=C\CC] |
| POL | 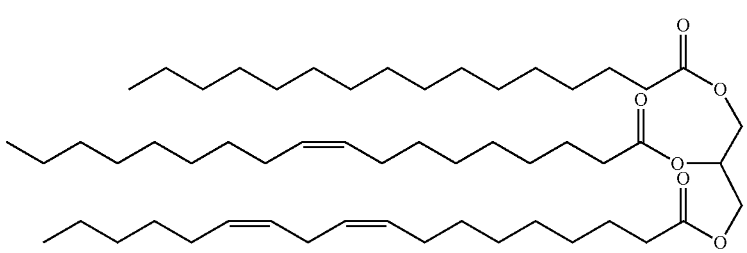 [SMILES: CCCCC/C=C\C/C=C\CCCCCCCC(=O)OCC(COC(=O)CCCCCCCCCCCCCCC)OC(=O)CCCCCCC/C=C\CCCCCCCC] |
| POO | 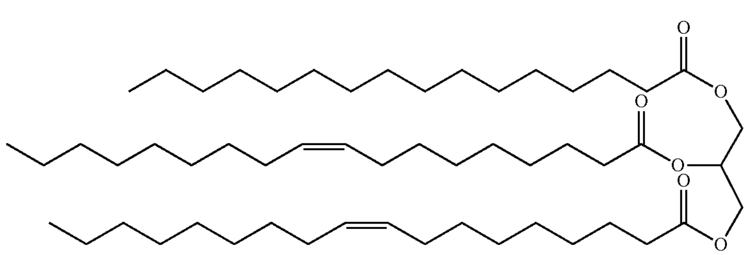 |

TABLE 4-continued

Structures of potential mono-TAGs in CMTAG

| Compound | Structure |
|---|---|
| POD | 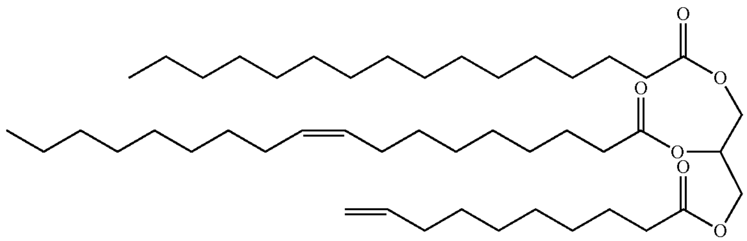 [SMILES: C=CCCCCCCCC(=O)OCC(COC(=O)CCCCCCCCCCCCCCC)OC(=O)CCCCCCC/C=C\CCCCCCCC] |
| PODd | 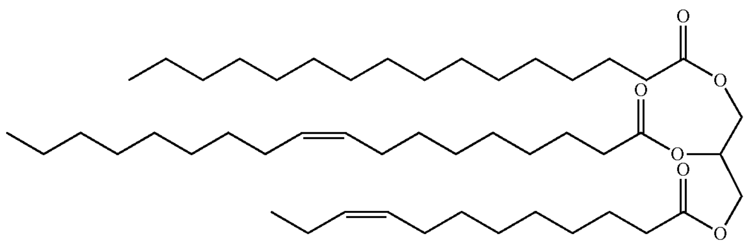 [SMILES: CC/C=C\CCCCCCCC(=O)OCC(COC(=O)CCCCCCCCCCCCCCC)OC(=O)CCCCCCC/C=C\CCCCCCCC] |
| SOO | 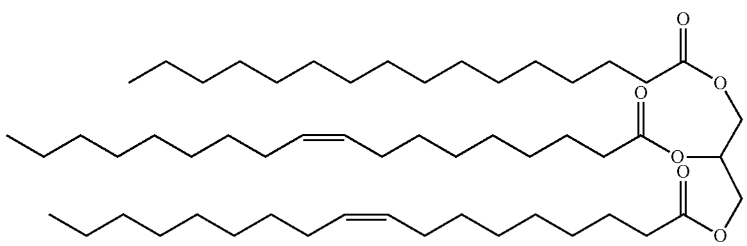 |
| SDD | 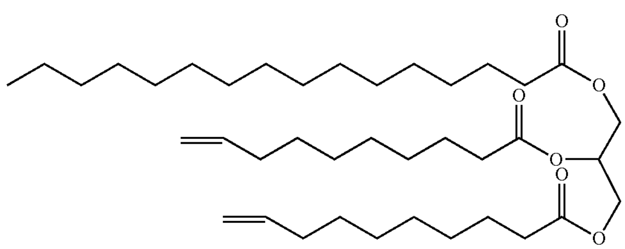 [SMILES: C=CCCCCCCCC(=O)OCC(COC(=O)CCCCCCCCCCCCCCC)OC(=O)CCCCCCCC=C] |
| SOD | 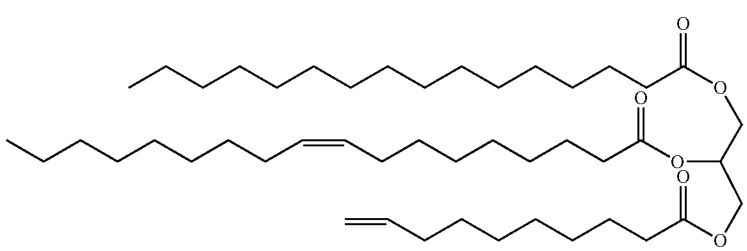 [SMILES: C=CCCCCCCCC(=O)OCC(COC(=O)CCCCCCCCCCCCCCC)OC(=O)CCCCCCC/C=C\CCCCCCCC] |
| SDDd | 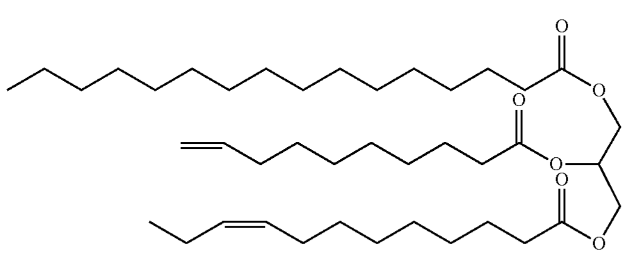 [SMILES: C=CCCCCCCCC(=O)OC(COC(=O)CCCCCCC/C=C\CC)COC(=O)CCCCCCCCCCCCCCC] |

TABLE 4-continued

Structures of potential mono-TAGs in CMTAG

| Compound | Structure |
|---|---|
| SODd | 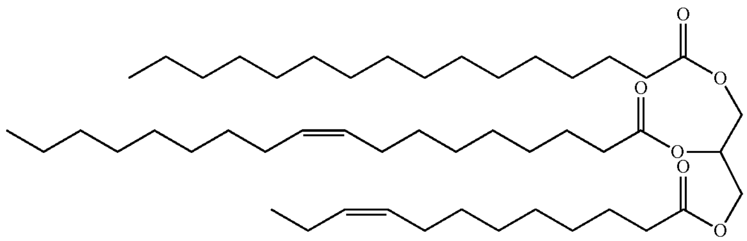 [SMILES: CC/C=C\CCCCCCCC(=O)OCC(COC(=O)CCCCCCCCCCCCCCC)OC(=O)CCCCCCC/C=C\CCCCCCCC] |
| SDdDd | 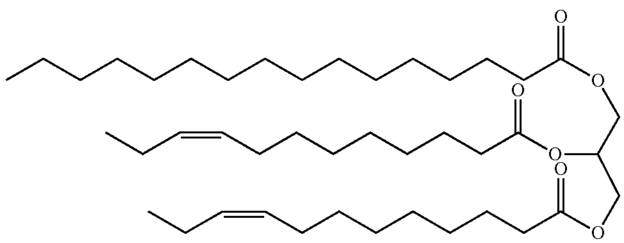 [SMILES: CC/C=C\CCCCCCCC(=O)OCC(COC(=O)CCCCCCCCCCCCCCC)OC(=O)CCCCCCC/C=C\CC] |
| PDS | 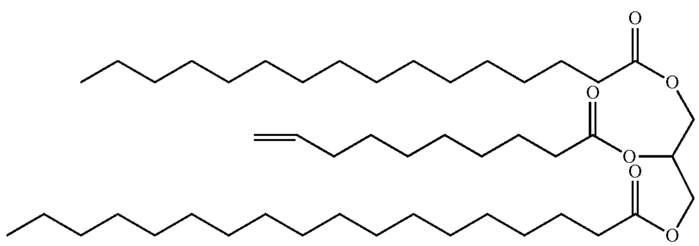 [SMILES: C=CCCCCCCCC(=O)OC(COC(=O)CCCCCCCCCCCCCCC)COC(=O)CCCCCCCCCCCCCCCCC] |
| PDdS | 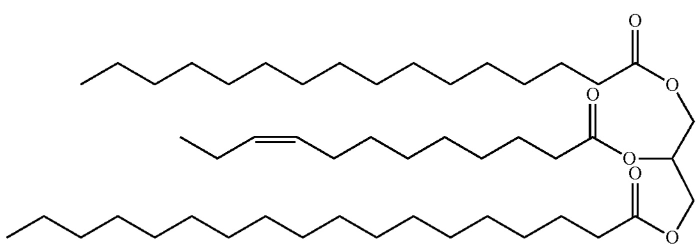 [SMILES: CC/C=C\CCCCCCCC(=O)OC(COC(=O)CCCCCCCCCCCCCCC)COC(=O)CCCCCCCCCCCCCCCCC] |

Fatty Acid and TAG Profile of CMTAG

Fatty acid profile was also determined using $^1$H-NMR data. Furthermore, CMTAG was fractionated by flash chromatography using ethyl acetate:hexanes=1:40 to 1:3 and its fraction analyzed with $^1$H-NMR and HPLC. TAG profile of CMTAG was investigated using HPLC.

Figure 1:
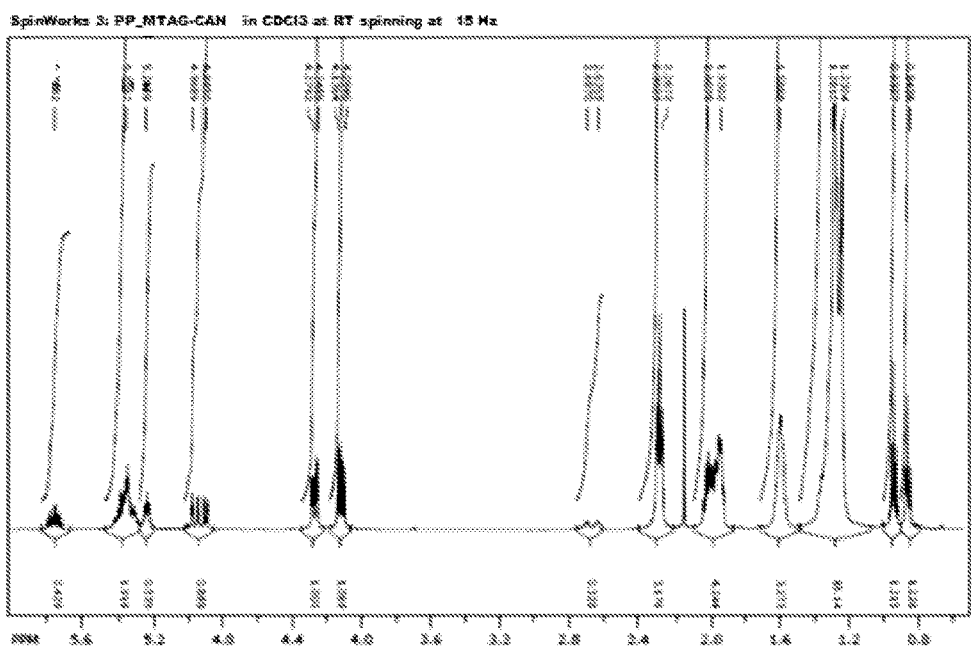
FIG. 1 depicts a $^1$H-NMR of canola oil MTAG.

$^1$H-NMR of CMTAG Results $^1$H-NMR spectrum of CMTAG is shown in FIG. 1. The protons of the glycerol skeleton, —CH$_2$CH(O)CH$_2$— and —OCH$_2$CHCH$_2$O— are clearly present at δ 5.3-5.2 ppm and 4.4-4.1 ppm, respectively. Two kinds of double bonds were detected: terminal double bond (n=0 in Scheme 3a), —CH═CH$_2$ and —CH═CH$_2$ present at δ 5.8 ppm and 5.0 to 4.9 ppm, respectively, and the internal double bond (n≠0 in Scheme 3a), —CH═CH— at δ 5.5 ppm to δ 5.3 ppm. The terminal/internal double bonds ratio as calculated by the relative integrals of their chemical shifts was ~1:2. The ester group —C(═O)CH$_2$— was present at δ 2.33-2.28 ppm, α-H to —CH═CH— at δ 2.03-1.98 ppm, and —C(═O)CH$_2$CH$_2$— at δ 1.60 ppm. Two kind of —CH$_3$ were detected, one with n=2 at 1.0-0.9 ppm and another with n=8 at 0.9-0.8 ppm, and their ratio is ~1:1. The signature chemical shift at 2.6-2.8 ppm of the proton between two double bonds in a polyunsaturated fatty acid was detected in the $^1$H-NMR of CMTAG, indicating the presence of polyunsaturated fatty acids. TAG oligomers were detected in the CMTAG by comparing the $^1$H-NMR integrated areas of the —CH$_3$ peaks and terminal double bond (i.e., —CH═CH$_2$ and —CH═CH$_2$) peaks with the glycerol skeleton. The fatty acid profile of CMTAG was calculated based on the relative area under the characteristic chemical shift peaks. The results are listed in Table 5. Due to the very low content of free fatty acid in the CMTAG material, the analysis was performed assuming that only TAG structures were present in the CMTAG.

TABLE 5

Fatty acid profile of CMTAG calculated based on the relative area under the characteristic $^1$H-NMR peaks

| Fatty Acids with: | Content (mol %) |
|---|---|
| —CH=CH$_2$ | 28.0 |
| Diacid in oligomers | 20.7 |
| —CH=CHCH$_2$CH$_3$ | 15.0 |
| —CH=CH(CH$_2$)$_7$CH$_3$ and/or CH=CH(CH$_2$)CH=CH(CH$_2$)$_4$CH$_3$ | 15.3 |
| Polyunsaturated fatty acid | 10.3 |
| Saturated fatty acid | 10.6 |

HPLC of CMTAG Results

Figure 2:
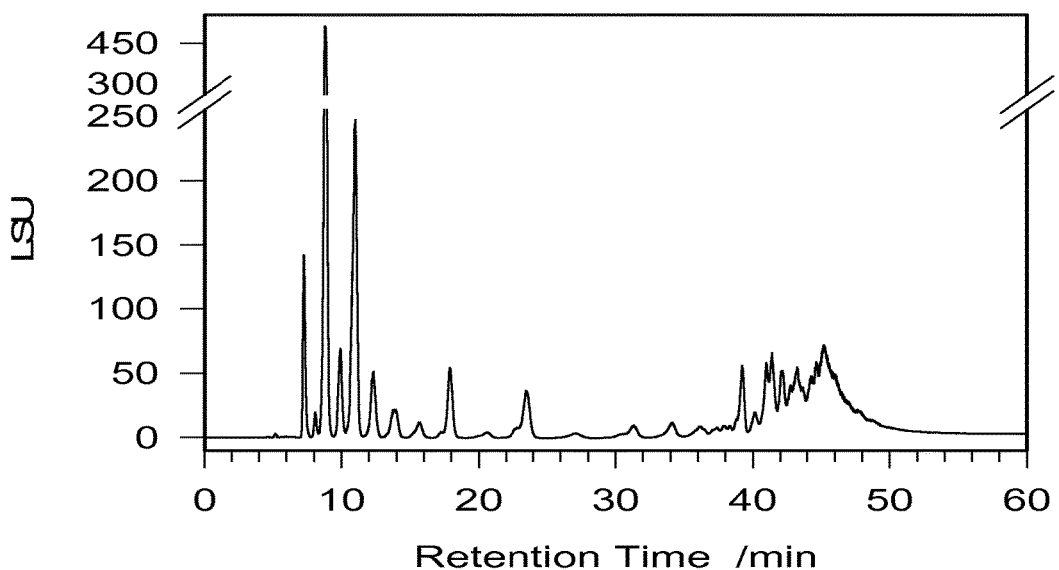
FIG. 2 depicts a HPLC of canola oil MTAG.
Figure 3:
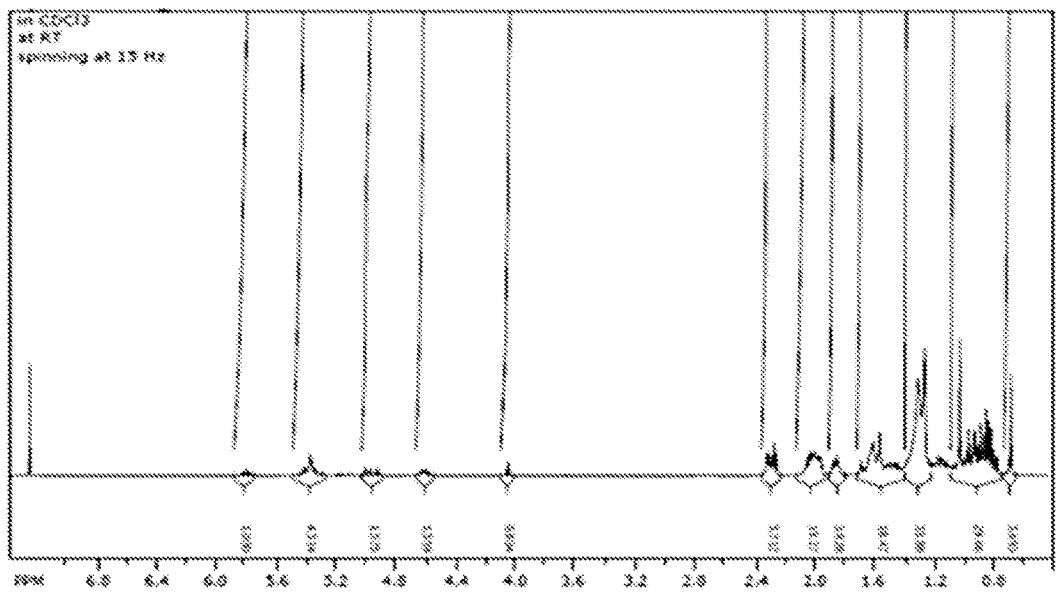
FIG. 3 depicts a $^1$H-NMR of Fraction 1 of canola oil MTAG.
Figure 4:
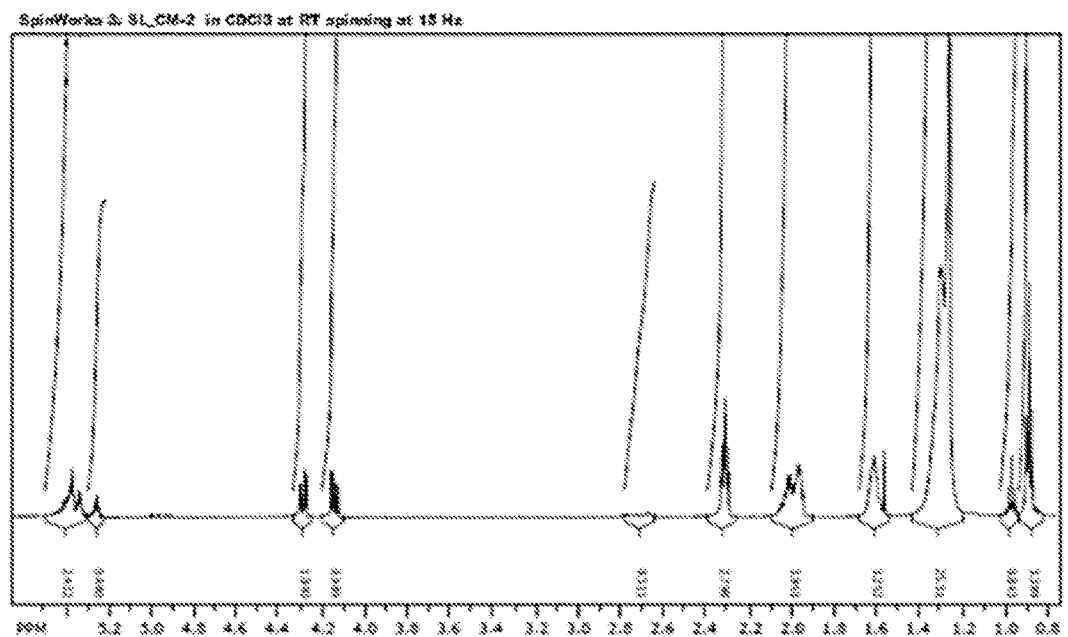
FIG. 4 depicts a $^1$H-NMR of Fraction 2 of canola oil MTAG.
Figure 5:
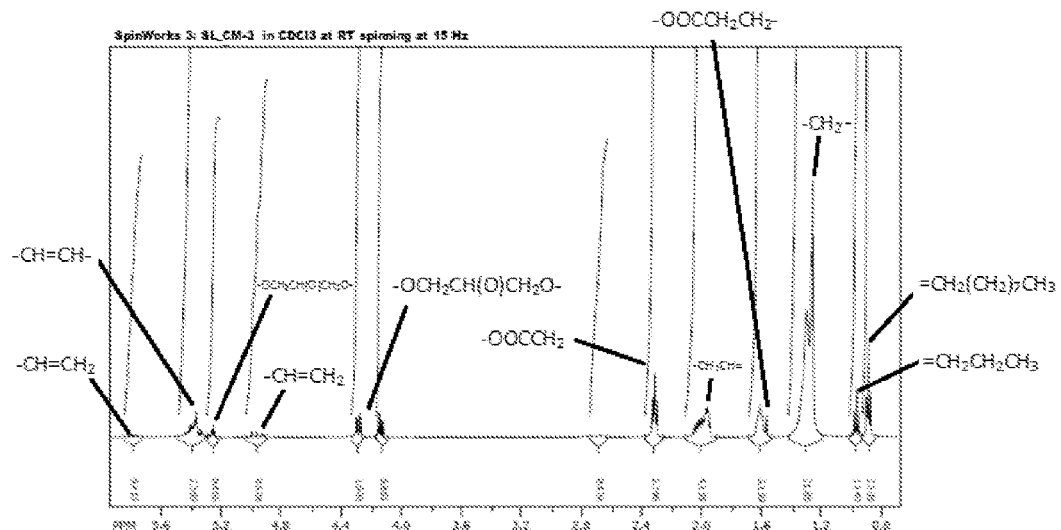
FIG. 5 depicts a $^1$H-NMR of Fraction 3 of canola oil MTAG.
Figure 6:
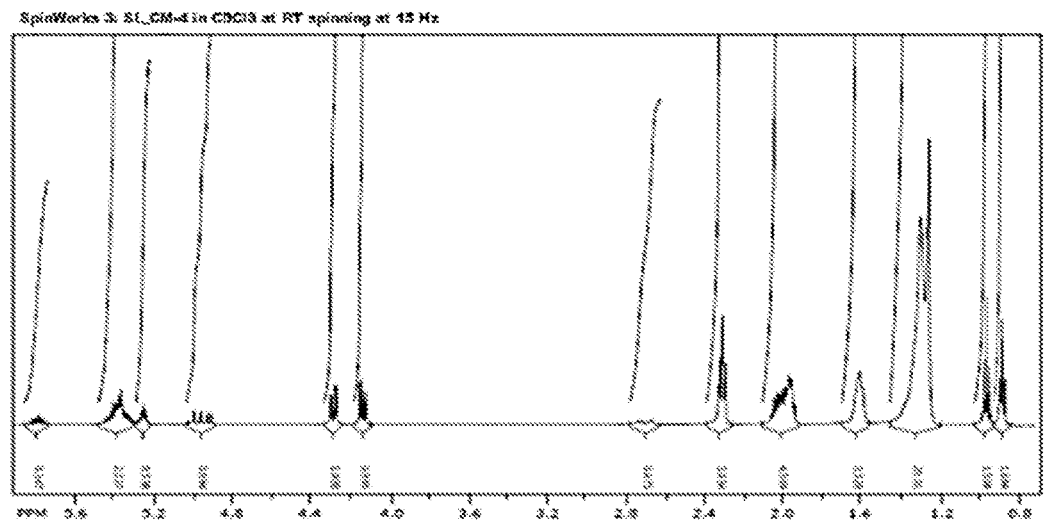
FIG. 6 depicts a $^1$H-NMR of Fraction 4 of canola oil MTAG.
Figure 7:
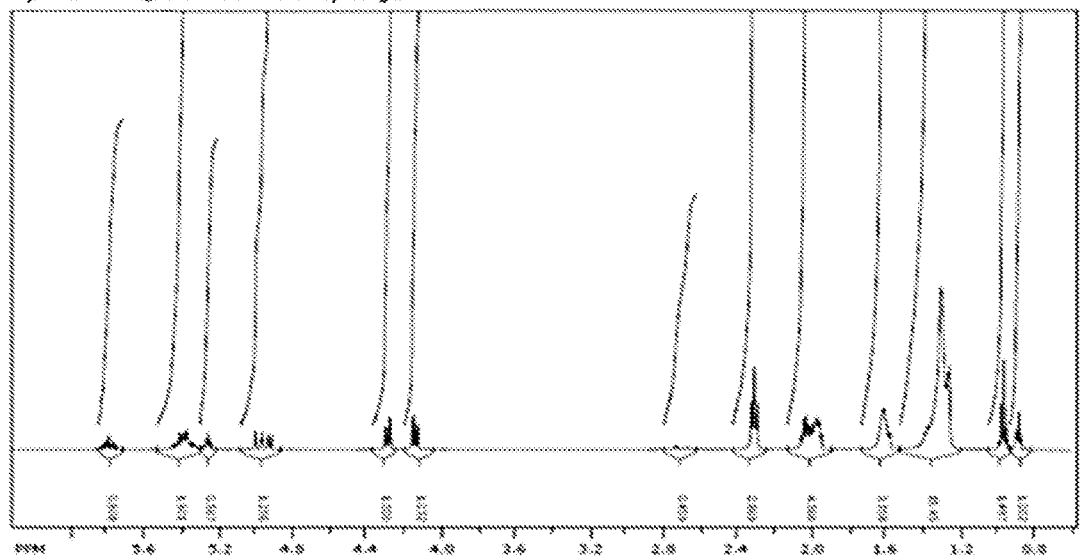
FIG. 7 depicts a $^1$H-NMR of Fraction 5 of canola oil MTAG.
Figure 8:
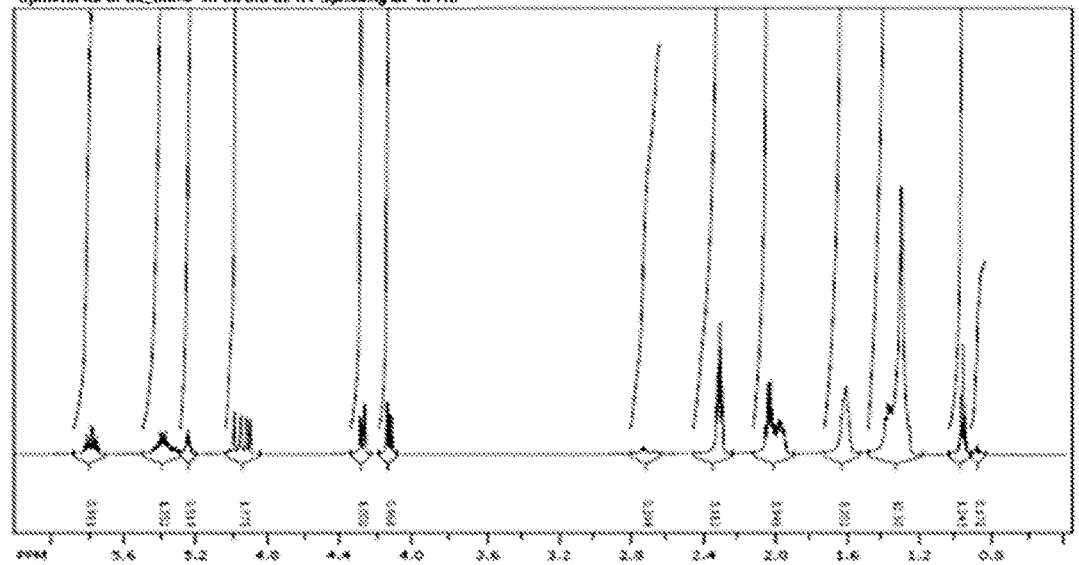
FIG. 8 depicts a $^1$H-NMR of Fraction 6 of canola oil MTAG.
Figure 9:
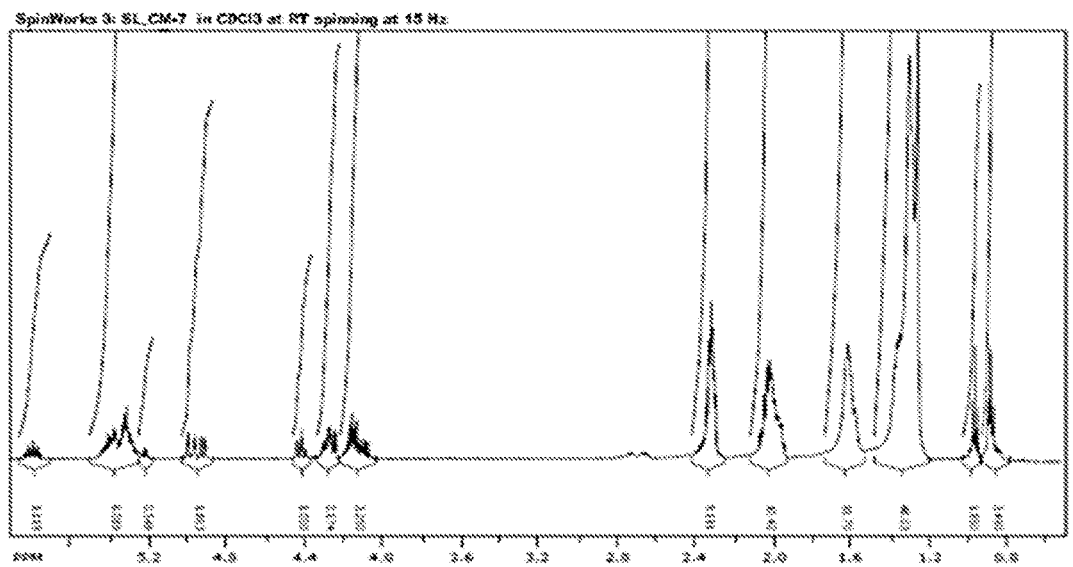
FIG. 9 depicts a $^1$H-NMR of Fraction 7 of canola oil MTAG.
Figure 10:
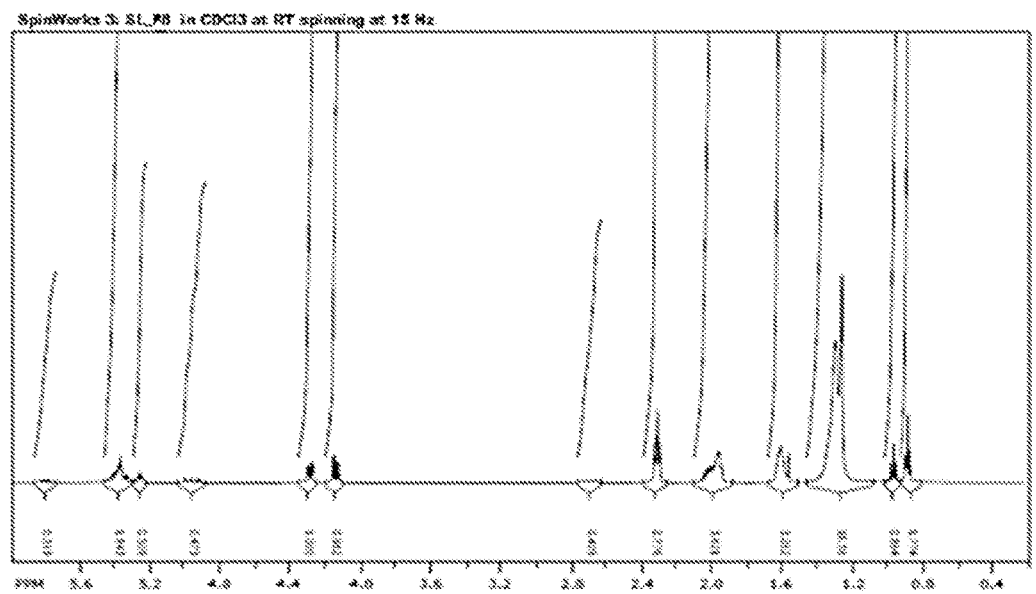
FIG. 10 depicts a $^1$H-NMR of Fraction 8 of canola oil MTAG.
Figure 11:
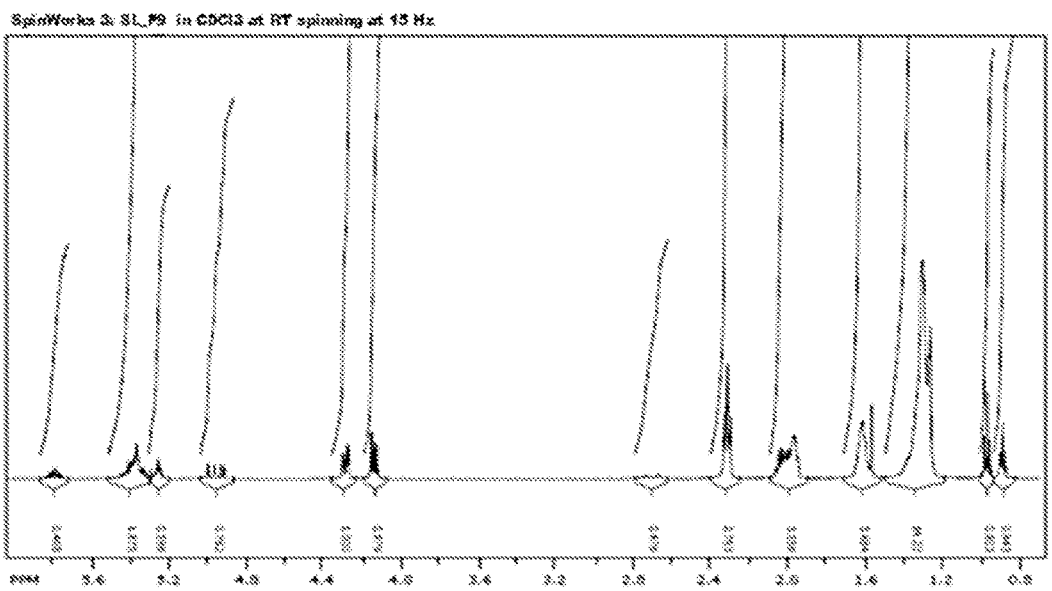
FIG. 11 depicts a $^1$H-NMR of Fraction 9 of canola oil MTAG.
Figure 12:
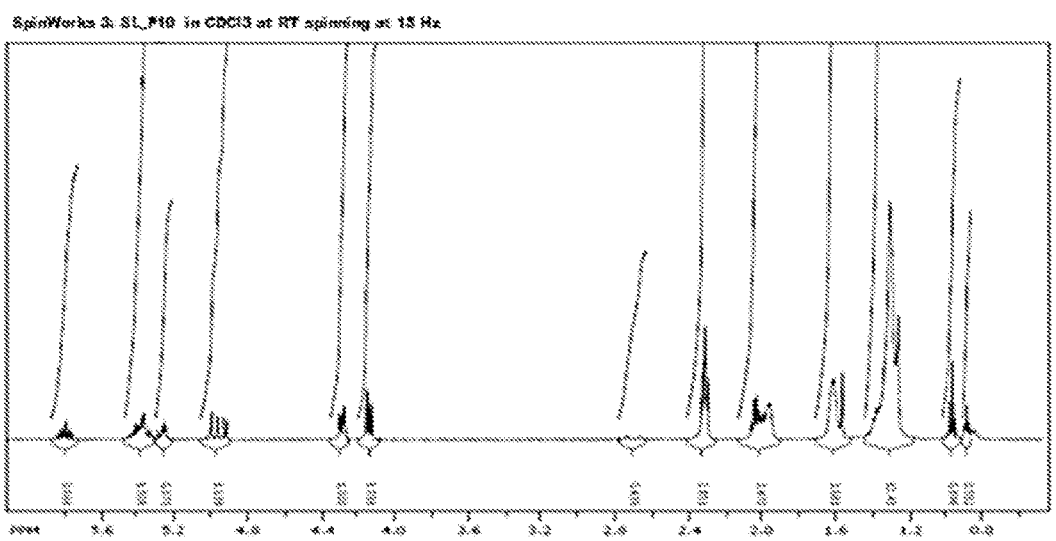
FIG. 12 depicts a $^1$H-NMR of Fraction 10 of canola oil MTAG.
Figure 13:
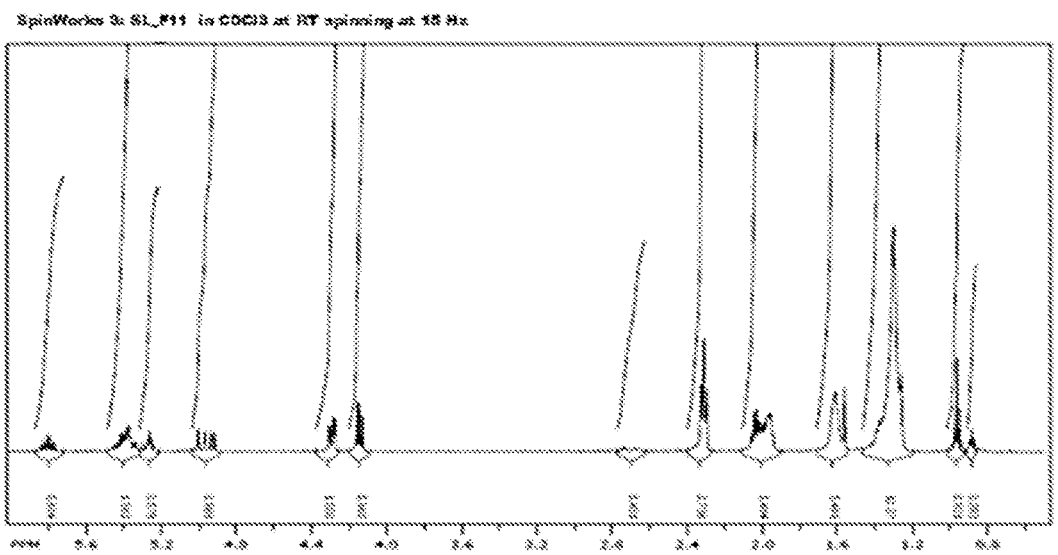
FIG. 13 depicts a $^1$H-NMR of Fraction 11 of canola oil MTAG.
Figure 14:
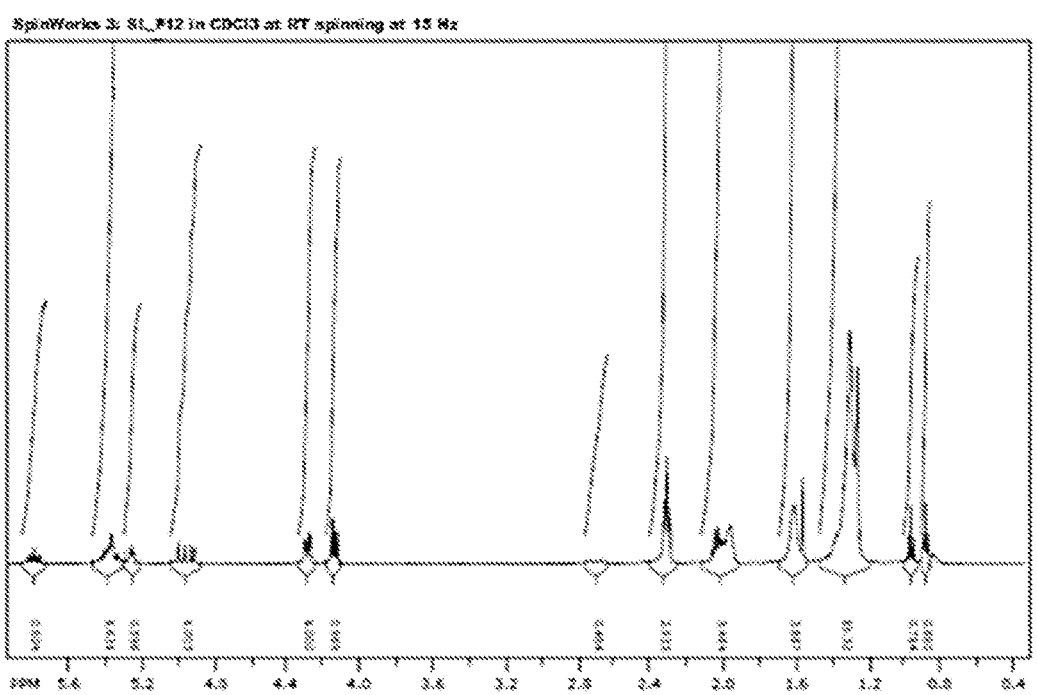
FIG. 14 depicts a $^1$H-NMR of Fraction 12 of canola oil MTAG.
Figure 15:
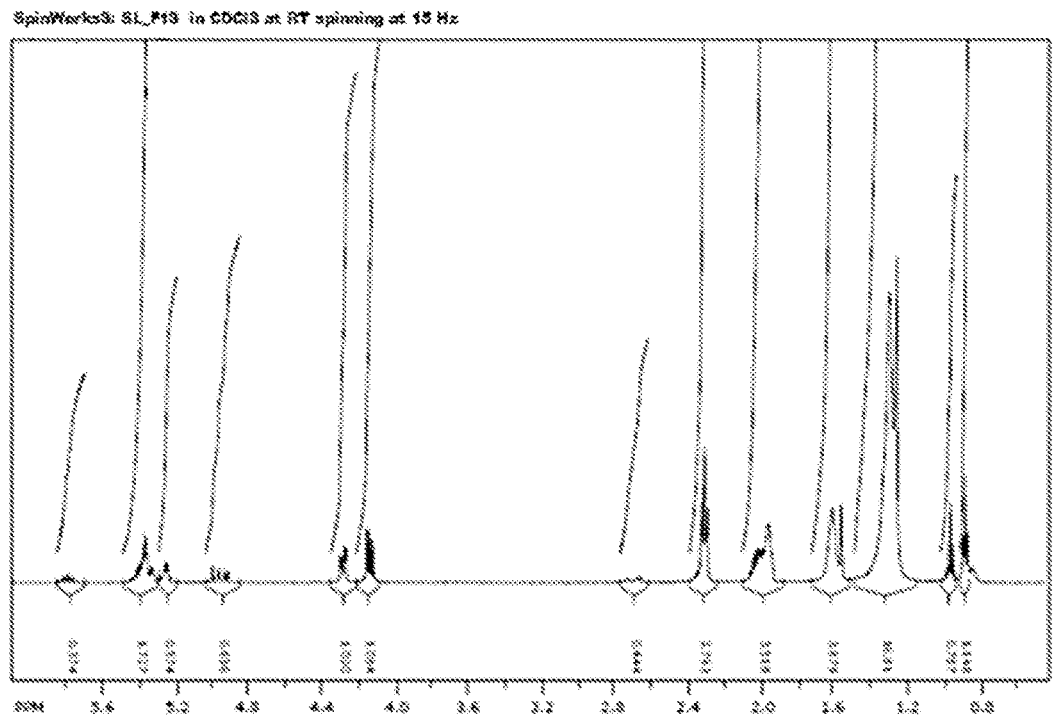
FIG. 15 depicts a $^1$H-NMR of Fraction 13 of canola oil MTAG.
Figure 16:
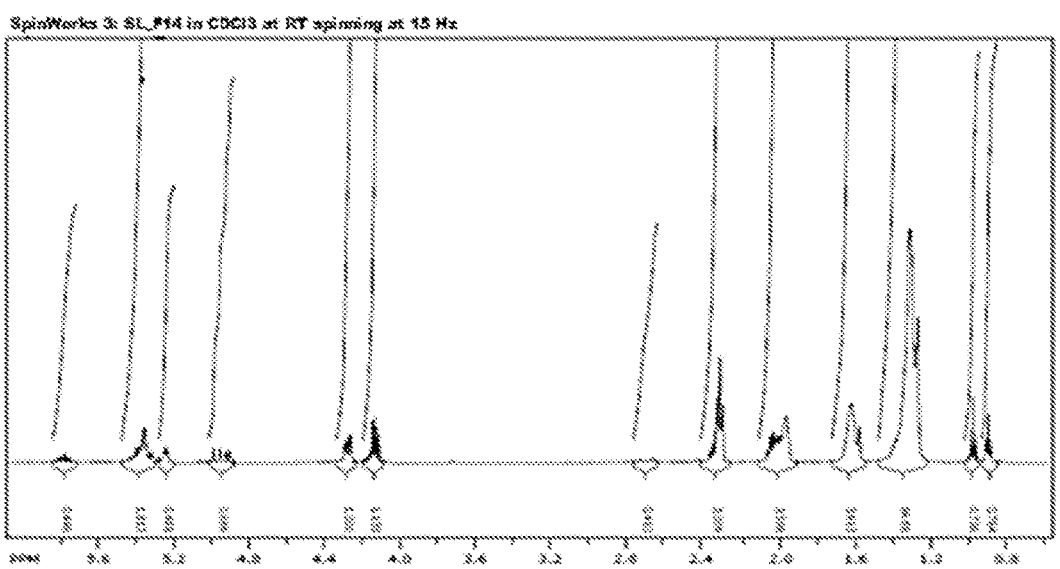
FIG. 16 depicts a $^1$H-NMR of Fraction 14 of canola oil MTAG.
Figure 17:
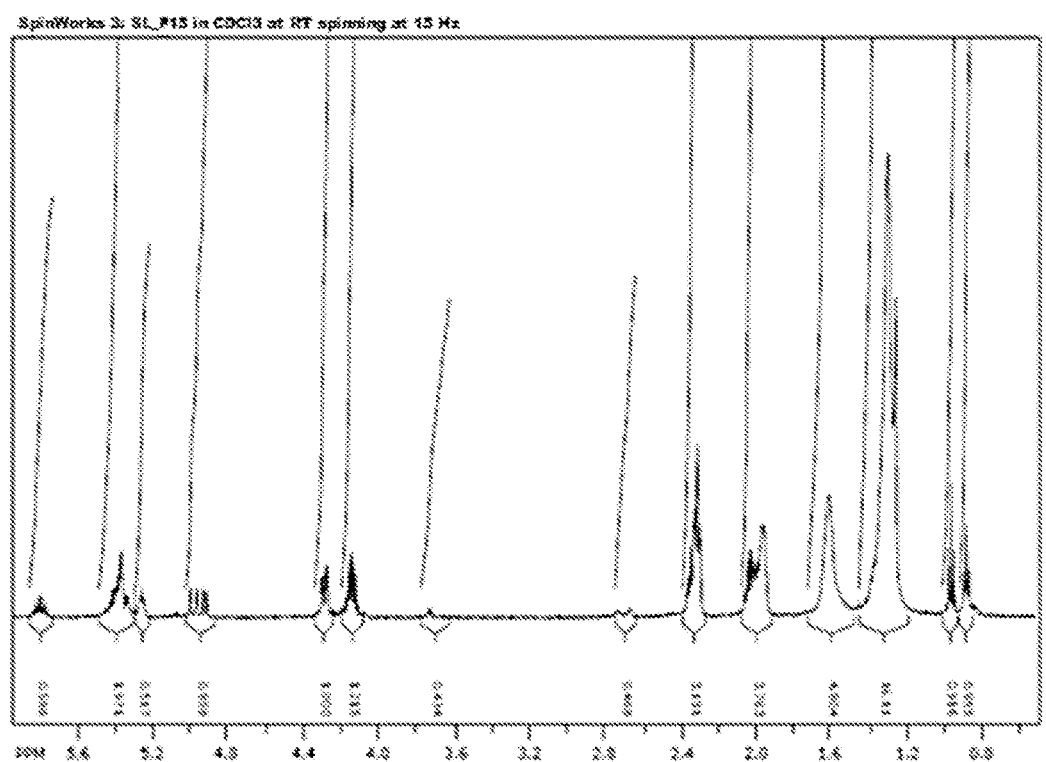
FIG. 17 depicts a $^1$H-NMR of Fraction 15 of canola oil MTAG.

The HPLC curve recorded using the slow method described in the analytical methods section is shown in FIG. 2. As shown, an excellent separation was obtained. The results of the HPLC analysis are reported in Table 6.

Two main groups of well-separated peaks were obtained. The first group of peaks between 0 and 30 min is associated with the polar compounds of the CMTAG, and the second group of peaks between 30 and 60 min is associated with low-polar compounds of the CMTAG. Note that HPLC analysis of the fractions of CMTAG (see section below) revealed that the first group of HPLC peak is associated with monomers and dimers with longer fatty acids, and the second with dimers with shorter fatty acids and trimers and higher oligomers. Note that oxidized TAGs and/or higher oligomers may be present in very small amounts.

TABLE 6

HPLC analysis data of CMTAG

| Peak | Retention time (min) | Area % |
|---|---|---|
| 1 | 7.26 | 3.84 |
| 2 | 8.08 | 0.50 |
| 3 | 8.80 | 19.21 |
| 4 | 9.91 | 3.05 |
| 5 | 11.0 | 13.47 |
| 6 | 12.33 | 3.01 |
| 7 | 13.82 | 1.00 |
| 8 | 13.91 | 0.89 |
| 9 | 15.70 | 1.01 |
| 10 | 17.27 | 0.24 |
| 11 | 17.90 | 3.28 |
| 12 | 20.63 | 0.29 |
| 13 | 22.54 | 0.14 |
| 14 | 22.85 | 0.30 |
| 15 | 27.12 | 0.38 |
| 16 | 31.33 | 1.00 |
| 17 | 34.14 | 0.89 |
| 18 | 36.09 | 0.38 |
| 18 | 37.88 | 0.24 |
| 20 | 38.30 | 0.16 |
| 21 | 38.76 | 0.19 |
| 22 | 39.20 | 2.67 |
| 23 | 40.13 | 0.93 |
| 24 | 40.98 | 2.91 |
| 25 | 41.38 | 3.36 |
| 26 | 42.15 | 3.15 |
| 27 | 43.21 | 7.02 |
| 28 | 44 to 50 | 21.45 |

Fractionation of CMTAG by Column Chromatography

CMTAG was fractionated by flash chromatography using ethyl acetate:hexanes=1:40 to 1:3. Fifteen (15) fractions (F1 to F15) were collected and characterized by $^1$H-NMR and HPLC.

$^1$HNMR of CMTAG Fractions

The $^1$H-NMR spectra of fractions F1 to F15 are shown in FIG. 3 to FIG. 17, respectively. The corresponding $^1$H-NMR data are listed in Table 7.

TABLE 7

$^1$H-NMR chemical shifts, δ, of CMTAG Polyol fractions

| Fraction | $^1$H-NMR Chemical shifts, δ, in CDCl$_3$ (ppm) |
|---|---|
| 1 | 5.8 (1, m), 5.4 (4, m), 5.0 (2, m), 4.6 (2, m), 4.0 (1, t), 2.3 (6, m), 2.0 (10, m), 1.8 (4, m), 1.6-1.4 (18, m), 1.4-1.2 (33, m), 1.0-0.8 (30, m) |
| 2 | 5.4 (4, m), 5.3-5.2 (1, m), 4.3 (2, dd), 4.1 (2, dd), 2.8-2.6 (1, m), 2.3 (6, t), 2.0 (8, m), 1.6 (6, m), 1.3 (50, m), 1.0 (1.8, t), 0.8 (6.2, t) |
| 3 | 5.8 (0.5, m), 5.4 (4, m), 5.3-5.2 (1, m), 5.0 (1, m), 4.3 (2, dd), 4.1 (2, dd), 2.8-2.6 (0.8, m), 2.3 (6, t), 2.0 (8, m), 1.6 (6, m), 1.3 (44, m), 1.0 (2, t), 0.8 (5, t) |
| 4 | 5.8 (0.7, m), 5.4 (4, m), 5.3-5.2 (1, m), 5.0 (1.4, m), 4.3 (2, dd), 4.1 (2, dd), 2.8-2.6 (1, m), 2.3 (6, t), 2.0 (9, m), 1.6 (6, m), 1.3 (40, m), 1.0 (3, t), 0.8 (3.4, t) |
| 5 | 5.8 (1.2, m), 5.4 (4, m), 5.3-5.2 (1, m), 5.0 (2.4, m), 4.3 (2, dd), 4.1 (2, dd), 2.8-2.6 (0.9, m), 2.3 (6, t), 2.0 (8, m), 1.6 (6, m), 1.3 (30, m), 1.0 (3, t), 0.8 (2, t) |
| 6 | 5.8 (1.8, m), 5.4 (2.7, m), 5.3-5.2 (1, m), 5.0 (3.4, m), 4.3 (2, dd), 4.1 (2, dd), 2.8-2.6 (0.8, m), 2.3 (6, t), 2.0 (8, m), 1.6 (6, m), 1.3 (24, m), 1.0 (2.4, t), 0.8 (0.3, t) |
| 7 | 5.8 (2, m), 5.4 (12, m), 5.0 (3.6, m), 4.3 (2, dd), 4.3-4.3 (4, m), 4.2-4.0 (6, m), 2.3 (18, t), 2.0 (20, m), 1.6 (22, m), 1.3 (76, m), 1.0 (2, t), 0.8 (7, t) |
| 8 | 5.8 (0.5, m), 5.4 (4, m), 5.3-5.2 (1, m), 5.0 (1, m), 4.3 (2, dd), 4.1 (2, dd), 2.8-2.6 (0.8, m), 2.3 (6, t), 2.0 (7, m), 1.6 (6, m), 1.3 (36, m), 1.0 (1.6, t), 0.8 (3.6, t) |
| 9 | 5.8 (0.8, m), 5.4 (3.8, m), 5.3-5.2 (1, m), 5.0 (1.6, m), 4.3 (2, dd), 4.1 (2, dd), 2.8-2.6 (1, m), 2.3 (6, t), 2.0 (7, m), 1.6 (6, m), 1.3 (28, m), 1.0 (1.8, t), 0.8 (1.8, t) |
| 10 | 5.8 (1.1, m), 5.4 (3.0, m), 5.3-5.2 (1, m), 5.0 (2.2, m), 4.3 (2, dd), 4.1 (2, dd), 2.8-2.6 (0.8, m), 2.3 (6, t), 2.0 (7, m), 1.6 (8, m), 1.3 (26, m), 1.0 (1.8, t), 0.8 (1, t) |
| 11 | 5.8 (1, m), 5.4 (3.0, m), 5.3-5.2 (1, m), 5.0 (2, m), 4.3 (2, dd), 4.1 (2, dd), 2.8-2.6 (0.8, m), 2.3 (6, t), 2.0 (7, m), 1.6 (7, m), 1.3 (24, m), 1.0 (1.8, t), 0.8 (0.8, t) |
| 12 | 5.8 (1, m), 5.4 (3.2, m), 5.3-5.2 (1, m), 5.0 (2, m), 4.3 (2, dd), 4.1 (2, dd), 2.8-2.6 (0.9, m), 2.3 (6, t), 2.0 (7, m), 1.6 (8, m), 1.3 (30, m), 1.0 (1.4, t), 0.8 (1.8, t) |
| 13 | 5.8 (1, m), 5.4 (3.2, m), 5.3-5.2 (1, m), 5.0 (2, m), 4.3 (2, dd), 4.1 (2, dd), 2.8-2.6 (0.9, m), 2.3 (6, t), 2.0 (7, m), 1.6 (8, m), 1.3 (30, m), 1.0 (1.4, t), 0.8 (1.8, t) |
| 14 | 5.8 (0.7, m), 5.4 (3.6, m), 5.3-5.2 (1, m), 5.0 (1.3, m), 4.3 (2, dd), 4.1 (2, dd), 2.8-2.6 (0.8, m), 2.3 (6, t), 2.0 (7, m), 1.6 (7.2, m), 1.3 (30, m), 1.0 (1.4, t), 0.8 (1.6, t) |
| 15 | 5.8 (1, m), 5.4 (4, m), 5.3-5.2 (1, m), 5.0 (2, m), 4.3 (2, dd), 4.1 (2, dd), 2.7 (0.8, d), 2.8-2.6 (0.9, m), 2.3 (6, t), 2.0 (7, m), 1.6 (10, m), 1.3 (32, m), 1.0 (1.8, t), 0.8 (2, t) |

Analysis of $^1$H-NMR of CMTAG Fractions

The analysis of $^1$H-NMR shifts of the double bond structures in the fractions of CMTAG revealed the presence of terminal or/and internal double bonds of oleic (DB1), Linoleic (DB2), myristoleic (DB3) and decenoic (DB4) moieties with varying relative amounts, as well as saturated fatty acids in monomer, dimer and trimer TAG structures. The double bond structures and corresponding molar ratios in the different fractions of CMTAG are presented in Table 8a and corresponding structures in Table 8b.

$^1$H-NMR indicates that F2, F3, F4, F5 and F6 are composed of TAG monomers, F8, F9, F10 and F11 are composed of TAG dimers, and F13 and F14 are composed of TAG trimers. F1 is composed of olefins, F12 is a mixture of TAG dimers and trimers and F7 is composed of non-typical TAG structures. The flush fraction (F15) showed $^1$H-NMR shifts that are associated with oxidized compounds and higher level oligomers. As estimated from the mass of the collected fractions, the monomers, dimers and trimers accounts for 40%, 30 to 40% and less than 10% of the total mass of CMTAG, respectively.

TABLE 8a

Double bond structures of CMTAG fractions and corresponding calculated molar ratios from $^1$H-NMR data. EA:HE is the ethyl acetate:hexanes ratio. DB1, DB2, DB3 and DB4: types of double bonds detected by $^1$H-NMR and presented in Table 8b.

| Fraction | EA:HE | $^a$Structures | Type of Compound | Yield |
|---|---|---|---|---|
| F1 | 1:40 | | Olefin | |
| F2 | 1:40 | Without DB4; With DB1, DB2 and DB3 DB3/(DB2 + DB1) = 0.83/3.39 = 0.25 | TAG Monomers | Monomers: >40% |
| F3 | 1:40 | With DB1, DB2, DB3 and DB4 DB3/(DB2 + DB1) = 1.15/2.50 = 0.46 DB4/(DB1 + DB2 + DB3) = 0.53/2.39 = 0.22 | TAG Monomers | |
| F4 | 1:40 | With DB1, DB2, DB3 and DB4 DB3/(DB2 + DB1) = 1.51/1.68 = 0.89 DB4/(DB1 + DB2 + DB3) = 0.69/2.24 = 0.31 | TAG Monomers | |
| F5 | 1:40 | With DB1, DB2, DB3 and DB4 DB3/(DB2 + DB1) = 1.50/1.00 = 1.5 DB4/(DB1 + DB2 + DB3) = 1.26/1.90 = 0.66 | TAG Monomers | |
| F6 | 1:40 | With DB2, DB3 and DB4 DB4/(DB2 + DB3) = 1.78/1.35 = 1.32 | TAG Monomers | |
| F7 | 1:40 | With DB1, DB2, DB3 and DB4 | Not typical TAG structures | |
| F8 | 1:30 | With DB1, DB2, DB3 and DB4 DB3/(DB2 + DB1) = 0.86/1.77 = 0.49 DB4/(DB1 + DB2 + DB3) = 0.47/1.94 = 0.24 | TAG Dimers | Dimers: ~30-40% |
| F9 | 1:30 | With DB1, DB2, DB3 and DB4 DB3/(DB2 + DB1) = 0.90/0.94 = 0.96 DB4/(DB1 + DB2 + DB3) = 0.79/1.88 = 0.42 | TAG Dimers | |
| F10 | 1:20 | With DB1, DB2, DB3 and DB4 DB3/(DB2 + DB1) = 0.90/0.55 = 1.64 DB4/(DB1 + DB2 + DB3) = 1.14/1.51 = 0.75 | TAG Dimers | |
| F11 | 1:20 | With DB1, DB2, DB3 and DB4 DB3/(DB2 + DB1) = 0.90/0.39 = 2.31 DB4/(DB1 + DB2 + DB3) = 0.99/1.56 = 0.63 | TAG Dimers | |
| F12 | 1:10 | With DB1, DB2, DB3 and DB4 DB3/(DB2 + DB1) = 0.71/0.86 = 0.83 DB4/(DB1 + DB2 + DB3) = 1.0/1.63 = 0.61 | Mixture of TAG Dimers and Trimers | |
| F13 | 1:10 | With DB1, DB2, DB3 and DB4 DB3/(DB2 + DB1) = 0.71/1.15 = 0.62 DB4/(DB1 + DB2 + DB3) = 0.66/1.73 = 0.38 | TAG Trimers | Trimers: <10% |
| F14 | 1:10 | With DB1, DB2, DB3 and DB4 DB3/(DB2 + DB1) = 0.74/0.76 = 0.97 DB4/(DB1 + DB2 + DB3) = 0.69/1.81 = 0.38 | TAG Trimers | |
| F15 | 1:5 to 1:3 | With DB1, DB2, DB3 and DB4 DB3/(DB2 + DB1) = 0.92/0.95 = 0.97 DB4/(DB1 + DB2 + DB3) = 0.96/1.97 = 0.49 | Oxidized Oligomers and/or higher level oligomers | |

TABLE 8b

Types of double bonds (DB1, DB2, DB3 and DB4) detected by $^1$H-NMR in CMTAG fractions

| Fatty Acid | Code | Chemical Structure |
|---|---|---|
| Oleic acid (C18:1) | DB1 | *(structure of oleic acid methyl ester)* |
| Linoleic acid (C18:2) | DB2 | *(structure of linoleic acid methyl ester)* |
| Myristoleic acid (C14:1) | DB3 | *(structure of myristoleic acid methyl ester)* |
| Decenoic acid | DB4 | *(structure of decenoic acid methyl ester)* |

HPLC of CMTAG Fractions

Figure 20:
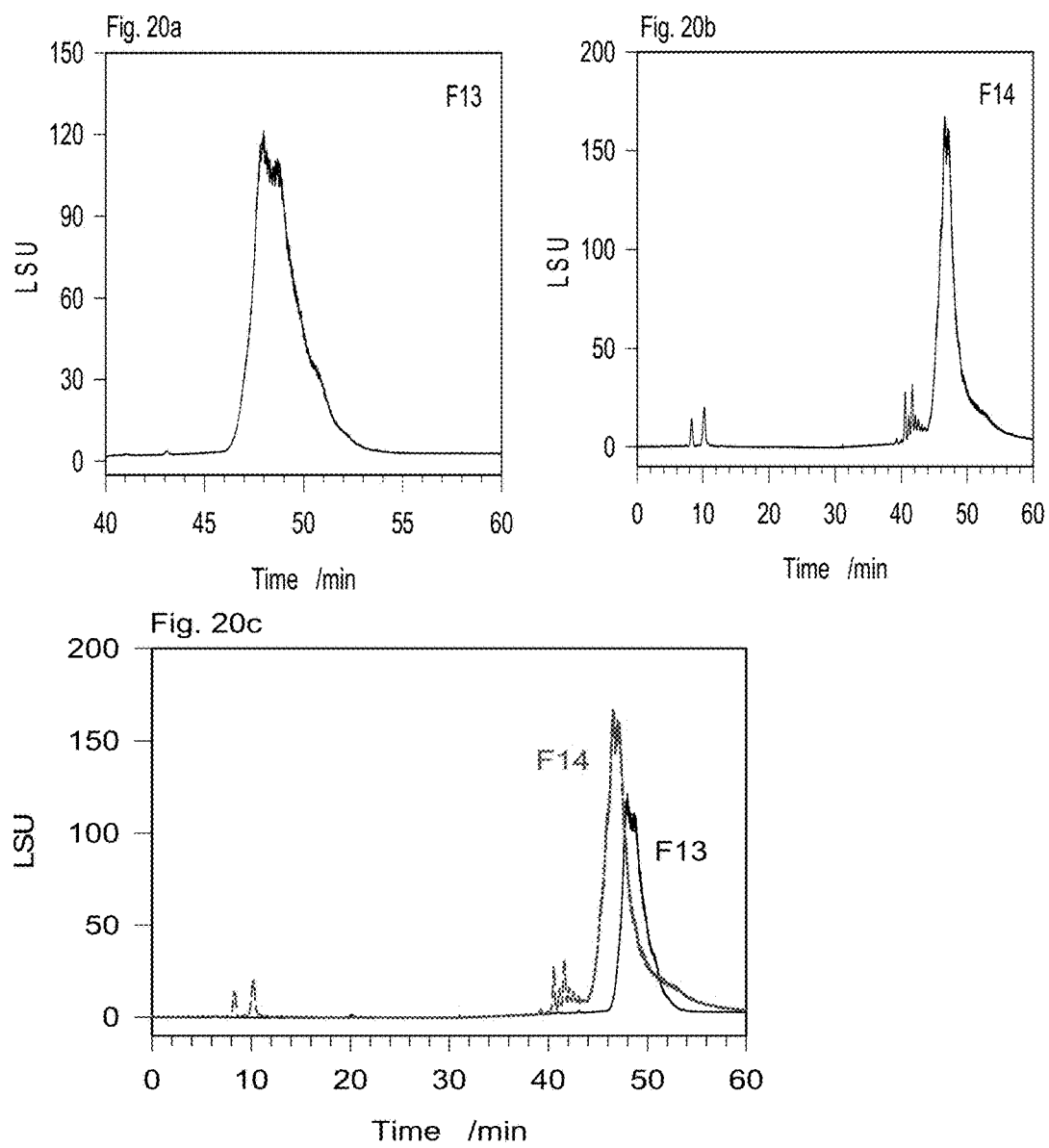
FIG. 20a depicts a HPLC of Fraction 13 (TAG trimers) of Canola oil MTAG.
FIG. 20b depicts a HPLC of Fraction 14 (TAG trimers) of Canola oil MTAG.
FIG. 20c depicts a HPLC of Fractions 13 and Fractions 14 (TAG trimers) of Canola oil MTAG overlaid.

The HPLC curves of the fractions of CMTAG composed of monomers (F2 to F6) are shown in FIGS. 18*a* to 18*e*, those of dimers (F8 to F11) in FIGS. 19*a* to 19*d* and those of trimers (F13 and F14), in FIGS. 20*a* and 20*b*, respectively. The HPLC curves of each group are overlaid for comparison purposes, and are shown in separated panels in the corresponding figures. The retention times of the different peaks for each fraction are listed in Table 9.

Figure 18:
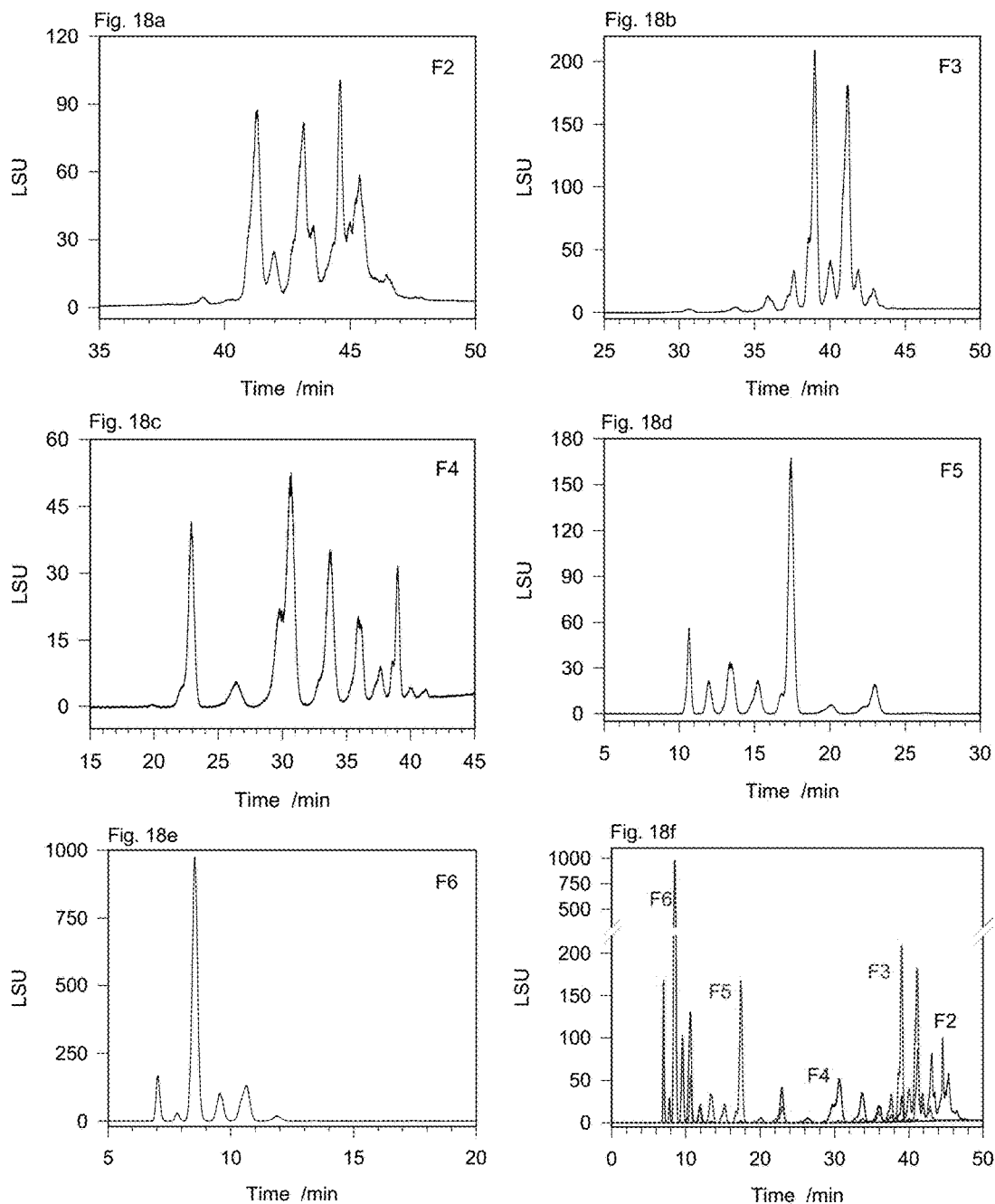
FIG. 18a depicts a HPLC of Fraction 2 (TAG monomers) of Canola oil MTAG.
FIG. 18b depicts a HPLC of Fraction 3 (TAG monomers) of Canola oil MTAG.
FIG. 18c depicts a HPLC of Fraction 4 (TAG monomers) of Canola oil MTAG.
FIG. 18d depicts a HPLC of Fraction 5 (TAG monomers) of Canola oil MTAG.
FIG. 18e depicts a HPLC of Fraction 6 (TAG monomers) of Canola oil MTAG.
FIG. 18f depicts a HPLC of Fractions 2 through Fraction 6 (TAG monomers) of Canola oil MTAG overlaid.
Figure 19:
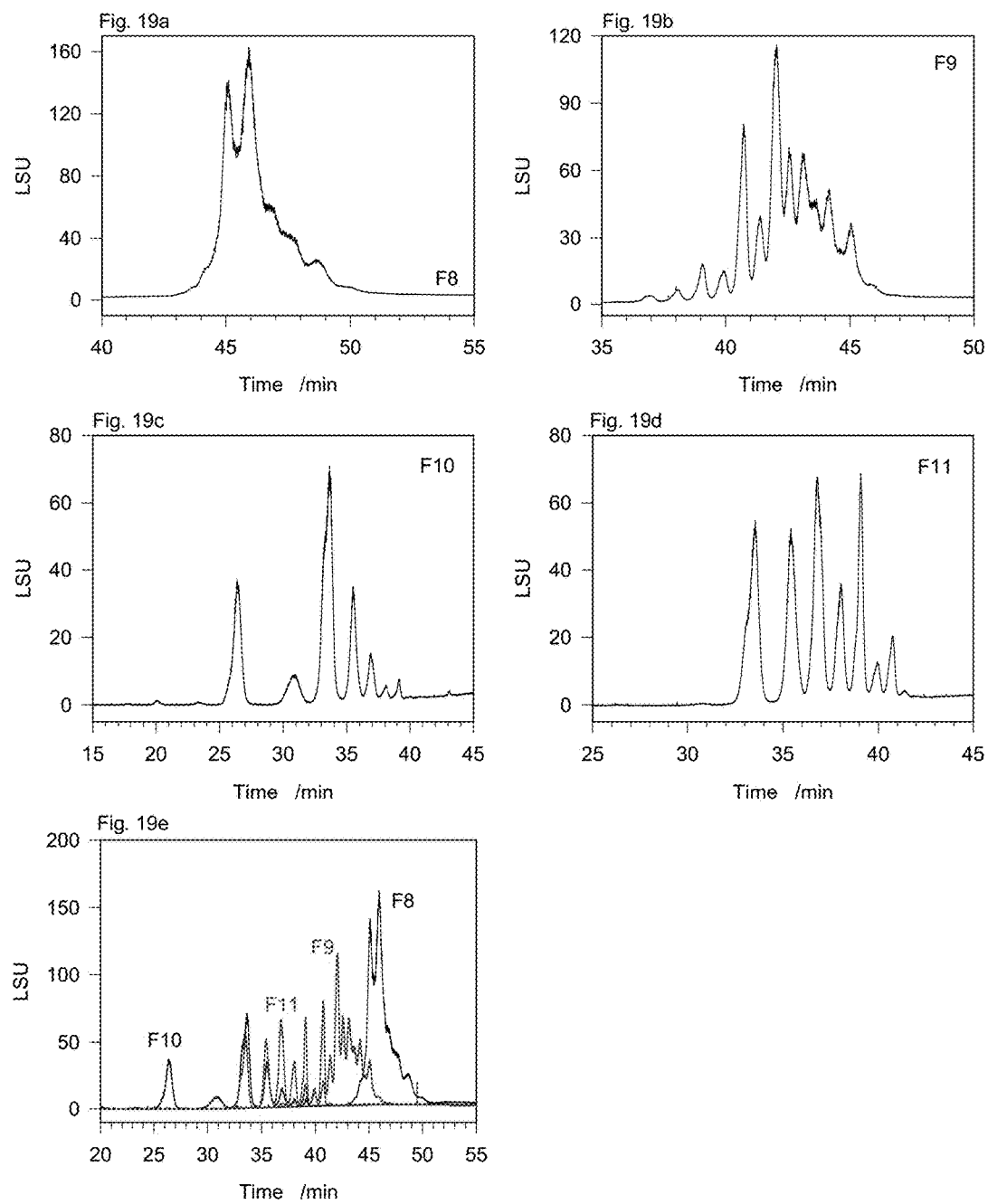
FIG. 19a depicts a HPLC of Fraction 8 (TAG dimers) of Canola oil MTAG.
FIG. 19b depicts a HPLC of Fraction 9 (TAG dimers) of Canola oil MTAG.
FIG. 19c depicts a HPLC of Fraction 10 (TAG dimers) of Canola oil MTAG.
FIG. 19d depicts a HPLC of Fraction 11 (TAG dimers) of Canola oil MTAG.
FIG. 19e depicts a HPLC of Fractions 8 through Fraction 11 (TAG dimers) of Canola oil MTAG overlaid.

As can be seen in FIG. 18*f*, the elution times of the monomers in F6, F5, F4, F3 and F2, followed the reverse sequence of collection, indicating a steady decrease in polarity. Note that some peaks of the fractions overlap (peak at 10.6 and 11.9 min between F6 and F5, 23 min between F5 and F4, 39.2 min between F4 and F3, and 41.1 min between F3 and F2)

Except F10 which eluted before F11, the dimers also eluted in the reverse sequence of collection (F10, F11, F9 then F8). This indicates that molar mass of the dimers in F10 is smaller than in F11, and that molar mass played a larger role than the polarity during elution.

TABLE 9

HPLC retention times of CMTAG fractions

| Fraction | Structure Type | HPLC Retention time |
|---|---|---|
| F1 | Olefins | 34, 36.5, 37.9, 39.8, 40.7, 41.7, 42.8, 43.5, 44.2, 45.1, 45.6 |
| F2 | Monomers: >40% | 39.1, 41.1, 41.9, 42.9, 43.4, 44.5, 45.4, 46.5 |

TABLE 9-continued

HPLC retention times of CMTAG fractions

| Fraction | Structure Type | HPLC Retention time |
|---|---|---|
| F3 | | 30.6, 33.6, 35.9, 37.6, 38.9, 40.1, 41.1, 41.9, 42.9 |
| F4 | | 19.8, 22.8, 26.3, 29.8, 30.6, 33.6, 35.9, 37.5, 38.9, 40.1, 41.1 |
| F5 | | 10.6, 11.9, 13.4, 15.2, 16.8, 17.4, 20.1, 22.2, 22.9 |
| F6 | | 7.1, 7.8, 8.5, 9.6, 10.6, 11.9 |
| F7 | | 7.2, 8.1, 8.8, 9.9, 43.1 |
| F8 | Di- | 45.1, 45.9, 48.6 |
| F9 | mers: ~30-40% | 36.8, 38.1, 39.1, 39.9, 40.7, 41.4, 42.1, 42.5, 43.2, 43.5, 44.2, 45.1 |
| F10 | | 19.9, 23.3, 26.4, 30.8, 33.6, 35.6, 36.8, 38.1, 39.2 |
| F11 | | 33.6, 35.4, 36.8, 38.1, 39.2, 39.9, 40.7, 41.4 |
| F12 | | 4.4, 4.9, 5.3, 5.7, 6.3, 7.9, 11.9, 19.5, 22.5, 25.4, 29.7, 32.8, 33.2, 35.2, 40.9, 50.5 |
| F13 | Tri- | 19.9, 47.7, 48.7 |
| F14 | mers: <10% | 8.3, 10.3, 39.2, 39.9, 40.6, 41.1, 41.7, 42.1, 42.6, 46.6, 47.1 |
| F15 | | 3.9, 4.9, 5.5, 6.6, 7.5, 8.5, 9.9, 11.8, 16.3, 17.8, 21.3, 34.8, 36.5, 37.5, 38.4, 39.2, 39.9, 40.5, 41.3, 41.7, 42.3, 42.8, 43.4, 44.2, 44.9 |

The Possible Structures of CMTAG

The possible structures of CMTAG compatible with the fatty acids detected by $^1$H-NMR (Table 5) are presented in Scheme 4. These contain fatty acids with terminal double bonds with n=0, and internal double bonds with n=2 or 8, as well as saturated fatty acids with m=15 or 17 and a=1.

Scheme 4. Possible structures composing canola oil MTAG.

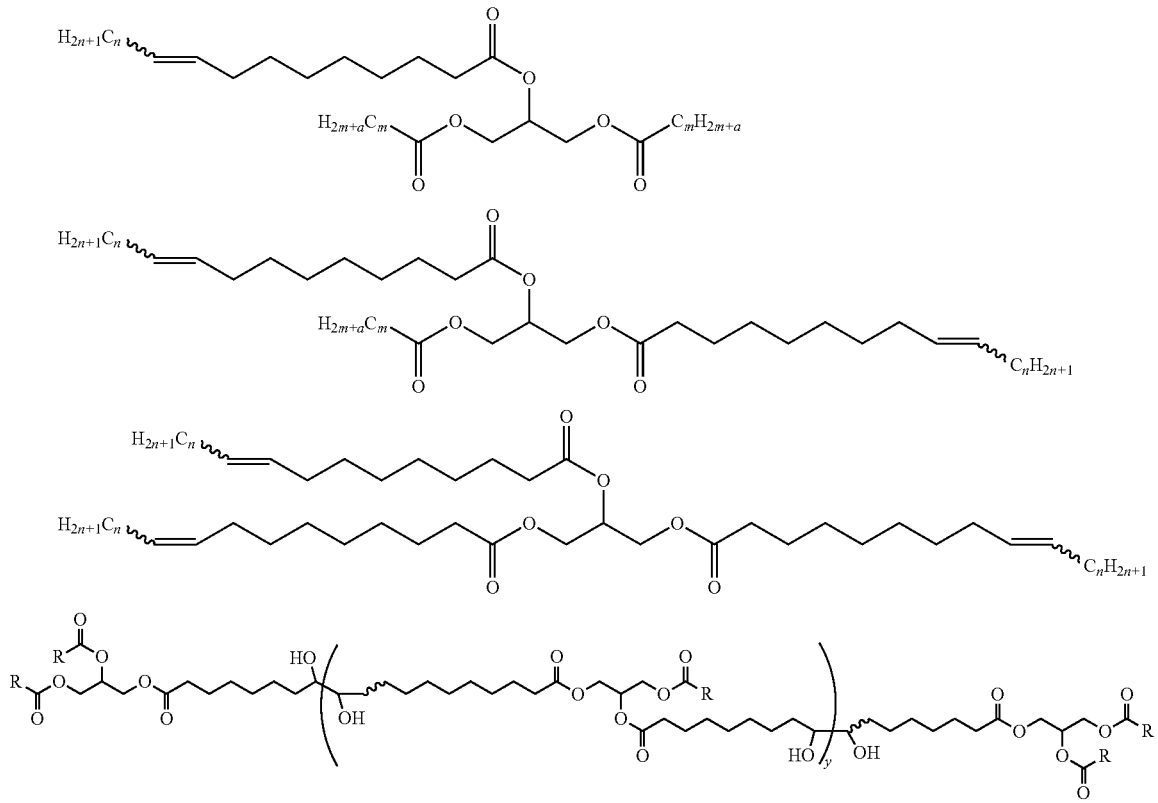

$n = 0, 2, 8; m = 16$ or $18; y = 0\text{-}8, a = \text{-}5, \text{-}3, \text{-}1$ or $1$.

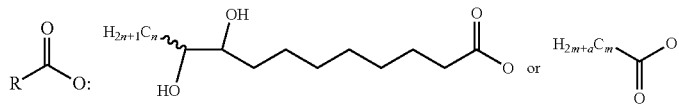

-continued

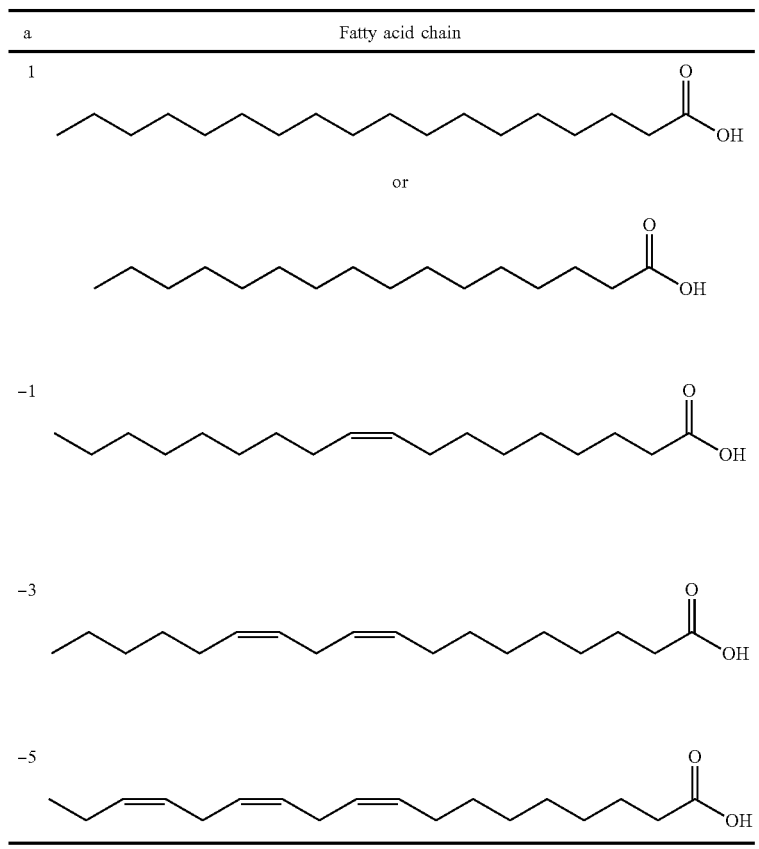

Physical Properties of CMTAG
Thermal degradation of CMTAG

Figure 21:
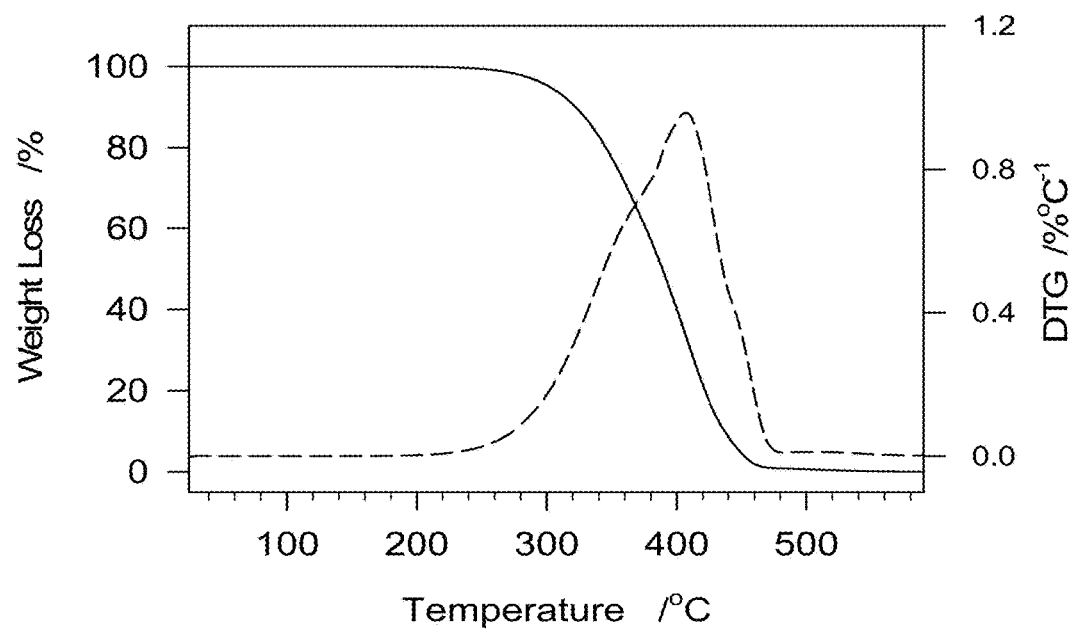
FIG. 21 depicts a TGA (10° C./min) and DTG of MTAG of canola oil.

The TGA and DTG profiles of the MTAG are shown in FIG. 21. TGA and DTG reveal one main decomposition mechanism for the MTAG, associated with the breakage of the ester bonds. The onset of degradation of CMTAG as measured by the temperature at 1, 5 and 10% decomposition was 262, 302 and 322° C., respectively. The extrapolated onset temperature is 333° C. As can be seen from the TGA and DTG curves, the decomposition ends at 470° C. The DTG peak occurs at 408° C. Nearly 60 wt % of the CMTAG decomposed at this temperature. The data indicates a thermal stability relatively higher than common commercial vegetable oils, such as olive, canola, sunflower and soybean oils, for which first DTG peaks as low as 325° C. have been detected.

Crystallization and Melting Behavior of CMTAG

Figure 22A:
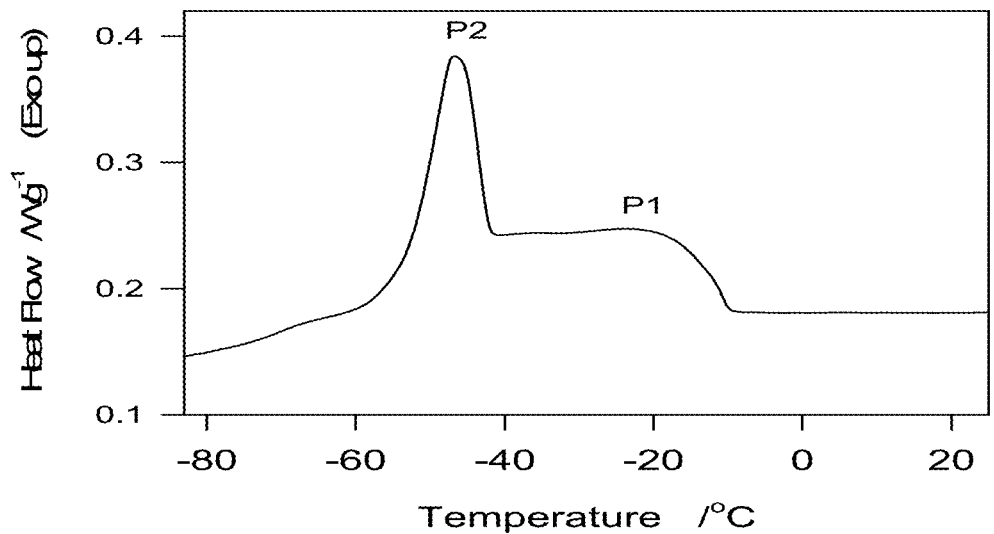
FIG. 22a depicts DSC thermograms of CMTAG obtained during cooling at 5.0° C./min.
Figure 22B:
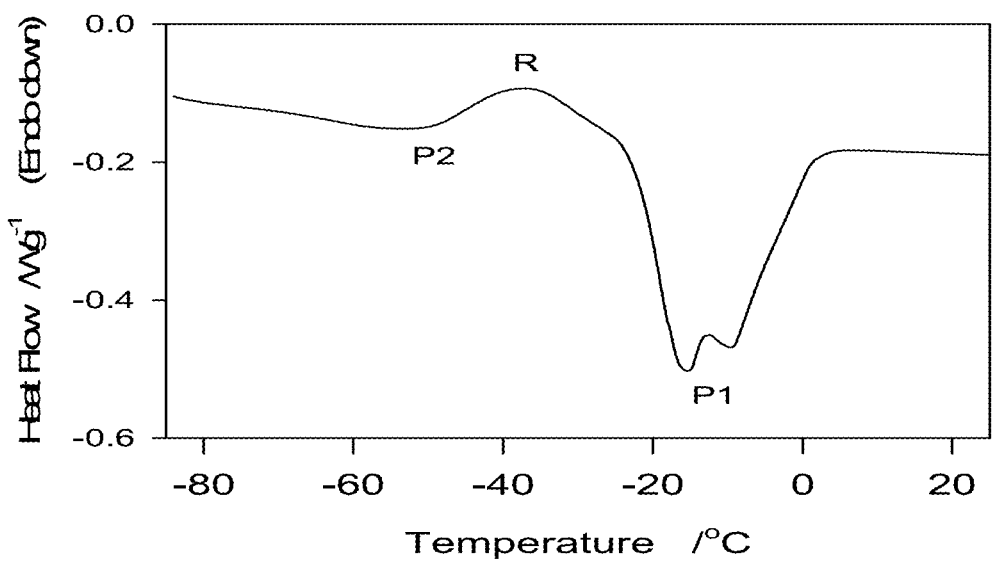
FIG. 22b depicts DSC thermograms of CMTAG obtained during subsequent heating at 5.0° C./min.

The DSC thermograms obtained on cooling CMTAG at 5.0° C./min and subsequent heating at 5° C./min are presented in FIGS. 22a and 22b, respectively. The corresponding thermal data is listed in Table 10. The onset temperature of crystallization (−10° C.) and offset temperature of melting (2° C.) indicate that the material remains liquid at low temperature. Two exothermic peaks were observed in the cooling thermogram at sub-zero temperatures (P1 and P2 at ∼−18° C.∼−46° C. in FIG. 22a). The crystallization peak showing at ∼−18° C. is associated with the crystallization of an oleic acid-rich (olein) fraction of CMTAG, and peak showing at ∼−46° C. is associated with the crystallization of a linolenic-rich (linoleic) fraction of CMTAG.

Two endothermic events separated by a resolved exotherm were observed in the heating trace of CMTAG (P1, P2 and R in FIG. 22b). R is an indication that the material is polymorphic. The recorded enthalpy of heating, calculated from the area of the endotherms was higher than the total enthalpy of crystallization by ∼18 J/g (Table 10) indicating a competition of exothermic and endothermic events during heating which is the result of recrystallization mediated by melt.

The relative contents of the linolein and olein fractions as estimated with the enthalpies of crystallization of P1 and P2 are 33 and 67%, respectively. This is in good agreement with the composition of the starting canola oil material which contains ∼60% of oleic acid and 30% of linoleic and linolenic acids.

TABLE 10

Thermal data of CMTAG obtained on cooling and heating. $T_{on}$, $T_{off}$, $T_{1-3}$: onset, offset and peak temperatures (° C.), ΔH (J/g): Enthalpy

| | Temperatures (° C.) | | | | | Enthalpy (J/g) | | |
|---|---|---|---|---|---|---|---|---|
| | $T_{on}$ | $T_{off}$ | $T_1$ | $T_2$ | $T_3$ | $\Delta H_1$ | $\Delta H_2$ | $\Delta H$ |
| Crystallization | −9.77 | −56.32 | −18.91 | −46.75 | | 17.41 | 35.98 | 36.0 |
| Melting | −66.44 | 1.81 | −49.42 | −15.19 | −9.13 | | | 53.5 |

Solid Fat Content of CMTAG

Solid Fat Content (SFC) versus temperature profiles of CMTAG during cooling (5° C./min) and heating (5° C./min) are shown in FIGS. 23a and 23b, respectively. Both traces indicate that CMTAG remains liquid at temperatures close to freezing conditions. As can be seen in FIG. 23a, the SFC cooling curve presented two segments indicative of a two-step solidification process. The two SFC segments can be associated with the solidification of two fractions of the CMTAG, similar to the two exothermic events observed in DSC.

Microstructure Development of CMTAG

The microstructural analysis was performed in order to determine the microstructure size, shape, development kinetics and final network formation. The development of the microstructure was followed while the sample was cooling at 5° C./min. FIGS. 24a-24b highlight the development of the microstructure of the CMTAG during cooling at 5° C./min. Crystallization initiated at ∼−9.1±0.5° C. with very small crystals of average size 3±1 μm. At this stage, the nucleation as indicated by the continuous appearance of the crystals was relatively slow. The same type of crystals developed until −46° C. at which new crystals appeared following a secondary nucleation. Crystal development at this stage was relatively fast and completed at −56° C. The crystals remained small and homogeneously distributed. As shown in the PLM taken at −48° C. (FIG. 24b), the brightness of the crystals increased dramatically during this crystallization stage, indicating a significant increase in crystal perfection and order. Although no further development in the number and size of the crystal was observed below −56° C., the brightness of the fat network improved steadily, indicating an increase of the crystal perfection and order. Note that the different modes of crystallization indicated by both DSC and SFC are reflected in the microstructure development. The onset temperatures of the DSC exotherms P1 and P2 match the temperatures at which the first white spots and the second nucleation observed in the PLM. Note that apart from nucleating at two distinct temperatures with very different nucleation rates, the crystals of the two microstructures cannot be distinguished even at 500× magnification.

Flow Behavior and Viscosity of CMTAG

Shear rate—shear stress curves of CMTAG obtained at different temperatures are displayed in FIGS. 25a and 25b. FIG. 26 shows the viscosity versus temperature curves obtained during cooling of CMTAG at 3° C./min and 1° C./min. The application of the Herschel-Bulkley equation (Eq. 1) to share rate—shear stress data obtained for the MTAG at temperatures of 0° C. to 100° C. ($R^2$>0.9999) generated power index values (n) all approximately equal to unity, indicating Newtonian behavior. Fits to the Herschel-Bulkley (eq. 1) model are included in FIGS. 25a and 25b. The flow behavior observed for CMTAG is very similar to that of vegetable oils. The viscosity versus temperature of CMTAG obtained using the ramp procedure presented exponential behavior of liquid hydrocarbons.

B. Polyols from MTAG of Canola Oil

Synthesis of Polyols from CMTAG

The synthesis of the CMTAG polyol involves epoxidation and subsequent hydroxylation of a MTAG of a natural oil, e.g., canola oil. Any peroxyacid may be used in the epoxidation reaction, and this reaction will convert a portion of or all of the double bonds present in the CMTAG to epoxide groups. Peroxyacids (peracids) are acyl hydroperoxides and are most commonly produced by the acid-catalyzed esterification of hydrogen peroxide. Any suitable peroxyacid may be used in the epoxidation reaction. Examples of hydroperoxides that may be used include, but are not limited to, hydrogen peroxide, tert-butylhydroperoxide, triphenylsilylhydroperoxide, cumylhydroperoxide, trifluoroperoxyacetic acid, benzyloxyperoxyformic acid, 3,5-dinitroperoxybenzoic acid, m-chloroperoxybenzoic acid, and hydrogen peroxide. The peroxyacids may be formed in-situ by reacting a hydroperoxide with the corresponding acid, such as formic or acetic acid. Other organic peracids may also be used, such as benzoyl peroxide, and potassium persulfate. The epoxidation reaction can be carried out with or without solvent. Commonly used solvents in the epoxidation may be chosen from the group including but not limited to aliphatic hydrocarbons (e.g., hexane and cyclohexane), organic esters (e.g., ethyl acetate), aromatic hydrocarbons (e.g., benzene and toluene), ethers (e.g., dioxane, tetrahydrofuran, ethyl ether, tert-butyl methyl ether) and halogenated hydrocarbons (e.g., dicholoromethane and chloroform).

Subsequent to the epoxidation reaction, the reaction product may be neutralized. A neutralizing agent may be added to neutralize any remaining acidic components in the reaction product. Suitable neutralizing agents include weak bases, metal bicarbonates, or ion-exchange resins. Non-limiting examples of neutralizing agents that may be used include ammonia, calcium carbonate, sodium bicarbonate, magnesium carbonate, amines, and resin, as well as aqueous solutions of neutralizing agents. Subsequent to the neutralization, commonly used drying agents may be utilized. Such drying agents include inorganic salts (e.g. calcium chloride, calcium sulfate, magnesium sulfate, sodium sulfate, and potassium carbonate).

After the preparation of the epoxidized CMTAG, the next step is to ring-open at least a portion of the epoxide groups via a hydroxylation step or a hydrogenation reaction with Raney-Ni. In the present work, all the epoxide groups were opened. The hydroxylation step includes reacting the oxirane ring of the epoxide in an aqueous or organic solvent in the presence of an acid catalyst in order to hydrolyze the oxirane ring to a dihydroxy intermediate. In some aspects, the solvent may be water, aliphatic hydrocarbons (e.g., hexane and cyclohexane), organic esters (e.g., ethyl acetate), aromatic hydrocarbons (e.g., benzene and toluene), ethers (e.g., dioxane, tetrahydrofuran, ethyl ether, tert-butyl methyl ether) and halogenated hydrocarbons (e.g., dicholoromethane and chloroform), e.g., water and/or tetrahydrofuran. The acid catalyst may be an acid such as sulfuric, pyrosulfuric, perchloric, nitric, halosulfonic acids such as fluorosulfonic, chlorosulfonic or trifluoromethane sulfonic, methane sulfonic acid, ethane sulfonic acid, ethane disulfonic acid, benzene sulfonic acid, or the benzene disulfonic, toluene sulfonic, naphthalene sulfonic or naphthalene disulfonic acids, and perchloric acid. As needed, subsequent washing steps may be utilized, and suitable drying agents (e.g., inorganic salts) may be used.

Materials for CMTAG Polyol Synthesis

Formic acid (88 wt %) and hydrogen peroxide solution (30 wt %) were purchased from Sigma-Aldrich and perchloride acid (70%) from Fisher Scientific. Raney Nickel, hexanes, dichloromethane, ethyl acetate and terahydrofuran (THF) were purchased from ACP chemical Int. (Montreal, Quebec, Canada) and were used without further treatment.

Synthesis of CMTAG Polyol

Polyol was prepared from MTAG of canola oil, which may be referred to herein as CMTAG Polyol. The CMTAG Polyol was prepared using two routes, each involving a two-step reaction: (1) CMTAG Polyol was prepared by epoxidation by formic acid and $H_2O_2$ followed by a hydrogenation (100-150° C. and 1000 psi) with Raney Nickel as a catalyst, as described in Scheme 5; (2) CMTAG Polyol was also prepared by epoxidation followed by hydroxylation, as described in Scheme 6. The hydroxylation reaction was performed at room temperature with $HClO_4$ (5%) as a catalyst and in $THF:H_2O$ (3:2). Reaction procedures followed in this study are described in the following sections.

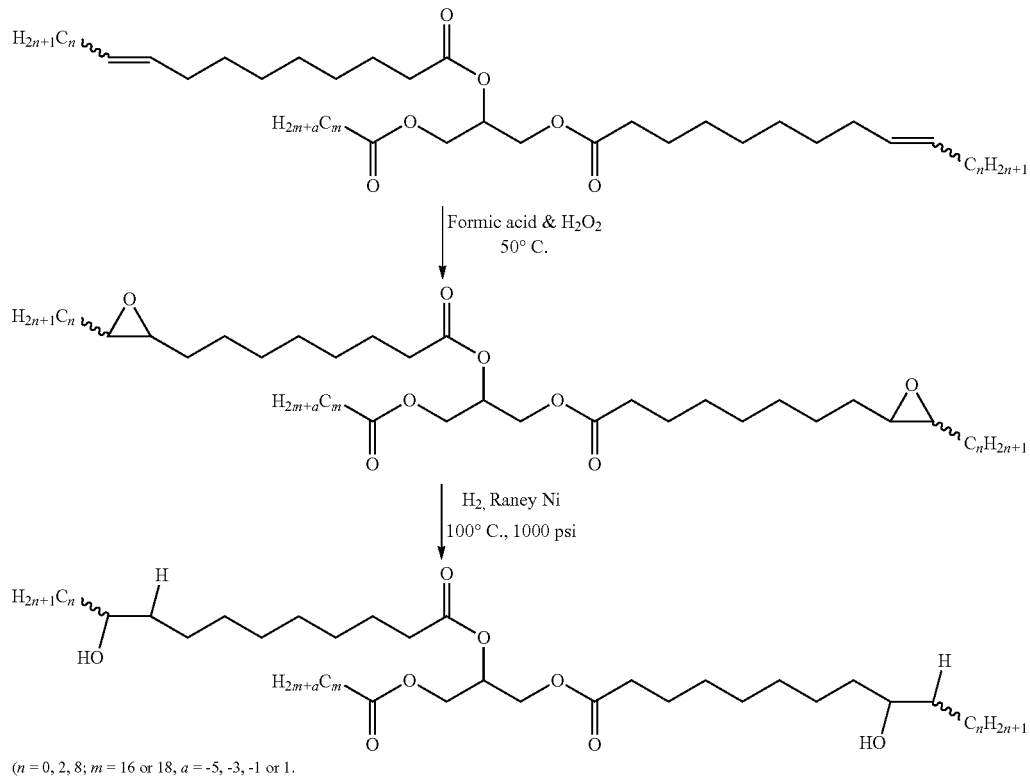

Scheme 5. Epoxidation and hydrogenation synthesis route of CMTAG Polyol.

($n = 0, 2, 8$; $m = 16$ or $18$, $a = -5, -3, -1$ or $1$.

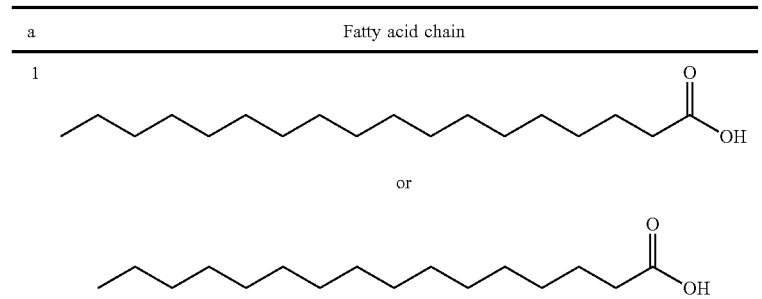

| a | Fatty acid chain |
|---|---|
| 1 | |

| a | Fatty acid chain |
|---|---|
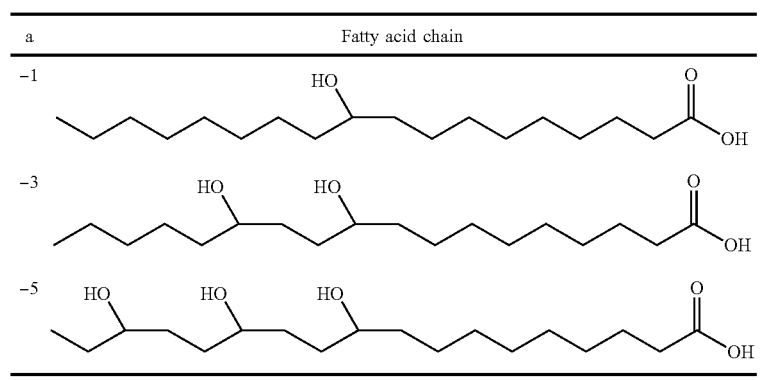
Scheme 6. Epoxidation and hydroxylation synthesis route of CMTAG Polyol.
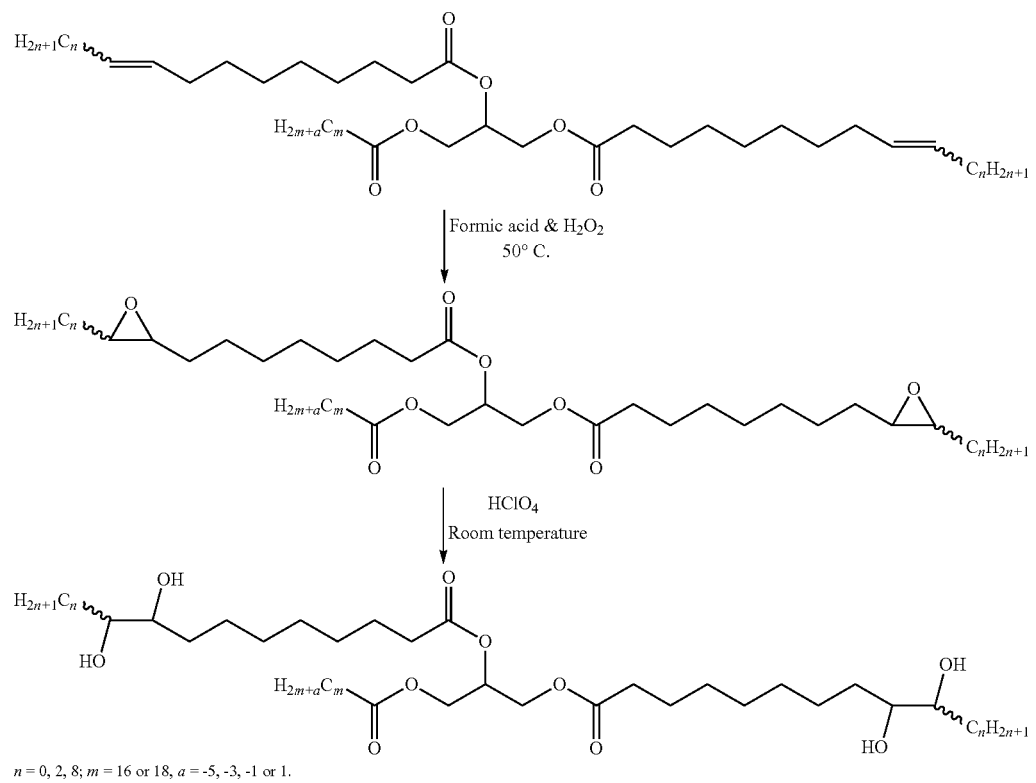
$n = 0, 2, 8; m = 16$ or $18, a = -5, -3, -1$ or $1$.
| a | Fatty acid chain |
|---|---|
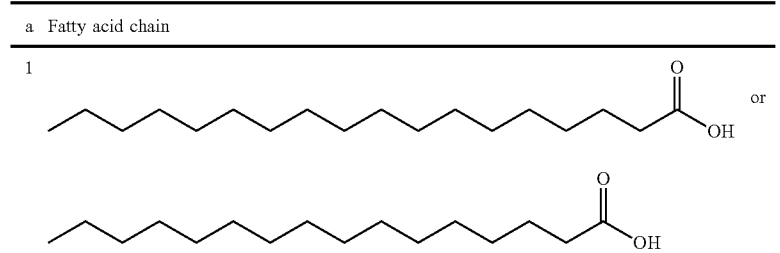

a Fatty acid chain

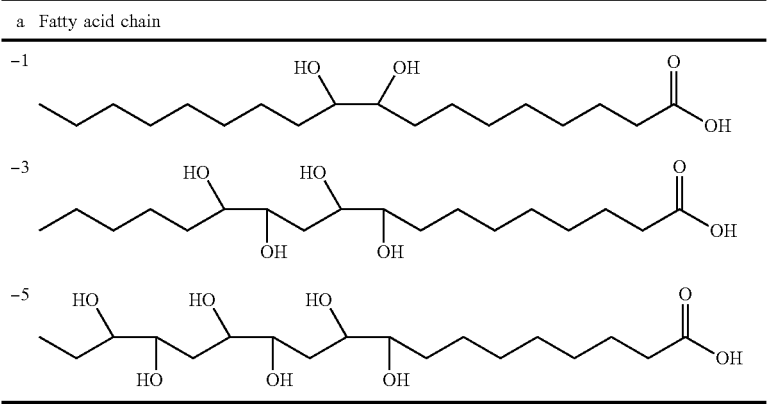

Epoxidation Procedure

Formic acid (88%; 200 g) was added to a solution of CMTAG (200 g) in dichloromethane (240 mL). This mixture was cooled to 0° C. Hydrogen peroxide (30%, 280 g) was added dropwise. The resulting mixture was stirred at 50° C., and the progress of the reaction was monitored by a combination of TLC and $^1$H-NMR. The reaction was completed after 48 to 50 hours.

Upon completion, the reaction mixture was diluted with 250 mL dichloromethane, washed with water (200 mL×2), and then with saturated sodium hydrogen carbonate (200 mL×2), and water again (200 mL×2), then dried over anhydrous sodium sulfate. After removing the drying agent by filtration, solvent was removed by roto-evaporation.

$^1$H-NMR Results of Epoxidized CMTAG

Figure 27:
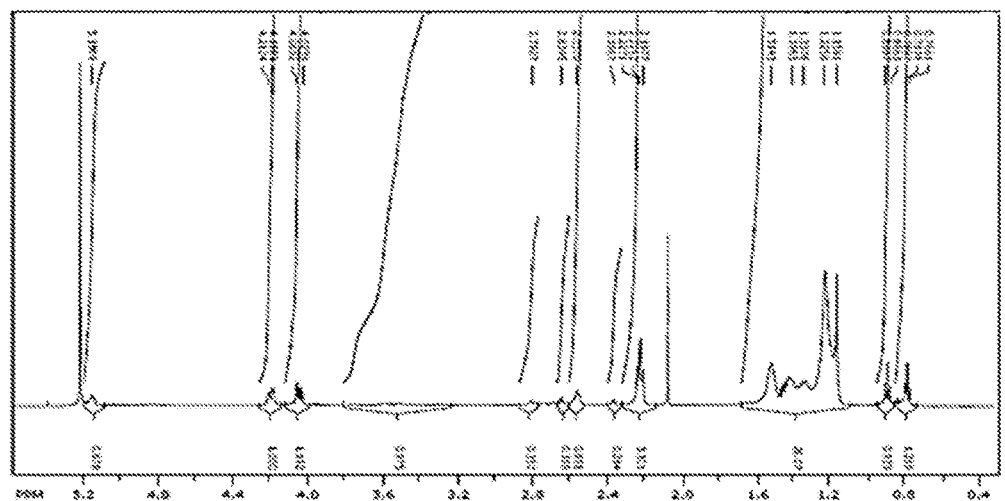
FIG. 27 depicts $^1$H-NMR spectrum of epoxy CMTAG.

The $^1$H-NMR of epoxy CMTAG is shown in FIG. 27. The protons of the glycerol skeleton, —CH$_2$CH(O)CH$_2$— and —OCH$_2$CHCH$_2$O— are present at δ 5.3-5.2 ppm and 4.4-4.1 ppm, respectively; —C(=O)CH$_2$— at δ 2.33-2.28 ppm; α-H to —CH=CH— at δ 2.03-1.98 ppm; and —C(=O)CH$_2$CH$_2$— at δ 1.60 ppm. There are two types of —CH$_3$, one with n=3 (myristoleic) and another with n=9 (linoleic and linolenic). The first presented protons at δ=1.0-0.9 ppm and the second a proton at 0.9-0.8 ppm, respectively. The chemical shift at 5.8, 5.4 and 5.0 ppm, characteristic of double bonds, disappeared, whereas, the chemical shift at 2.85 ppm, related to non-terminal epoxy ring, and the chemical shift at 2.7 to 2.4 ppm, related to terminal epoxy ring, appeared, indicating that the epoxidation reaction was successful and complete.

Hydrogenation of the CMTAG Epoxide

CMTAG epoxide (50 g) in 200 mL ethyl acetate with 10 g of Raney Nickel was hydrogenated at 1000 psi in a high pressure reactor (Model 4848, Parr, Moline, Ill.). The reaction was run at 100-150° C. for 5 hours, after which the reaction was cooled down to room temperature and the hydrogen released. The reaction mixture was purged with N$_2$ and then filtrated through celite. The polyol was collected after ethyl acetate was removed by roto-evaporation.

Hydroxylation Procedure

Approximately 200 g crude epoxy CMTAG was dissolved into a 500 mL solvent mixture of THF/H$_2$O (3:2) containing 14.5 g perchloric acid. The reaction mixture was stirred at room temperature and the progress of the reaction was monitored by a combination of TLC and $^1$H-NMR. The reaction was completed after 36 hours. The reaction mixture was poured into 240 mL water and extracted with CH$_2$Cl$_2$ (2×240 mL). The organic phase was washed by water (2×240 mL), followed by 5% aqueous NaHCO$_3$ (2×200 mL) and then water (2×240 mL) again. The organic phase was then dried over Na$_2$SO$_4$. After removing the drying agent by filtration, the solvent was removed with a rotary evaporator and further dried by vacuum overnight, giving a light yellow grease-like solid.

Analytical Methods for CMTAG Polyol

The CMTAG Polyol was analyzed using different techniques. These techniques can be broken down into: (i) chemistry characterization techniques, including OH value, acid value, nuclear magnetic resonance (NMR), and high pressure liquid chromatography (HPLC); and (ii) physical characterization methods, including thermogravimetric analysis (TGA), differential scanning calorimetry (DSC), and rheology.

Chemistry Characterization Techniques for CMTAG Polyol

OH and acid values of the CMTAG Polyol was determined according to ASTM D1957-86 and ASTM D4662-03, respectively.

$^1$H-NMR spectra were recorded in CDCl$_3$ on a Varian Unity-INOVA at 499.695 MHz. $^1$H chemical shifts are internally referenced to CDCl$_3$ (7.26 ppm). All spectra were obtained using an 8.6 μs pulse with 4 transients collected in 16 202 points. Datasets were zero-filled to 64 000 points, and a line broadening of 0.4 Hz was applied prior to Fourier transforming the sets. The spectra were processed using ACD Labs NMR Processor, version 12.01.

Physical Characterization Techniques for CMTAG Polyol

TGA was carried out on a TGA Q500 (TA Instruments, DE, USA) equipped with a TGA heat exchanger (P/N 953160.901). Approximately 8.0-15.0 mg of sample was loaded in the open TGA platinum pan. The sample was heated from 25 to 600° C. under dry nitrogen at a constant rate of 10° C./min.

DSC measurements of the CMTAG Polyol were run on a Q200 model (TA Instruments, New Castle, Del.) under a nitrogen flow of 50 mL/min. CMTAG Polyol samples of 3.5 to 6.5 (±0.1) mg were run in standard mode in hermetically sealed aluminum DSC pans. The sample was equilibrated at 90° C. for 10 min to erase thermal memory, and then cooled at 5.0° C./min to −90° C. where it was held isothermally for 5 min, and subsequently reheated at a constant rate of 5.0° C./min to 90° C. The "TA Universal Analysis" software was used to analyze the DSC thermograms and extract the peak characteristics. Characteristics of non-resolved peaks were obtained using the first and second derivatives of the differential heat flow.

A temperature-controlled Rheometer (AR2000ex, TA Instruments, DE, USA) was used to measure the viscosity and flow property of the CMTAG Polyol using a 40 mm 2° steel geometry. Temperature control was achieved by a Peltier attachment with an accuracy of 0.1° C. Shear Stress was measured at each temperature by varying the shear rate from 1 to 1200 s$^{-1}$. Measurements were taken at 10° C. intervals from high temperature (100° C.) to 10° C. below the DSC onset of crystallization temperature of each sample. Viscosities of samples were measured from each sample's melting point up to 110° C. at constant temperature rate (1.0 and 3.0° C./min) with constant shear rate (200 s$^{-1}$). Data points were collected at intervals of 1° C. The viscosity obtained in this manner was in very good agreement with the measured viscosity using the shear rate/share stress. The shear rate range was optimized for torque (lowest possible is 10 μNm) and velocity (maximum suggested of 40 rad/s).

Figure 28:
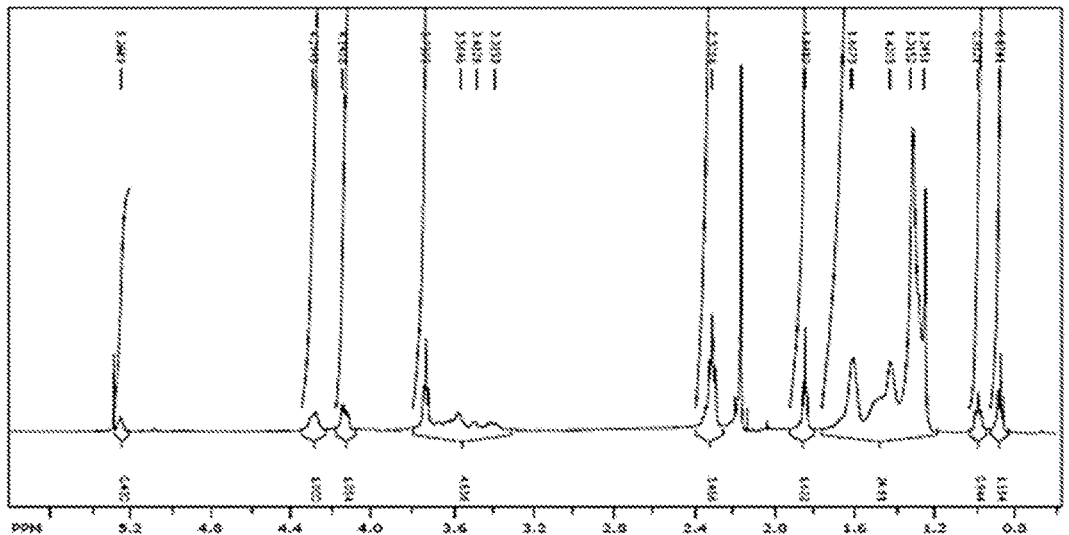
FIG. 28 depicts $^1$H-NMR spectrum of CMTAG Polyol produced with the epoxidation followed by hydroxylation synthesis route.

Compositional Analysis of CMTAG Polyol
$^1$H-NMR Characterization of CMTAG Polyol Obtained with the Epoxidation and Hydroxylation Synthesis Route $^1$H-NMR of CMTAG Polyol produced with the epoxidation followed by hydroxylation synthesis route is shown in FIG. 28. The protons of the glycerol skeleton, —CH$_2$CH(O)CH$_2$— and —OCH$_2$CHCH$_2$O— are present at δ 5.3-5.2 ppm and 4.4-4.1 ppm, respectively; —C(=O)CH$_2$— at δ 2.33-2.28 ppm; —C(=O)CH$_2$CH$_2$— at δ=1.60 ppm; and proton neighbored by —OH appeared at 3.8-3.4 ppm. There are two types of —CH$_3$, one with n=2 present at δ=1.0-0.9 ppm and another with n=8 at 0.9-0.8 ppm. —OH is present at δ=2.2-2.0 ppm.

The chemical shifts at 2.8-2.4 ppm, related to epoxy ring, did not appear, and the chemical shifts at 3.8-3.4 ppm related to protons neighbored by —OH appeared, indicating that the hydroxylation of the epoxy ring was complete.

Possible Structures of CMTAG Polyol from the Epoxidation and Hydroxylation Route The possible structures of CMTAG polyol produced by the hydroxylation procedure, based on the TAG profiles of the MTAG of canola oil, are shown in Scheme 7. These structures are directly related to the structures of CMTAG determined by HPLC and $^1$H-NMR (Scheme 4).

Scheme 7. Possible structures in CMTAG Polyol produced with the epoxidation and hydroxylation synthesis route.

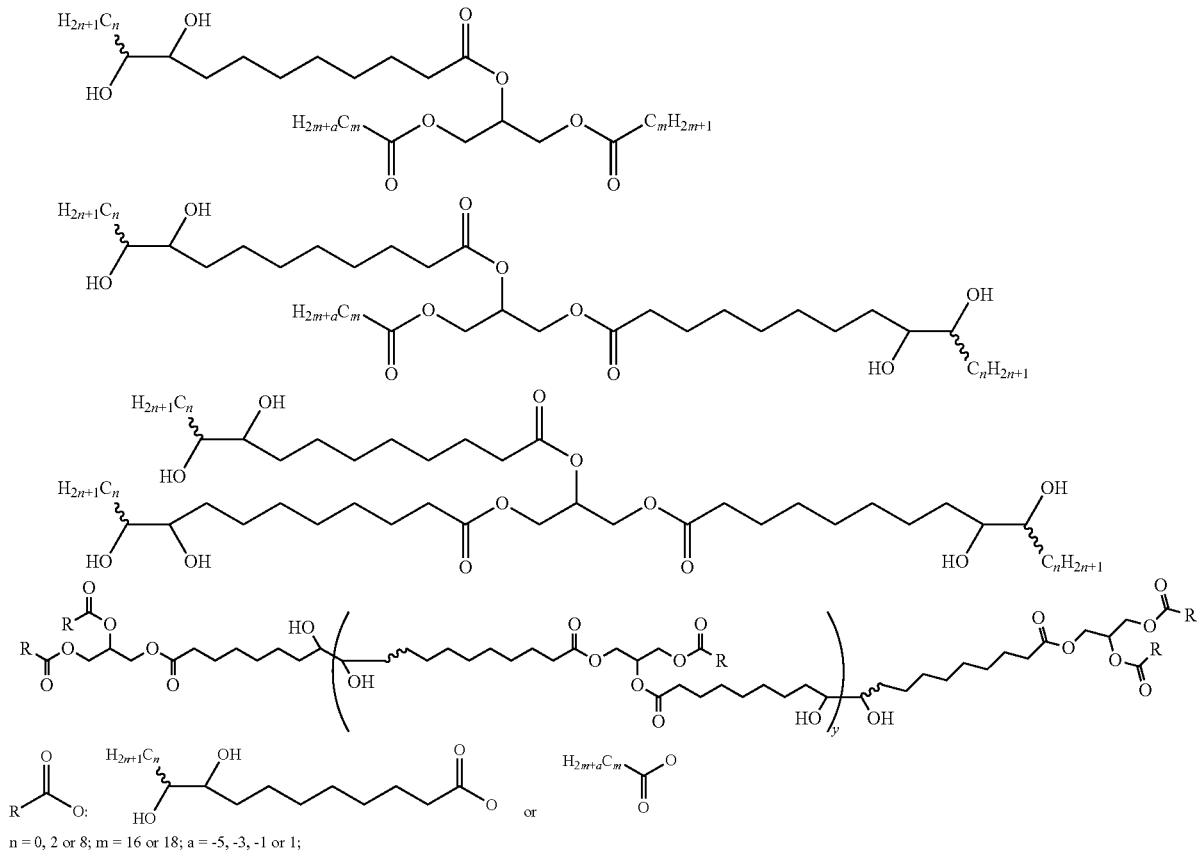

n = 0, 2 or 8; m = 16 or 18; a = -5, -3, -1 or 1;

| a | Fatty acid chain |
|---|---|
| 1 | 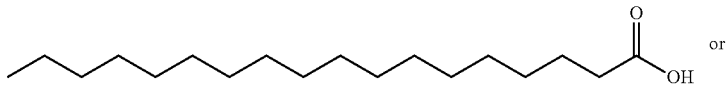 [SMILES: CCCCCCCCCCCCCCCCCC(=O)O] |

| |
|---|
| a Fatty acid chain |

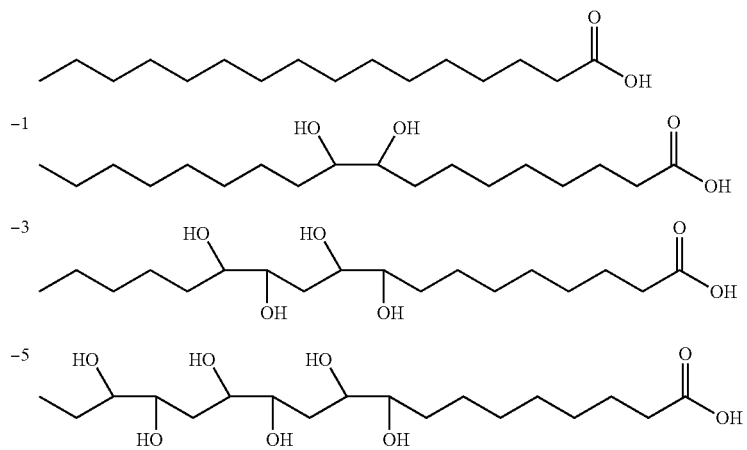

The CMTAG Polyol produced with the epoxidation and hydroxylation route was very viscous and was not used in the preparation of foams. Its suitability for applications such as in polymers, hydrogels etc., will be assessed at a later time.

$^1$H-NMR Characterization of CMTAG Polyol obtained with the Epoxidation and Hydrogenation Synthesis Route $^1$H-NMR of CMTAG Polyol produced by the epoxidation and hydrogenation synthesis route is shown in FIG. 29. The protons of the glycerol skeleton, —CH$_2$CH(O)CH$_2$— and —OCH$_2$CHCH$_2$O— are present at δ 5.3-5.2 ppm and 4.4-4.1 ppm, respectively; —C(=O)CH$_2$— at δ 2.33-2.28 ppm; —C(=O)CH$_2$CH$_2$— at δ 1.60 ppm; and proton neighbored by —OH appeared at 3.8-3.4 ppm. There are two types of —CH$_3$, one with n=2 present at δ=1.0-0.9 ppm and another with n=8 at 0.9-0.8 ppm. —OH is present at δ 1.2 ppm. The chemical shifts at 2.8-2.4 ppm related to epoxy ring disappeared, and the chemical shifts at 3.8-3.4 ppm related to proton neighbored by —OH appeared, indicating that the hydrogenation of epoxy ring was complete.

Possible Structures in CMTAG Polyol

The theoretical structures of CMTAG Polyol produced by the epoxidation and hydrogenation procedure, based on the TAG profile of canola oil are given in Scheme 8. These structures can be directly related to the structures determined by HPLC and $^1$H-NMR of CMTAG and its fractions (Scheme 4). The possible structures of CMTAG Polyol include hydroxyl functionalized monomers, dimers, trimers and higher oligomers.

Scheme 8. Possible structures in CMTAG Polyol produced with the epoxidation and hydrogenation synthesis route.

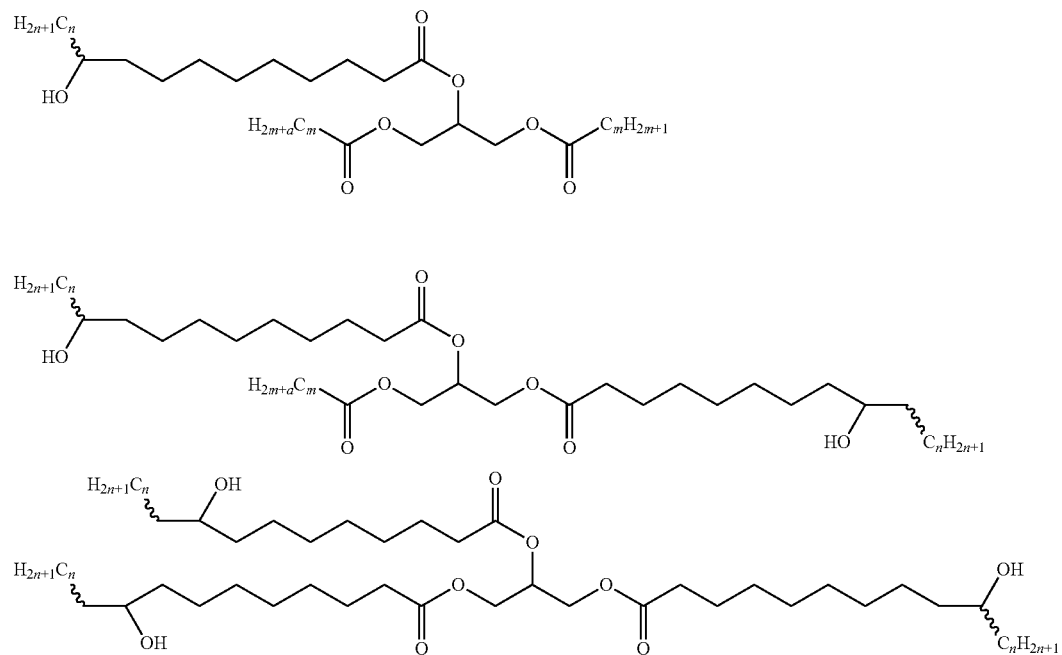

-continued

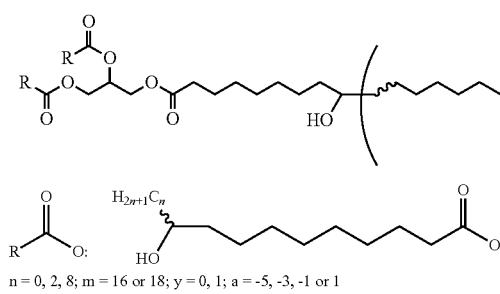
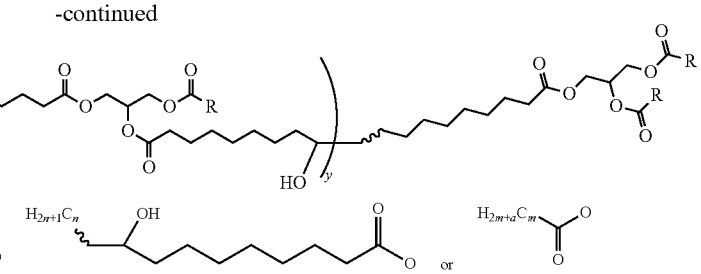

n = 0, 2, 8; m = 16 or 18; y = 0, 1; a = -5, -3, -1 or 1

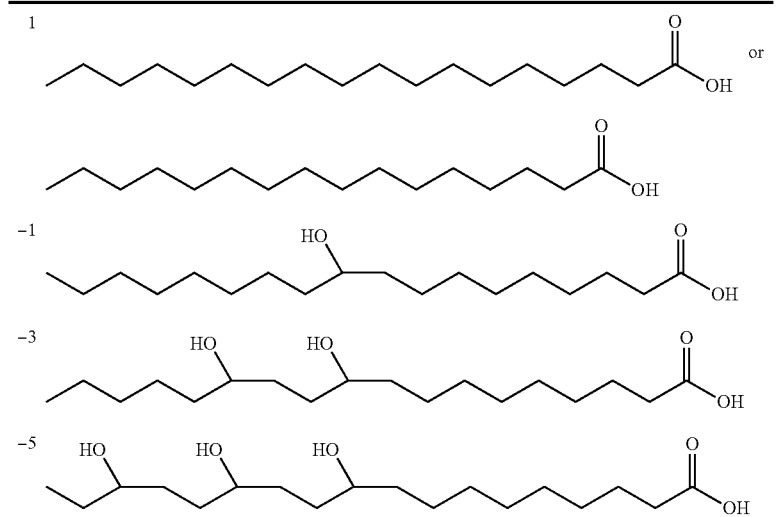

Physical Properties of CMTAG Polyol

The values and uncertainty reported for the physical properties of the CMTAG Polyol are the average and standard deviation, respectively, of duplicates sampled from two batches obtained with reactions performed at the same conditions.

Thermogravimetric Analysis of CMTAG Polyol

The TGA and corresponding DTG profiles of the CMTAG Polyol are shown in the FIGS. 30a and 30b. The onset temperature of degradation of CMTAG Polyol measured at 1, 5 and 10% decomposition and the DTG peak temperatures are provided in Table 11.

TGA revealed a decomposition spanning from ~220° C. to 470° C. The peaks observed in the DTG curve (arrows in FIG. 30) indicate several steps of degradation for the CMTAG Polyol. The first step, recognizable by the prominent DTG peak at 274° C., involved ~15 to 20% weight loss and is associated with the degradation of the hydroxyl groups present in the polyol. The degradation steps represented by the DTG peaks between 330 and 430° C. where ~60% weight loss was recorded, are associated with the breakage of the ester bonds, similar to what was observed in the degradation of the CMTAG. The last step represented by the DTG shoulder at 449° C. is related to the decomposition of higher decomposition temperature fragments.

TABLE 11

Temperature of degradation at 1, 5 and 10% weight loss ($T_{1\%}^d$, $T_{5\%}^d$, $T_{10\%}^d$, respectively) and DTG peak temperatures ($T_{D1-5}$) of CMTAG Polyol

| CMTAG Polyol | Temperature (° C.) | | | | | | | |
|---|---|---|---|---|---|---|---|---|
| | $T_{1\%}^d$ | $T_{5\%}^d$ | $T_{10\%}^d$ | $T_{D1}$ | $T_{D2}$ | $T_{D3}$ | $T_{D4}$ | $T_{D5}$ |
| Sample 1 | 238 | 278 | 297 | 276 | 318 | 351 | 401 | 450 |
| Sample 2 | 222 | 272 | 291 | 272 | 317 | 345 | 402 | 448 |
| Average | 230 ± 11 | 275 ± 4 | 294 ± 4 | 274 ± 3 | 317.5 ± 1 | 348 ± 4 | 401.5 ± 1 | 449 ± 1 |

Crystallization and Melting Behavior of CMTAG Polyol

Figure 31A:
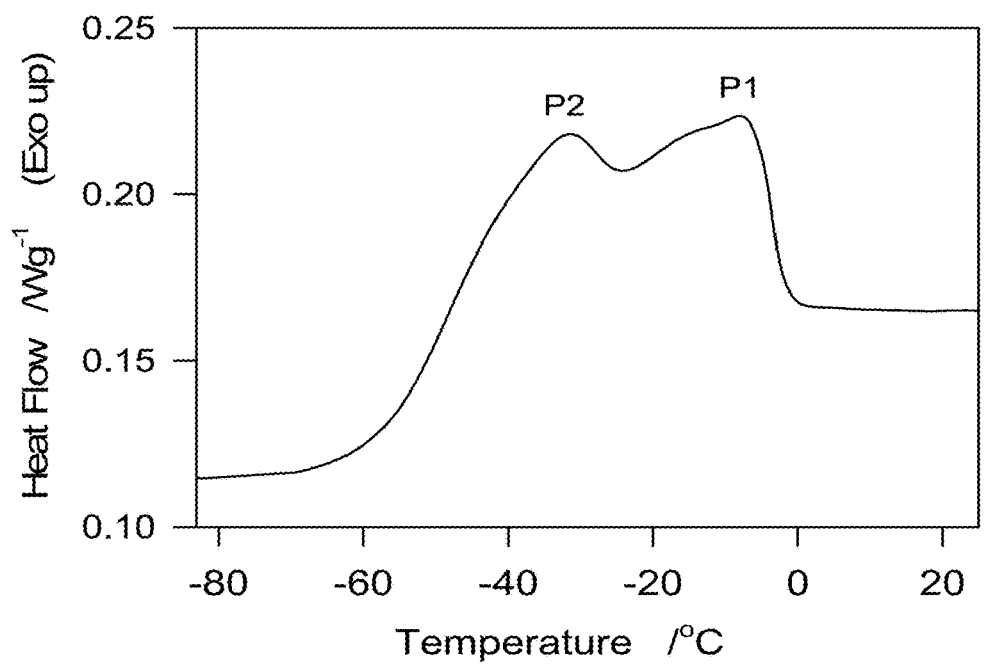
FIG. 31a depicts DSC thermograms of CMTAG Polyol obtained during cooling at 5.0° C./min.
Figure 31B:
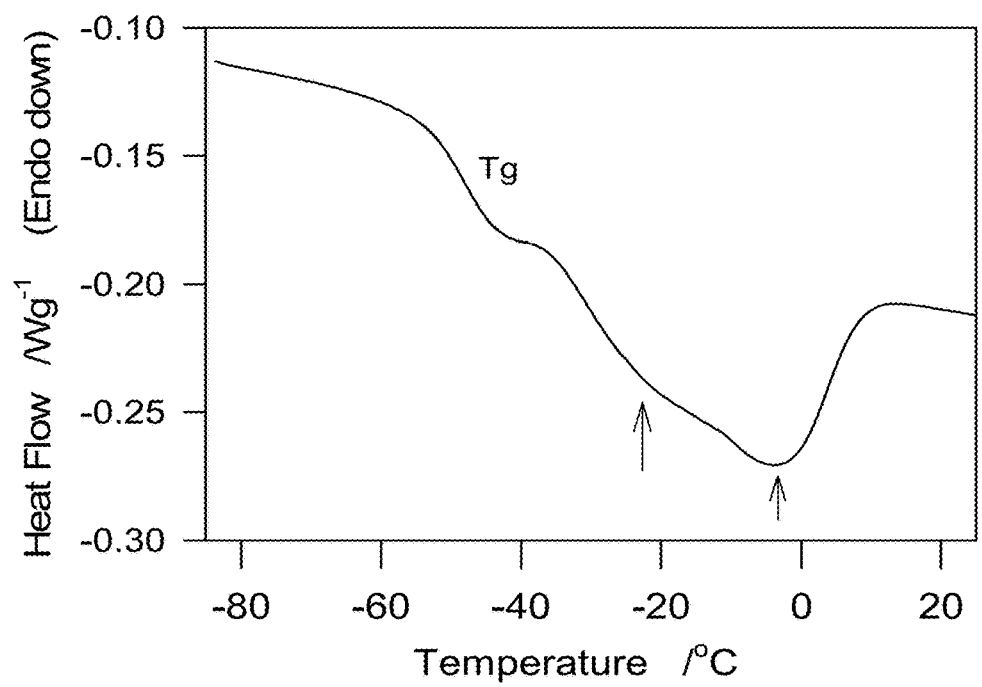
FIG. 31b depicts DSC thermograms of CMTAG Polyol obtained during subsequent heating at 5° C./min.

The crystallization and heating profiles (both at 5° C./min) of CMTAG Polyol are shown in FIG. 31a and FIG. 31b, respectively. The corresponding thermal data are listed in Table 12. The onset temperature of crystallization (~−1.9° C.) and offset temperature of melting (8.3° C.) indicate that CMTAG Polyol is liquid at sub ambient temperature. The two main exothermic events that were observed in the cooling thermogram (P1 and P2 in FIG. 31a) are associated with two different fractions of the CMTAG Polyol.

The heating thermogram of the CMTAG Polyol displayed a glass transition at −51° C. followed with an endotherm made of two peaks at −25 and −3.8° C. (arrows in FIG. 31). The two endothermic events are associated with the melting of the two fractions that have been detected in the cooling thermogram. Note that the heating thermograms of the CMTAG Polyol did not display any exotherm, indicating that polymorphic transformation mediated by melt does not occur with the CMTAG Polyol.

TABLE 12

Thermal data of CMTAG obtained on cooling and heating. Onset ($T_{on}$), offset ($T_{off}$), and peak temperatures ($T_{1-2}$), glass transition temperature ($T_g$), Enthalpy of crystallization ($\Delta H_C$), Enthalpy of melting ($\Delta H_M$)

| | Temperature (° C.) | | | | $\Delta H_C$ (J/g) |
|---|---|---|---|---|---|
| Cooling | $T_{on}$ | $T_1$ | $T_2$ | $T_{off}$ | $\Delta H_C$ |
| Sample 1 | −1.7 | −8.4 | −34.5 | −61.3 | 32.6 |
| Sample 2 | −1.9 | −7.5 | −32.6 | −59.7 | 36.4 |
| Average | −1.8 ± 0.1 | −8.0 ± 0.6 | 33.6 ± 1.3 | −60.5 ± 1.1 | 33.5 ± 0.8 |
| Heating | $T_{on}$ | $T_1$ | $T_g$ | $T_{off}$ | $\Delta H_M$ |
| Sample 1 | −41.1 | −3.5 | −53.6 | 7.9 | 17.6 |
| Sample 2 | −35.5 | −4.13 | −48.1 | 8.6 | 21.8 |
| Average | −38.3 ± 2.8 | −3.8 ± 0.4 | −50.9 ± 3.9 | 8.3 ± 0.4 | 19.7 ± 2.9 |

Flow Behavior and Viscosity of MTAG Polyol

Figure 32A:
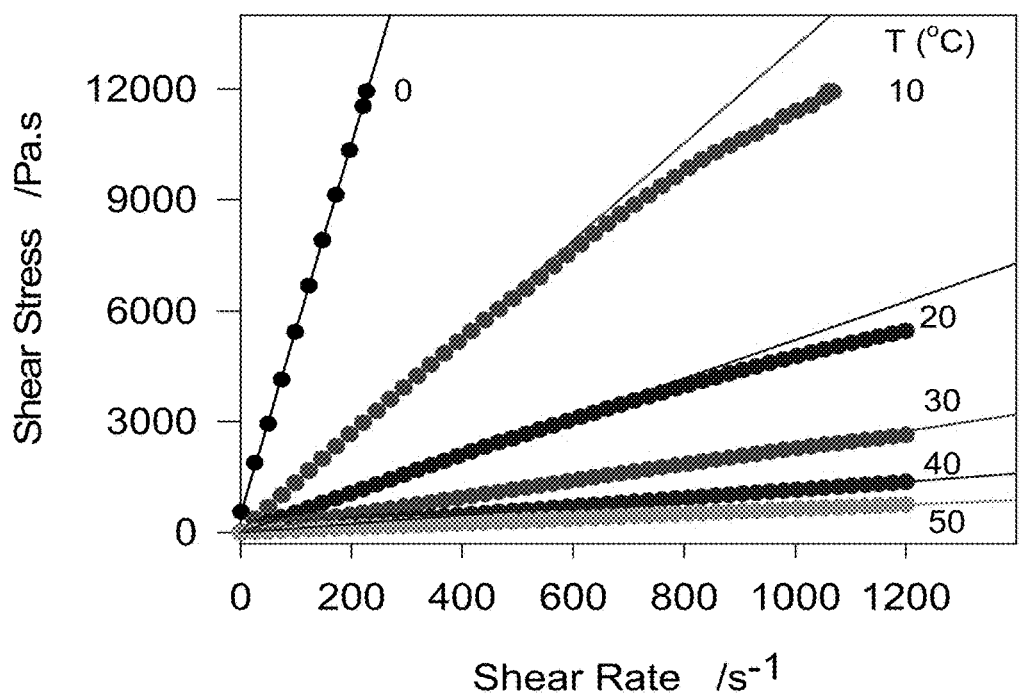
FIG. 32a depicts shear rate versus shear stress curves of CMTAG Polyol measured at 0 to 50° C.
Figure 32B:
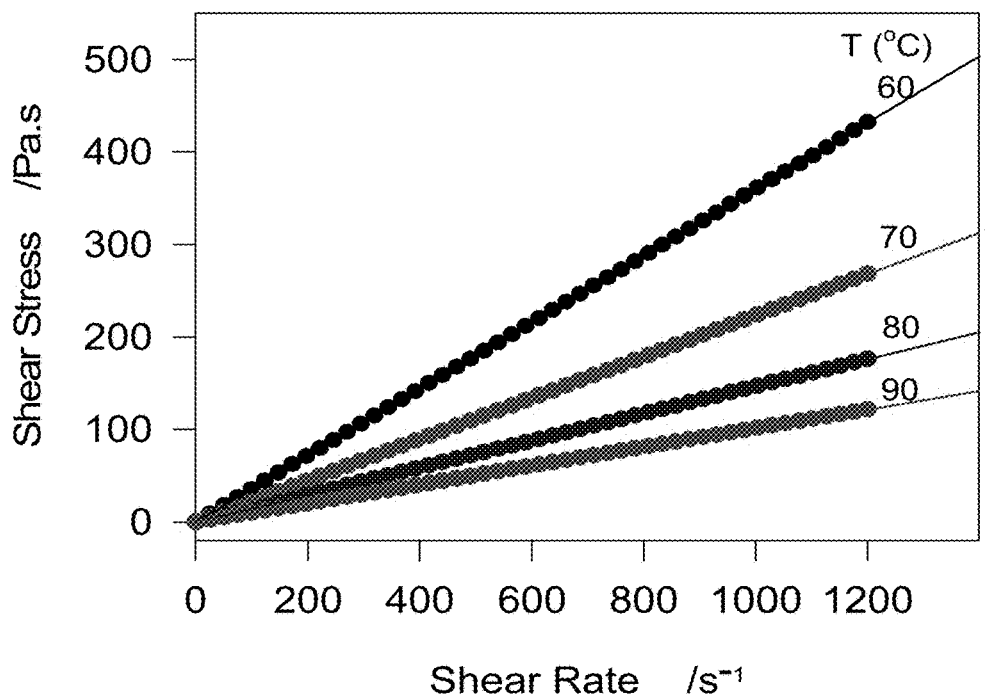
FIG. 32b depicts shear rate versus shear stress curves of CMTAG Polyol measured at 60 to 90° C.
Figure 33:
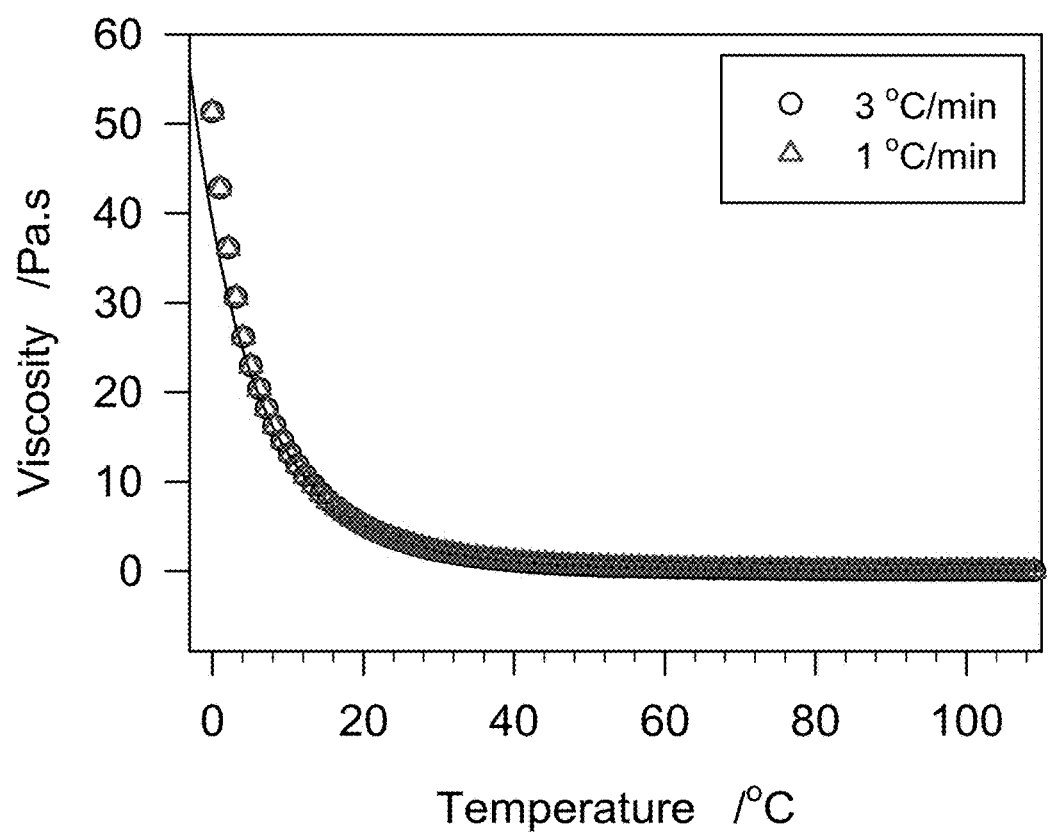
FIG. 33 depicts viscosity versus temperature curve of CMTAG Polyol obtained during cooling at 3 and 1° C./min.

FIGS. 32a and 32b show shear rate—shear stress curves of CMTAG Polyol obtained at different temperatures. Fits to the Herschel-Bulkley (eq. 1) model are included in FIG. 32. FIG. 33 shows the viscosity versus temperature curves obtained during cooling at 3 and 1° C./min. The power index values (n) obtained for CMTAG Polyol at temperatures above 30° C. were approximately equal to 1, indicating a Newtonian behavior in the whole range of the used shear rates. The data collected at 20° C. and below indicated that CMTAG Polyol was Newtonian only for shear rates lower than ~800 s$^{-1}$.

The viscosity versus temperature of liquid CMTAG polyols obtained using the ramp procedure presented exponential behavior of liquid hydrocarbons.

Solid Fat Content (SFC) of CMTAG Polyol

Figure 34:
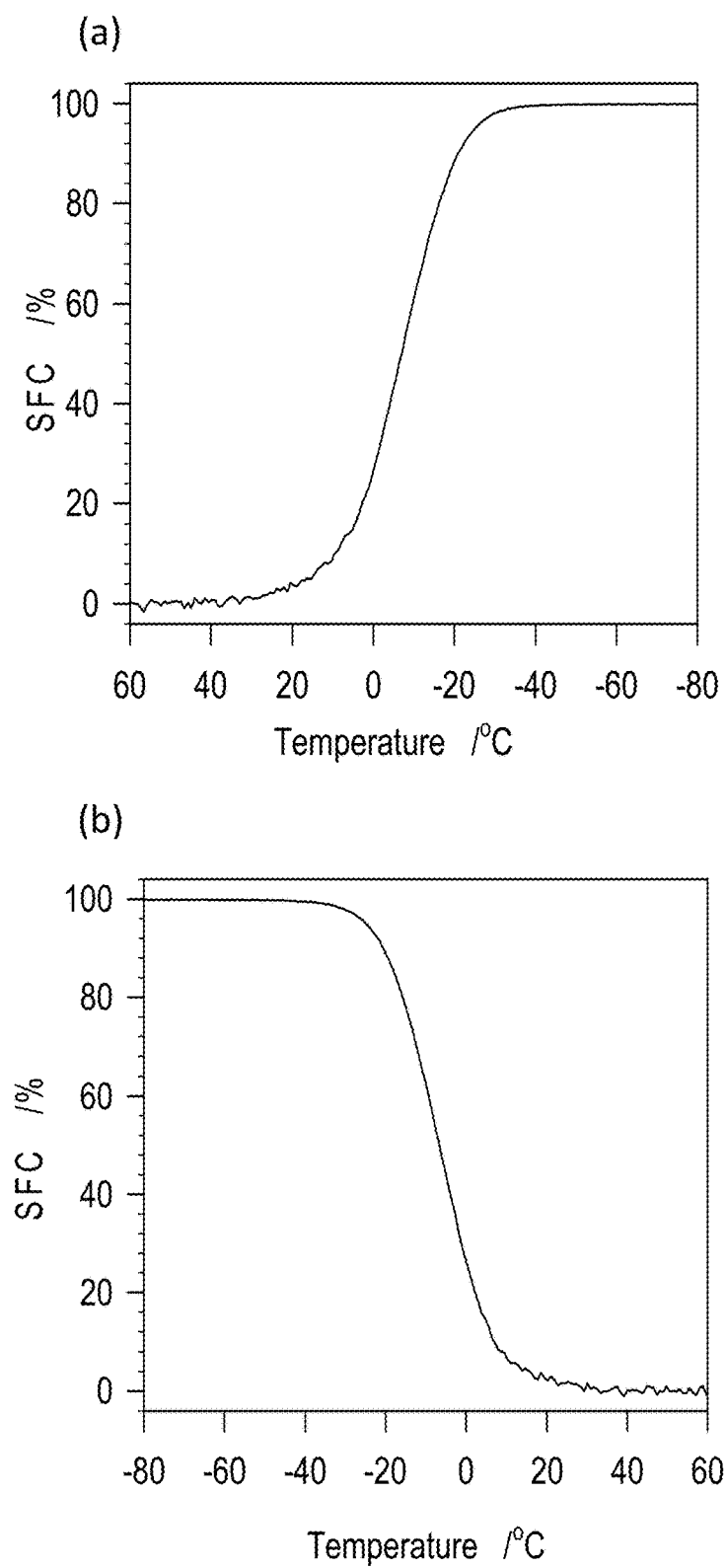
FIG. 34a depicts SFC of CMTAG Polyol obtained during cooling at 5.0° C./min.
FIG. 34b depicts SFC of CMTAG Polyol obtained during subsequent heating at 5° C./min.

Solid Fat Content (SFC) cooling and heating (both at 5° C./min) cycles of CMTAG Polyol are shown in FIG. 34a and FIG. 34b, respectively. Both traces indicate that CMTAG remains liquid at temperatures close to ambient conditions. Unlike the DSC which presented two exothermic events, the SFC cooling curve of the CMTAG Polyol (FIG. 34a) presented only one segment, probably due to the formation of a gel phase along the crystal phase.

C. Polyurethane Foams from Polyols of CMTAG

Polyurethane Foam Polymerization

Polyurethanes are one of the most versatile polymeric materials with regards to both processing methods and mechanical properties. The proper selection of reactants enables a wide range of polyurethane (PU) elastomers, sheets, foams etc. Polyurethane foams are cross linked structures that may be prepared based on a polymerization addition reaction between organic isocyanates and polyols, as shown in Scheme 9 below. Such a reaction may also be commonly referred to as a gelation reaction.

Scheme 9. Formation of urethane linkage between isocynate group and OH group

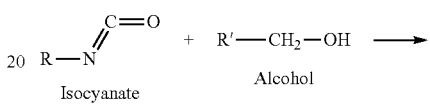

Isocyanate      Alcohol

-continued

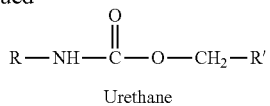

Urethane

A polyurethane is a polymer composed of a chain of organic units joined by the carbamate or urethane link. Polyurethane polymers may be formed by reacting one or more monomers having at least two isocyanate functional groups with at least one other monomer having at least two isocyanate-reactive groups, (i.e., functional groups which are reactive towards the isocyanate function). The isocyanate ("NCO") functional group is highly reactive and is able to react with many other chemical functional groups. In order for a functional group to be reactive to an isocyanate functional group, the group may have at least one hydrogen atom which is reactive to an isocyanate functional group. A polymerization reaction is presented in Scheme 10, using a hexol structure as an example.

Scheme 10. Preparation of cross linked polyurethane from MDI and CMTAG Polyol.

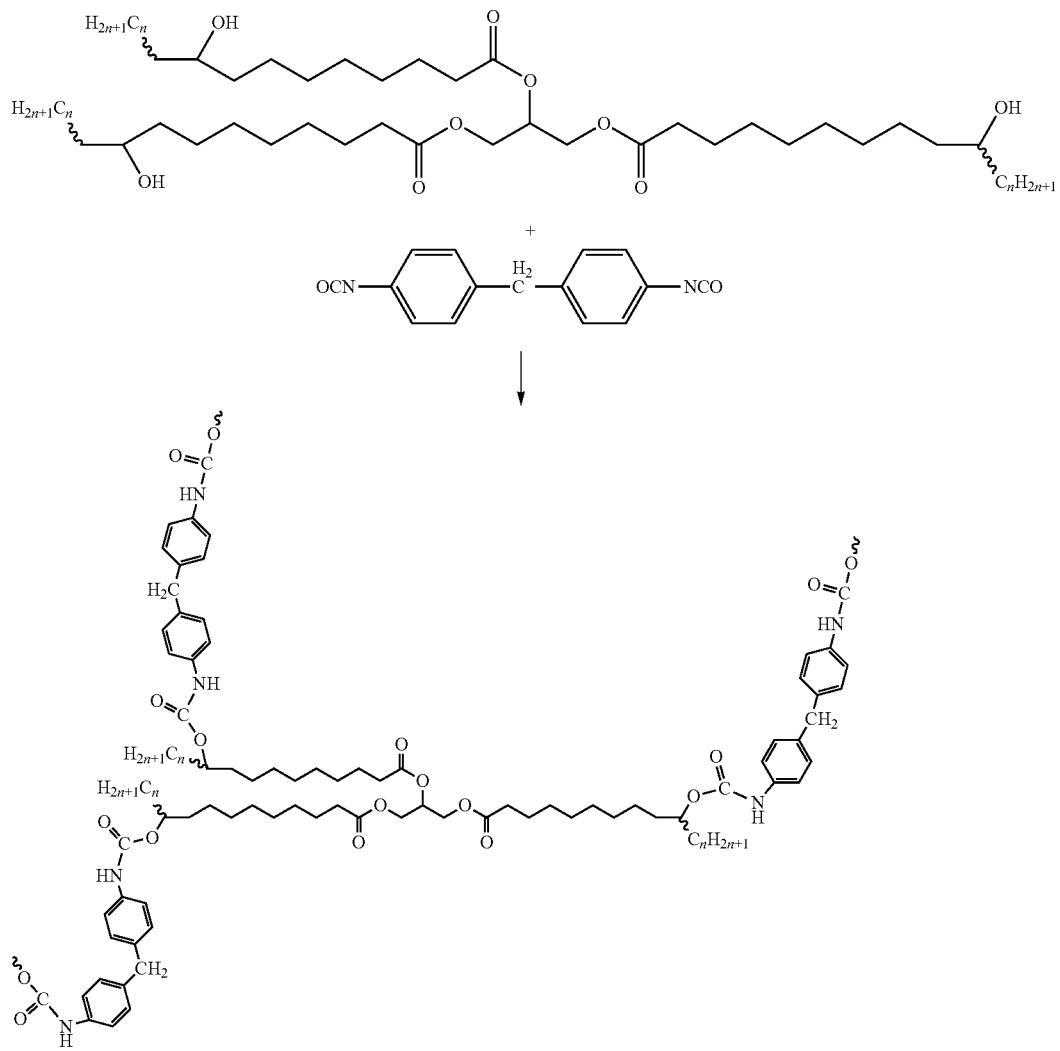

Triol structure is used as an example. n = 0, 2 or 8.

In addition to organic isocyanates and polyols, foam formulations often include one or more of the following non-limiting components: cross-linking components, blowing agents, cell stabilizer components, and catalysts. In some embodiments, the polyurethane foam may be a flexible foam or a rigid foam.

Organic Isocyanates

The polyurethane foams are derived from an organic isocyanate compound. In order to form large linear polyurethane chains, di-functional or polyfunctional isocyanates are utilized. Suitable polyisocyanates are commercially available from companies such as, but not limited to, Sigma Aldrich Chemical Company, Bayer Materials Science, BASF Corporation, The Dow Chemical Company, and Huntsman Chemical Company. The polyisocyanates may have a formula $R(NCO)_n$, where n is 1 to 10, and wherein R is 2 to 40 carbon atoms, and wherein R contains at least one aliphatic, cyclic, alicyclic, aromatic, branched, aliphatic- and alicyclic-substituted aromatic, aromatic-substituted aliphatic and alicyclic group. Examples of polyisocyanates include, but are not limited to diphenylmethane-4,4'-diisocyanate (MDI), which may either be crude or distilled; toluene-2,4-diisocyanate (TDI); toluene-2,6-diisocyanate (TDI); methylene bis (4-cyclohexylisocyanate ($H_{12}$MDI); 3-isocyanatomethyl-3,5,5-trimethyl-cyclohexyl isocyanate (IPDI); 1,6-hexane diisocyanate (HDI); naphthalene-1,5-diisocyanate (NDI); 1,3- and 1,4-phenylenediisocyanate; triphenylmethane-4,4',4''-triisocyanate; polyphenylpolymethylenepolyisocyanate (PMDI); m-xylene diisocyanate (XDI); 1,4-cyclohexyl diisocyanate (CHDI); isophorone diisocyanate; isomers and mixtures or combinations thereof.

Polyols

The polyols used in the foams described herein are metathesized triacylglycerol based polyols derived from certain natural oils, such as canola, rapeseed, olive, soy, sunflower, safflower, linseed, tung, mustard, camelina, hemp, algal, castor, and canola oil. The synthesis of the CMTAG Polyol was described earlier in this document.

Cross-Linking Components and Chain Extenders

Cross-linking components or chain extenders may be used if needed in preparation of polyurethane foams. Suitable cross-linking components include, but are not limited to, low-molecular weight compounds containing at least two moieties selected from hydroxyl groups, primary amino groups, secondary amino groups, and other active hydrogen-containing groups which are reactive with an isocyanate group. Crosslinking agents include, for example, polyhydric alcohols (especially trihydric alcohols, such as glycerol and trimethylolpropane), polyamines, and combinations thereof. Non-limiting examples of polyamine crosslinking agents include diethyltoluenediamine, chlorodiaminobenzene, diethanolamine, diisopropanolamine, triethanolamine, tripropanolamine, 1,6-hexanediamine, and combinations thereof. Diamine crosslinking agents may include twelve carbon atoms or fewer, more commonly seven or fewer. Other cross-linking agents include various tetrols, such as erythritol and pentaerythritol, pentols, hexols, such as dipentaerythritol and sorbitol, as well as alkyl glucosides, carbohydrates, polyhydroxy fatty acid esters such as castor oil and polyoxy alkylated derivatives of polyfunctional compounds having three or more reactive hydrogen atoms, such as, for example, the reaction product of trimethylolpropane, glycerol, 1,2,6-hexanetriol, sorbitol and other polyols with ethylene oxide, propylene oxide, or other alkylene epoxides or mixtures thereof, e.g., mixtures of ethylene and propylene oxides.

Non-limiting examples of chain extenders include, but are not limited to, compounds having hydroxyl or amino functional group, such as glycols, amines, diols, and water. Specific non-limiting examples of chain extenders include ethylene glycol, diethylene glycol, propylene glycol, dipropylene glycol, 1,4-butanediol, 1,3-butanediol, 1,5-pentanediol, neopentyl glycol, 1,6-hexanediol, 1,10-decanediol, 1,12-dodecanediol, ethoxylated hydroquinone, 1,4-cyclohexanediol, N-methylethanolamine, N-methylisopropanolamine, 4-aminocyclohexanol, 1,2-diaminoethane, 2,4-toluenediamine, or any mixture thereof.

Catalyst

The catalyst component can affect the reaction rate and can exert influence on the open celled structures and the physical properties of the foam. The proper selection of catalyst (or catalysts) appropriately balance the competing interests of the blowing and polymerization reactions. A correct balance is needed due to the possibility of foam collapse if the blow reaction proceeds relatively fast. On the other hand, if the gelation reaction overtakes the blow reaction, foams with closed cells might result and this might lead to foam shrinkage or 'pruning'. Catalyzing a polyurethane foam, therefore, involves choosing a catalyst package in such a way that the gas produced becomes sufficiently entrapped in the polymer. The reacting polymer, in turn, has sufficient strength throughout the foaming process to maintain its structural integrity without collapse, shrinkage, or splitting.

The catalyst component is selected from the group consisting of tertiary amines, organometallic derivatives or salts of, bismuth, tin, iron, antimony, cobalt, thorium, aluminum, zinc, nickel, cerium, molybdenum, vanadium, copper, manganese and zirconium, metal hydroxides and metal carboxylates. Tertiary amines may include, but are not limited to, triethylamine, triethylenediamine, N,N,N',N'-tetramethylethylenediamine, N,N,N',N'-tetraethylethylenediamine, N-methylmorpholine, N-ethylmorpholine, N,N,N',N'-tetramethylguanidine, N,N,N',N'-tetramethyl-1,3-butanediamine, N,N-dimethylethanolamine, N,N-diethylethanolamine. Suitable organometallic derivatives include di-n-butyl tin bis(mercaptoacetic acid isooctyl ester), dimethyl tin dilaurate, dibutyl tin dilaurate, dibutyl tin sulfide, stannous octoate, lead octoate, and ferric acetylacetonate. Metal hydroxides may include sodium hydroxide and metal carboxylates may include potassium acetate, sodium acetate or potassium 2-ethylhexanoate.

Blowing Agents

Polyurethane foam production may be aided by the inclusion of a blowing agent to produce voids in the polyurethane matrix during polymerization. The blowing agent promotes the release of a blowing gas which forms cell voids in the polyurethane foam. The blowing agent may be a physical blowing agent or a chemical blowing agent. The physical blowing agent can be a gas or liquid, and does not chemically react with the polyisocyanate composition. The liquid physical blowing agent may evaporate into a gas when heated, and may return to a liquid when cooled. The physical blowing agent may reduce the thermal conductivity of the polyurethane foam. Suitable physical blowing agents may include liquid carbon dioxide, acetone, and combinations thereof. Physical blowing agents may have a zero ozone depletion potential. Chemical blowing agents refers to blowing agents which chemically react with the polyisocyanate composition.

Suitable blowing agents may also include compounds with low boiling points which are vaporized during the exothermic polymerization reaction. Such blowing agents may be inert or they have low reactivity and therefore it is likely that they will not decompose or react during the polymerization reaction. Examples of blowing agents include, but are not limited to, water, carbon dioxide, nitrogen gas, acetone, and low-boiling hydrocarbons such as cyclopentane, isopentane, n-pentane, and their mixtures. Previously, blowing agents such as chlorofluorocarbons (CFCs), hydrofluorocarbons (HFCs), hydrochlorofluorocarbons (HCFCs), fluoroolefins (FOs), chlorofluoroolefins (CFOs), hydrofluoroolefins (HFOs), and hydrochlorfluoroolefins (HCFOs), were used, though such agents are not as environmentally friendly. Other suitable blowing agents include water that reacts with isocyanate to produce a gas, carbamic acid, and amine, as shown below in Scheme 11.

Scheme 11. Blowing reaction during the polymerization process

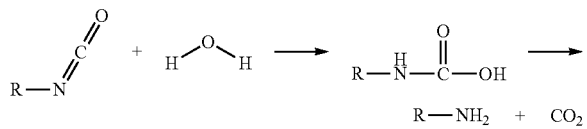

Various methods were adopted in the present study to produce rigid and flexible foams from CMTAG Polyol.

Cell Stabilizers

Cell stabilizers may include, for example, silicone surfactants or anionic surfactants. Examples of suitable silicone surfactants include, but are not limited to, polyalkylsiloxanes, polyoxyalkylene polyol-modified dimethylpolysiloxanes, alkylene glycol-modified dimethylpolysiloxanes, or any combination thereof. Suitable anionic surfactants include, but are not limited to, salts of fatty acids, salts of sulfuric acid esters, salts of phosphoric acid esters, salts of sulfonic acids, and combinations of any of these. Such surfactants provide a variety of functions, reducing surface tension, emulsifying incompatible ingredients, promoting bubble nucleation during mixing, stabilization of the cell walls during foam expansion, and reducing the defoaming effect of any solids added. Of these functions, a key function is the stabilization of the cell walls, without which the foam would behave like a viscous boiling liquid.

Additional Additives

If desired, the polyurethane foams can have incorporated, at an appropriate stage of preparation, additives such as pigments, fillers, lubricants, antioxidants, fire retardants, mold release agents, synthetic rubbers and the like which are commonly used in conjunction with polyurethane foams.

Flexible and Rigid Foam Embodiments

In some embodiments, the polyurethane foam may be a flexible foam, where such composition includes (i) at least one polyol composition derived from a natural oil (canola, rapeseed, olive, soy, sunflower, safflower, linseed, tung, mustard, camelina, hemp, algal, and castor oil) based metathesized triacylglycerols component; (ii) at least one polyisocyanate component, wherein the ratio of hydroxy groups in the at least one polyol to isocyanate groups in the at least one polyisocyanate component is less than 1; (iii) at least one blowing agent; (iv) at least one cell stabilizer component; and (v) at least one catalyst component; wherein the composition has a wide density range, which can be 85 $kgm^{-3}$ to 260 $kgm^{-3}$. In such flexible foam compositions, the relative amounts of each particular component may be tailored to the particular needs of an end user, as understood by a person skilled in the art. In some instances, the relative amounts of each component, or the ratios related thereto, may be greater or lesser than those presented herein, as understood by a person skilled in the art.

In other embodiments, the polyurethane foam may be a rigid foam, where the composition includes (i) at least one polyol derived from a natural oil (canola, rapeseed, olive, soy, sunflower, safflower, linseed, tung, mustard, camelina, hemp, algal, and castor oil) based metathesized triacylglycerols component; (ii) at least one polyisocyanate component, wherein the ratio of hydroxy groups in the at least one polyol to isocyanate groups in the at least one polyisocyanate component is less than 1; (iii) at least one cross-linking component (iv) at least one blowing agent; (v) at least one cell stabilizer component; and (vi) at least one catalyst component; wherein the composition has a wide density range, which can be 85 $kgm^{-3}$ to 260 $kgm^{-3}$. In such rigid foam compositions, the relative amounts of each particular component may be tailored to the particular needs of an end user, as understood by a person skilled in the art. In some instances, the relative amounts of each component, or the ratios related thereto, may be greater or lesser than those presented herein, as understood by a person skilled in the art.

Analytical Methods for CMTAG Polyol Foam Analysis

The CMTAG Polyol foam was analyzed using different techniques. These techniques can be broken down into: (i) chemistry characterization techniques, including NCO value and Fourier Transform infrared spectroscopy (FTIR); and (ii) physical characterization methods, including thermogravimetric analysis (TGA), differential scanning calorimetry (DSC), scanning electron microscopy (SEM) and compressive test.

Chemistry Characterization Techniques of CMTAG Polyol Foam

The amount of reactive NCO (% NCO) for the crude diisocyanates was determined by titration with dibutylamine (DBA). MDI (2±0.3 g) was weighed into 250 ml conical flasks. 2N DBA solution (20 ml) was pipetted to dissolve MDI. The mixture is allowed to boil at 150° C. until the vapor condensate is at an inch above the fluid line. The flasks were cooled to RT and rinsed with methanol to collect all the products. 1 ml of 0.04% bromophenol blue indicator is then added and titrated against 1N HCl until the color changes from blue to yellow. A blank titration using DBA is also done.

The equivalent weight (EW) of the MDI is given by Eq. 2

$$EW = \frac{W \times 1000}{(V_1 - V_2) \times N} \quad \text{Eq. 2}$$

where W is the weight of MDI in g, $V_1$ and $V_2$ are the volume of HCl for the blank and MDI samples, respectively. N is the concentration of HCl. The NCO content (%) is given by Eq. 3:

$$\% \ NCO \ \text{content} = \frac{42}{EW} \times 100 \quad \text{Eq. 3}$$

FTIR spectra were obtained using a Thermo Scientific Nicolet 380 FT-IR spectrometer (Thermo Electron Scientific Instruments, LLC, USA) equipped with a PIKE MIRacle™ attenuated total reflectance (ATR) system (PIKE Technologies, Madison, Wis., USA.). Foam samples were loaded onto the ATR crystal area and held in place by a pressure arm, and sample spectra were acquired over a scanning range of 400-4000 $cm^{-1}$ for 32 repeated scans at a spectral resolution of 4 $cm^{-1}$.

Physical Characterization Techniques of CMTAG Polyol Foam

TGA was carried out on a TGA Q500 (TA Instruments, DE, USA) equipped with a TGA heat exchanger (P/N 953160.901). Approximately 8.0-15.0 mg of sample was loaded in the open TGA platinum pan. The sample was heated from 25 to 600° C. under dry nitrogen at a constant rate of 10° C./min.

DSC measurements were run on a Q200 model (TA Instruments, New Castle, Del.) under a nitrogen flow of 50 mL/min. CMTAG Polyol foam samples of 3.0 to 6.0 (±0.1) mg were run in hermetically sealed aluminum DSC pans. In order to obtain a better resolution of the glass transition, CMTAG Polyol foams were investigated using modulated DSC following ASTM E1356-03 standard. The sample was first equilibrated at −90° C. and heated to 150° C. at a constant rate of 5.0° C./min (first heating cycle), held at 150° C. for 1 min and then cooled down to −90° C. with a cooling rate of 5° C./min, and subsequently reheated to 150° C. at the same rate (second heating cycle). Modulation amplitude and period were 1° C. and 60 s, respectively. The "TA Universal Analysis" software was used to analyze the DSC thermograms.

A scanning electron microscope (SEM), model Tescan Vega II, was used under standard operating conditions (10 keV beam) to examine the pore structure of the foams. A sub-sample of approximately 2 cm×2 cm and 0.5 cm thick was cut from the centre of each sample. The sample was coated with a thin layer of carbon (~30 nm thick) using an Emitech K950X turbo evaporator to provide electrical conductivity in the SEM chamber and prevent the buildup of electrons on the surface of the sample. All images were acquired using a secondary electron detector to show the surface features of the samples.

The compressive strength of the foams was measured at room temperature using a texture analyzer (Texture Technologies Corp, NJ, USA). Samples were prepared in cylindrical Teflon molds of 60-mm diameter and 36-mm long. The cross head speed was 3.54 mm/min with a load cell of 500 kgf or 750 kgf. The load for the rigid foams was applied until the foam was compressed to approximately 15% of its original thickness, and compressive strengths were calculated based on the 10% deformation and 6% deformation. The load for the flexible foams was applied until the foam was compressed to approximately 65% of its original thickness, and compressive strengths were calculated based on 5, 10 and 25% deformation.

Polymerization Conditions

Materials

The materials used to produce the foams are listed in Table 13. The CMTAG Polyols were obtained from MTAG of canola oil using the epoxidation and hydrogenation synthesis route or the epoxidation and hydroxylation synthesis route, as described above. The foam will be referred simply as CMTAG Polyol foam. A commercial isocyanate, methylene diphenyl diisocyanate (MDI) and a general purpose silicone surfactant, polyether-modified (TEGOSTAB B-8404, Goldschmidt Chemical Canada) were used in the preparation. The physical properties of the crude MDI as provided by the supplier are reported in Table 15.

TABLE 13

Materials used in the polymerization reaction

| Material | |
|---|---|
| Polyol | CMTAG Polyol |
| Isocyanate | Crude MDI[a] |
| Catalyst | DBTDL[b], 95% |
|  | DMEA[c], 99.5% |
| Cross linker | Glycerin, 99.5% |
| Surfactant | TEGOSTAB ® B-8404[d] |
| Blowing agent | $CO_2$ from addition of 2% deionized $H_2O$ |

[a]MDI: Diphenylmethane diisocynate, from Bayer Materials Science, Pittsburgh, PA
[b]DBTDL: Dibutin Dilaurate, main catalyst, from Sigma Aldrich, USA
[c]DMEA: N,N-Dimethylethanolamine, co-catalyst, from Fischer Chemical, USA
[d]TEGOSTAB ® B-8404, Polyether-modified, a general-purpose silicone surfactant, from Goldschmidt Chemical, Canada The hydroxyl value (OH value) and acid value of the CMTAG Polyol, measured using ASTM D1957-86 and ASTM D4662-03, respectively, are listed in Table 14. There were no free fatty acids detected by $^1$H-NMR. There was also no signal that can be associated with the loss of free fatty acids in the TGA of the CMTAG Polyol. The acid value reported in Table 14 was probably due to the hydrolysis of CMTAG Polyol during the actual titration, which uses strong base as the titrant, with the result that the actual titration causes hydrolysis.

Figure 35:
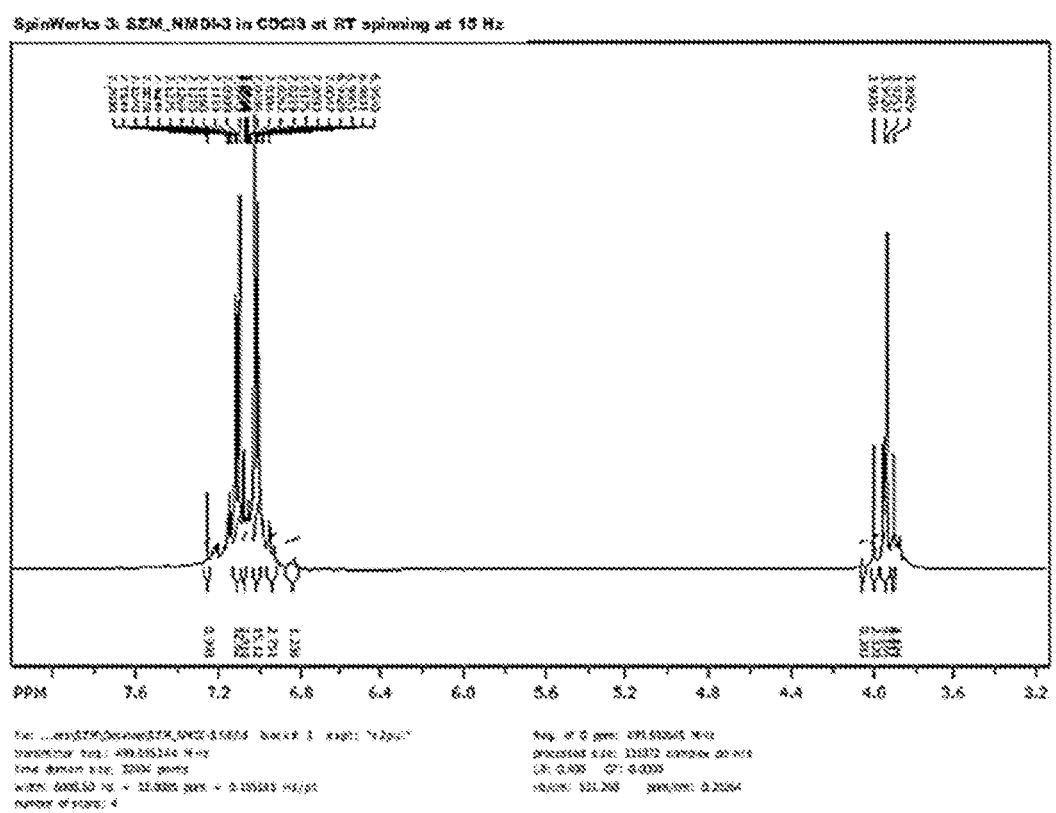
FIG. 35 depicts $^1$H-NMR spectrum of crude MDI.

FIG. 35 shows the $^1$H-NMR spectrum of crude MDI. Table 16 shows the corresponding chemical shift values.

TABLE 14

OH and acid value of CMTAG Polyol

|  | OH-value (g/100 g) | Acid-value (mg KOH/g) |
|---|---|---|
| CMTAG Polyol | 170 | <2 |

TABLE 15

Physical properties of crude MDI

| Property | Value |
|---|---|
| Form | Dark brown liquid |
| Boiling Point (° C.) | 208 |
| NCO content (% wt.) | 31.5 |
| Equivalent weight | 133 |
| Functionality | 2.4 |
| Viscosity at 25° C. (mPas) | 200 |
| Bulk density (kgm$^{-3}$) | 1234 |
| Composition | Polymeric MDI: 40-50% |
|  | (4,4' diphenylmethane diisocyanate): |
|  | 30-40% MDI mixed isomers: 15-25% |

TABLE 16

$^1$H-NMR data of crude MDI

|  | NCO at position 2 of Benzene | NCO at 4 position of Benzene | | $CH_2$ in Isomers | | | | |
|---|---|---|---|---|---|---|---|---|
| Protons | (CH=CH) | m(CH=CH) | o(CH=CH) | 2,2' | 2,4' | 4,4' | Others | Oligomers |
| (ppm) | 7.1386-7.1599 | 7.0779-7.1275 | 7.0175-7.0384 | 4.04 | 3.9904 | 3.9420 | 3.8929 | 3.9253 |

Synthesis of Foams from CMTAG Polyol

Rigid and flexible polyurethane foams of different densities were obtained using appropriate recipe formulations. The amount of each component of the polymerization mixture was based on 100 parts by weight of total polyol. The amount of MDI was taken based on the isocyanate index 1.2. All the ingredients, except MDI, were weighed into a beaker and MDI was added to the beaker using a syringe, and then mechanically mixed vigorously for ~20 s. At the end of the mixing period, mixed materials was added into a cylindrical Teflon mold (60 mm diameter and 35 mm long) which was previously greased with silicone release agent and sealed with a hand tightened clamp. The sample was cured for four (4) days at 40° C. and post cured for one (1) day at room temperature.

Rigid foam formulation was determined based on a total hydroxyl value of 450 mg KOH/g according to teachings known in the field. Table 17a presents the formulation recipe used to prepare the rigid foams. Note that in this case, around 16.2 parts of glycerin were added into the reaction mixture in order to reach the targeted hydroxyl value of 450 mg KOH/g. Flexible foam formulation was based on a total hydroxyl value of 170 mg KOH/g according to teachings known in the field. Table 17b presents the formulation recipe used to prepare the flexible foams. In this case, no glycerin was added into the reaction mixture, and the catalyst amount was fixed to 0.1 parts for proper control of the polymerization reaction.

TABLE 17a

Formulation Recipe for Rigid Foams

| Ingredient | Parts |
|---|---|
| CMTAG Polyol | 100 |
| OH:NCO ratio | 1:1.2 |
| Glycerin | 15.3 |
| Water | 2 |
| Surfactant | 2 |
| Catalyst | 1 |
| Co-catalyst | 1 |
| Mixing Temperature (° C.) | 40 |
| Oven Temperature (° C.) | 40 |

TABLE 17b

Formulation Recipe for Flexible Foams

| Ingredient | Parts |
|---|---|
| CMTAG Polyol | 100 |
| OH:NCO ratio | 1:1.2 |
| Glycerin | 0 |
| Water | 2 |
| Surfactant | 2 |
| Catalyst | 0.1 |
| Co-catalyst | 0.1 |
| Mixing Temperature (° C.) | 40 |
| Oven Temperature (° C.) | 40 |

CMTAG Polyol Foam Produced

Figure 36A:
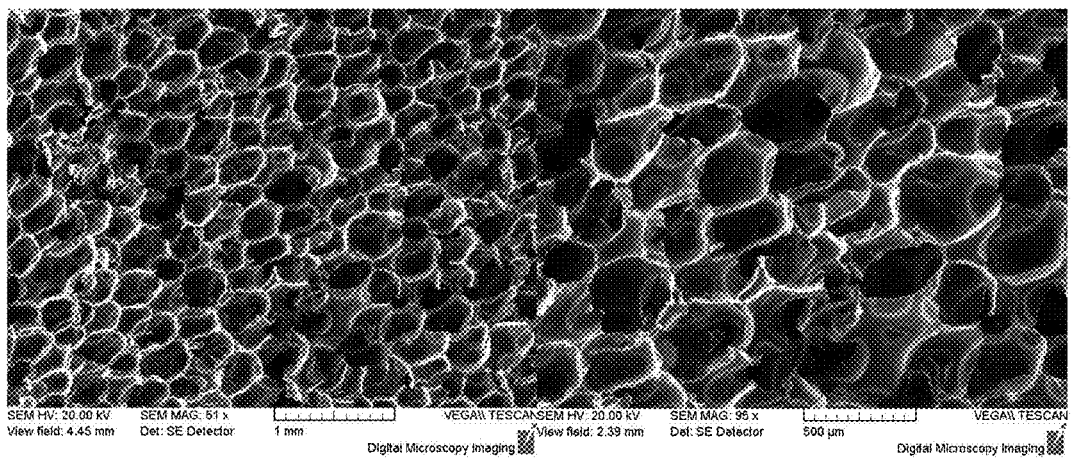
FIG. 36a depicts SEM micrographs of rigid CMTAG Polyol foams.
Figure 36B:
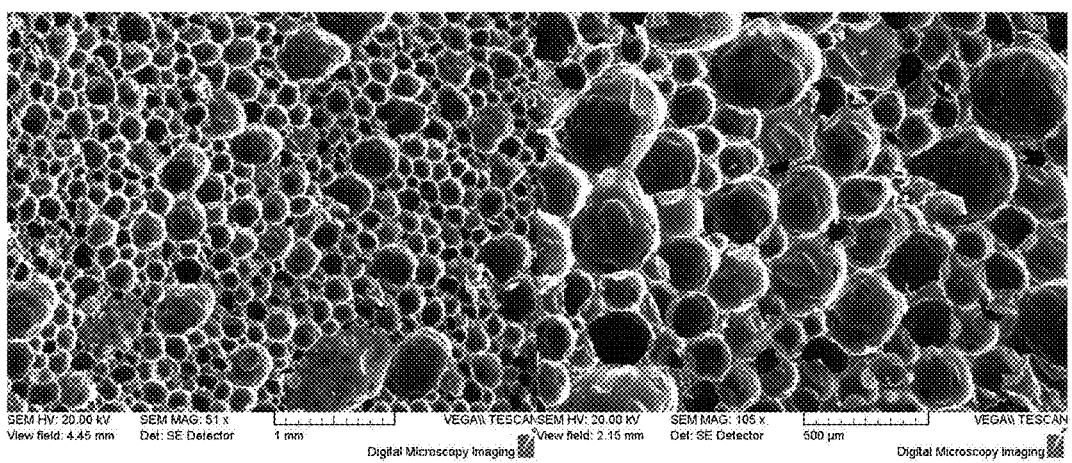
FIG. 36b depicts SEM micrographs of flexible CMTAG Polyol foams.

One rigid foam with density of 166 kg/m$^3$ (C-RF166) and two flexible foams with densities of 151 and 160 kg/m$^3$ (C-FF151 and C-FF160, respectively) were prepared from the CMTAG Polyol using crude MDI. Both rigid and flexible foams presented a very regular and smooth appearance (pictures not shown). The foams presented a homogenous closed cell structure elucidated through SEM micrographs, examples of which are shown in FIGS. 36a and 36b for the rigid and flexible CMTAG Polyol foams, respectively.

FTIR of CMTAG Polyol Foam

Figure 37:
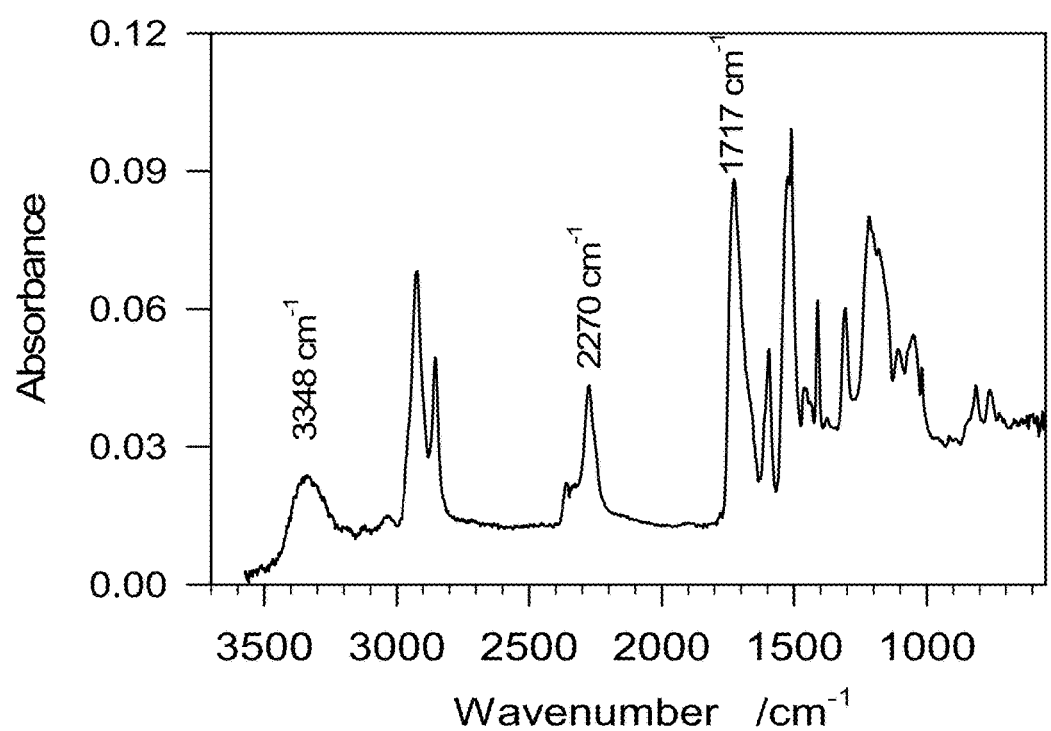
FIG. 37 depicts a FTIR spectrum of CMTAG Polyol foams.

An example of a FTIR spectrum of CMTAG Polyol Foams is shown in FIG. 37. Table 18 lists the characteristic vibrations of the foams. The broad absorption band observed at 3300-3400 cm$^{-1}$ in the foam is characteristic of NH group associated with the urethane linkage. The weak band at 2270 cm$^{-1}$ indicates that free NCO are present in the foam. The overlapping peaks between 1710 and 1735 cm$^{-1}$ suggest the formation of urea, isocyanurate and free urethane in the CMTAG Polyol foams.

The CH$_2$ stretching vibration is clearly visible at 2800-3000 cm$^{-1}$ region in the spectra. The band centered at 1700 cm$^{-1}$ is characteristic of C=O, which demonstrates the formation of urethane linkages. The band at 1744 cm$^{-1}$ is attributed to the C=O stretching of the ester groups. The sharp band at 1150-1160 cm$^{-1}$ and 1108-1110 cm$^{-1}$ are the O—C—C and C—C(=O)—O stretching bands, respectively, of the ester groups. The band at 1030-1050 cm$^{-1}$ is due to CH$_2$ bend.

TABLE 18

FTIR data of CMTAG Polyol foam

| Moiety | Wavelengths (cm$^{-1}$) |
|---|---|
| H-bonded and free N—H groups | 3300-3400 |
| Free NCO | 2270 |
| Urea | 1717 |
| Isocyanurate | 1710 |
| Free Urethane | 1735 |

Physical Properties of CMTAG Polyol Foams
Thermal Stability of CMTAG Polyol Foams The thermal stability of the CMTAG Polyol foams was determined by TGA. Examples of TGA and DTG curves of rigid and flexible CMTAG Polyol foams are shown in FIGS. 38a and 38b, respectively. Temperature of degradation determined at 1, 5 and 10% weight loss ($T_{1\%}$, $T_{5\%}$ and $T_{10\%}$, respectively), and DTG peak temperatures ($T_{D1-3}$) of rigid and flexible CMTAG Polyol foams are listed in Table 19.

The initial step of decomposition indicated by the DTG peak at 299° C. with a total weight loss of 17% is due to the degradation of urethane linkages, which involves dissociations to the isocyanate and the alcohol, amines and olefins or to secondary amines. The second decomposition step in the range of 330 to 430° C. and indicated by the DTG peak at 360° C. with a total weight loss of 60%, was due to degradation of the ester groups. The degradation steps at higher temperatures were attributed to the degradation of more strongly bonded fragments.

TABLE 19

Thermal degradation data of CMTAG Polyol foams. Temperature of degradation determined at 1, 5 and 10% weight loss ($T_{1\%}$, $T_{5\%}$ and $T_{10\%}$, respectively), and DTG peak temperatures ($T_{D1-3}$) of CMTAG Polyol foams.

|  |  | $T_{1\%}^d$ | $T_{5\%}^d$ | $T_{10\%}^d$ | $T_{D1}$ | $T_{D2}$ | $T_{D3}$ |
|---|---|---|---|---|---|---|---|
| Rigid Foam | Temperature (° C.) | 124 | 252 | 272 | 280 | 310 | 454 |
|  | Weight loss (%) | 1 | 5 | 10 | 12 | 25 | 60 |
| Flexible Foam | Temperature (° C.) | 72 | 258 | 280 | 299 | 342 | 461 |
|  | Weight loss (%) | 1 | 5 | 10 | 16 | 32 | 60 |

Thermal Transition Behavior of CMTAG Polyol Foam

A curves obtained from the modulated DSC during the second heating cycle of the rigid and flexible CMTAG Polyol foams are shown in FIGS. 39a and 39b, respectively. Table 20 lists the glass transition temperature ($T_g$) of the flexible CMTAG Polyol foams produced. No $T_g$ has been detected in the rigid foam in the range of temperatures studied.

TABLE 20

Glass transition temperature ($T_g$) of CMTAG Polyol foams produced. C-FF160 and C-FF151: Flexible CMTAG Polyol foam with density of 160 and 151 kg/m³, respectively

| Foam | $T_g$ (° C.) |
|---|---|
| C-RF166 | — |
| C-FF160 | 30.4 |
| C-FF160 | 32.1 |

Compressive Strength of Rigid CMTAG Polyol Foams

Figure 40:
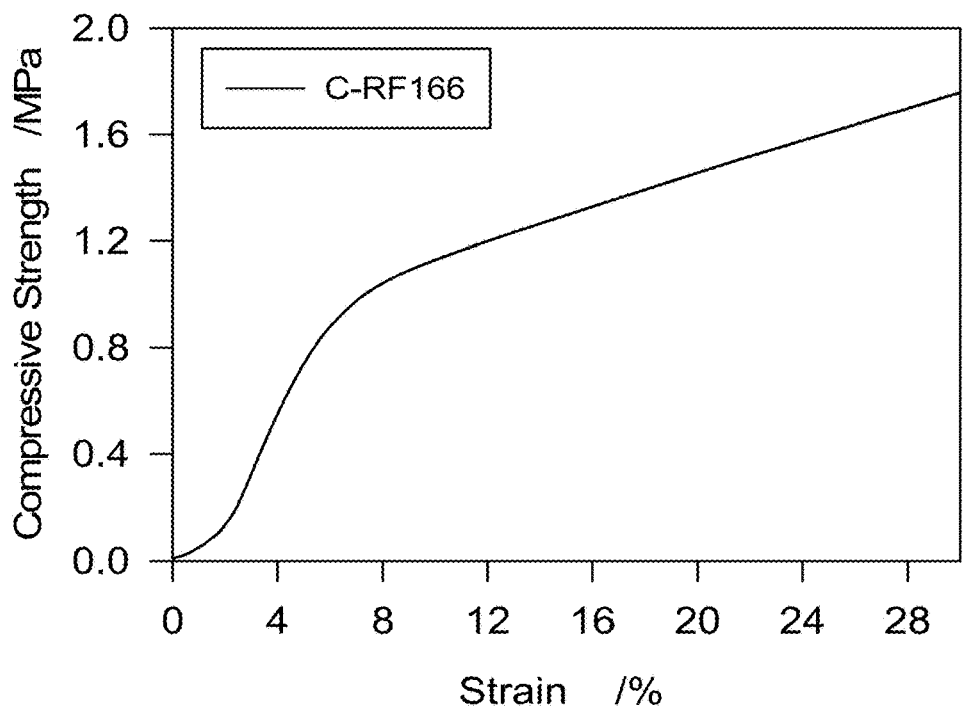
FIG. 40 depicts stress versus strain curve of rigid CMTAG Polyol foam.

The strength of the foams were characterized by the compressive stress-strain measurements. Stress strain curve of C-RF166 rigid foam is shown in FIG. 40. The compressive strength values at 6, 10 and 25% deformation for the rigid CMTAG Polyol foam are listed in Table 21.

TABLE 21

Compressive strength at 6, 10 and 25% deformation of rigid CMTAG Polyol foam

| Strain (%) | Compressive strength (MPa) |
|---|---|
| 6 | 0.88 |
| 10 | 1.13 |
| 25 | 1.61 |

The compressive strength is highly dependent on the cellular structure of the foam. In the case of the rigid CMTAG Polyol foam, the high mechanical strength of the foams was due to compact and closed cells as shown in FIG. 36a. The cell density from the SEM micrographs is ~25 cells per mm². The elongation of the cells are due to the direction of rise and the boundaries caused by the walls of the cylindrical mold.

Compressive Strength of Flexible CMTAG Polyol Foams

FIG. 41 shows the compressive strength versus strain of flexible CMTAG Polyol foams produced using crude MDI. Table 22 lists the compressive strength at 10, 25 and 50% deformation of the flexible CMTAG Polyol foams. As can be seen in FIG. 41, the compressive strength of the flexible CMTAG Polyol foams increased with density.

TABLE 22

Compressive strength value at 10, 25 and 50% deformation of flexible CMTAG foams

| Foam | Density (kg/m³) | Compressive Strength (MPa) at Strain (%) | | |
|---|---|---|---|---|
| | | 10 | 25 | 50 |
| C-FF151 | 151 | 0.32 | 0.35 | 0.57 |
| C-FF160 | 160 | 0.34 | 0.48 | 0.71 |

FIG. 42 shows the percentage of recovery of flexible CMTAG Polyol foams as a function of time. Table 23 lists the recovery values after 48 hours. Note that ~75-80% recovery was achieved after 10 min. The flexible CMTAG Polyol foam having a density of 151 kg/m³ presented 90% recovery in less than 20 min.

TABLE 23

Recovery (%) values of C-FF160 and C-FF150 after 48 hours. %. C-FF160 and C-FF150: CMTAG Polyol flexible foam having a density of 160 and 151 kg/m³, respectively.

| Foam | Density (kg/m³) | Recovery (%) |
|---|---|---|
| C-FF151 | 151 | 90 |
| C-FF160 | 160 | 82 |

D. Comparative Study of Canola and Palm Oils MTAG Foams

The rigid foam from CMTAG Polyol having a density of 166 kg/m³ (C-RF166) was compared with a rigid foam from palm oil MTAG Polyol (PMTAG Polyol) with a similar density of 165 kg/m³ (P-RF165). The flexible foam from CMTAG Polyol with a density of 160 kg/m³ (C-FF160) was compared with a flexible foam from PMTAG Polyol having the same density (P-FF160).

Comparison of Rigid Canola and Palm Oil MTAG Foams

Stress versus strain curves of rigid CMTAG and PMTAG Polyol foams (C-RF166 and P-RF165) are shown in FIG. 43. Note that recipe for the preparation of P-RF166 the rigid foam from PMTAG (Table 24) and CMTAG polyols (Table 17a) differed only by the amount of glycerin used in the formulations.

Table 25 lists the compressive strength values of both rigid foams at 6, 10 and 25% deformation. As can be seen, P-RF165 presented a higher compressive strength at strains lower than 5.2% and a lower compressive strength at higher strains.

TABLE 24

Formulation recipe for rigid palm oil MTAG (PMTAG) Polyol foam

| Ingredients | Parts |
|---|---|
| PMTAG polyol | 100 |
| OH:NCO ratio | 1:1.2 |
| Glycerine | 16.2 |
| Water | 2 |
| Surfactant | 2 |
| Catalyst | 1 |
| Co-catalyst | 1 |
| Mixing Temperature (° C.) | 40 |
| Oven temperature (° C.) | 40 |

TABLE 25

Compressive strength value of rigid CMTAG and
PMTAG Polyols foams at 6 and 10% deformation
C-RF166: rigid CMTAG Polyol foam with density = 166 kg/m³;
P-RF165: rigid PMTAG Polyol foam with density = 165 kg/m³

| Strain (%) | Stress (MPa) | | |
|---|---|---|---|
| | 6 | 10 | 25 |
| C-RF166 | 0.88 | 1.13 | 1.61 |
| P-RF165 | 0.84 | 1.00 | 1.16 |

Comparison of Flexible Canola and Palm Oils MTAG Foams

FIG. 44 shows the stress versus strain plots of flexible CMTAG Polyol and PMTAG Polyol foams (C-FF160 and P-FF160, respectively), and Table 26 lists their compressive strength values at 10, 25 and 50% deformation. As can be seen, the flexible foam made from PMTAG Polyol shows a higher compressive strength than the flexible foam made from CMTAG Polyol at all deformations. Note that the flexible PMTAG Polyol foam was polymerized using the same recipe as the flexible CMTAG Polyol foam (Table 17b).

TABLE 26

Compressive strength values of flexible CMTAG Polyol and
PMTAG Polyol foams at 10, 25 and 50% deformation
C-FF160: flexible CMTAG Polyol foam having density of 160 kg/m³, and
P-FF160: flexible PMTAG Polyol foam having density of 160 kg/m³

| Foam | | Stress (MPa) | |
|---|---|---|---|
| | Strain (%) | C-FF160 | P-FF160 |
| | 10 | 0.34 | 0.61 |
| | 25 | 0.48 | 0.73 |
| | 50 | 0.71 | 1.02 |

FIG. 45 shows the recovery (%) of flexible CMTAG Polyol and PMTAG Polyol foams (C-FF160 and P-FF164, respectively) as a function of time. Table 27 lists their recovery (%) values after 48 hours. Note that both C-FF160 and P-FF160 achieved ~75 to 80% recovery after 10 min.

TABLE 27

Recovery (%) of flexible CMTAG Polyol
and PMTAG Polyol foams after 48 hours.
C-FF160: flexible CMTAG Polyol foam having density of 160 kg/m³, and
P-FF160: flexible PMTAG Polyol foam having density of 160 kg/m³

| Foam | Density (kg/m³) | Relaxation (%) |
|---|---|---|
| C-FF160 | 160 | 82 |
| P-FF164 | 164 | 83 |

The foregoing detailed description and accompanying figures have been provided by way of explanation and illustration, and are not intended to limit the scope of the invention or the appended claims. Many variations in the present embodiments illustrated herein will be apparent to one of ordinary skill in the art, and remain within the scope of the invention and their equivalents.

The invention claimed is:

1. A composition comprising a polyol wherein the polyol has the following structure

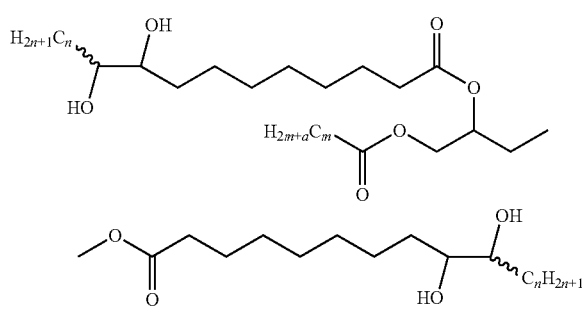

wherein:
n=1, 2, 3, 4, 5, 6, 7, 8, 9, 10, 11, or 12,
m=15 or 17,
a=−5, −3, −1, or 1, and
wherein the composition is prepared by a process comprising:
 i) metathesizing canola oil to obtain metathesized triacylglycerides; and
 ii) subjecting the canola oil metathesized triacylglycerides to epoxidation by mixing the canola oil metathesized triacylglycerides with formic acid in dichloromethane at 0° C. and adding hydrogen peroxide dropwise and mixing at 50° C. to obtain the epoxidized triacylglycerides; and
 iii) subsequently subjecting the epoxidized triacylglycerides to hydroxylation.

2. The composition of claim 1, further comprising the following structure:

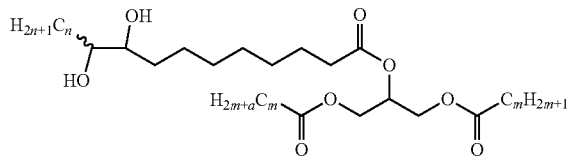

wherein:
n=2 or 8;
m=15 or 17;
a=−5, −3, −1, or 1.

3. The composition of claim 1, further comprising the following structure:

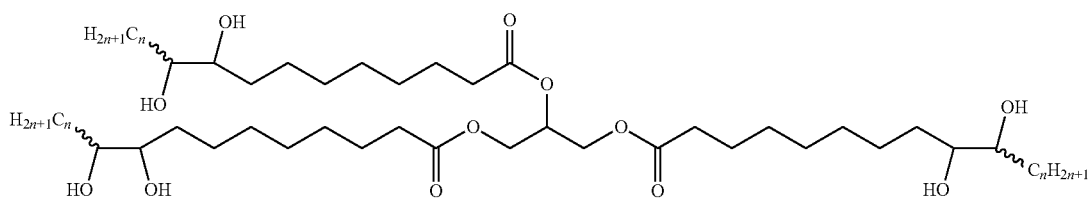

wherein:
  n=2 or 8;
  m=15 or 17;
  a=−5, −3, −1, or 1.
4. The composition of claim 1, further comprising the following structure:

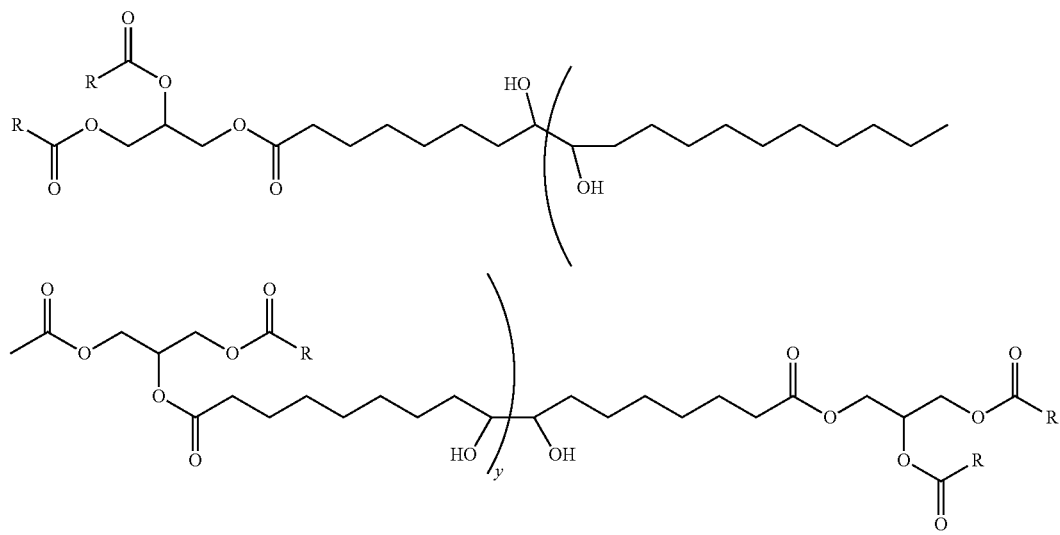

wherein:

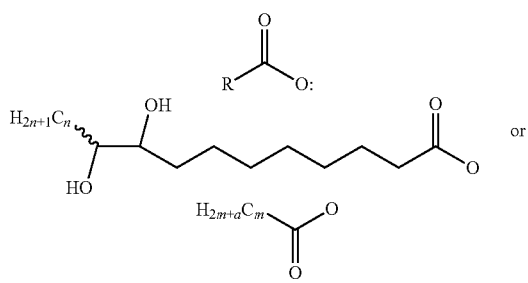

n=2 or 8;
  m=15 or 17;
  a=−5, −3, −1, or 1;
  y=0-8.
5. The composition of claim 1, wherein n is 2 or 8.
6. A flexible polyurethane foam prepared from a blend composition comprising:
  (i) the polyol composition of claim 1;
  (ii) at least one polyisocyanate component, wherein the ratio of hydroxy groups in the polyol composition to isocyanate groups in the at least one polyisocyanate component is less than 1;
  (iii) at least one blowing agent;
  (iv) at least one cell stabilizer component; and
  (v) at least one catalyst component.
7. The flexible polyurethane foam of claim 6, wherein the at least one polyisocyanate component comprises the formula $R(NCO)_n$, wherein n is 1 to 10, and wherein R is 2 to 40 carbon atoms, and wherein R contains at least one aliphatic, cyclic, alicyclic, aromatic, branched, aliphatic- and alicyclic-substituted aromatic, or aromatic-substituted aliphatic and alicyclic group.

8. The composition flexible polyurethane foam of claim 6, wherein:
  (i) the blowing agent is selected from the group consisting of water, carbon dioxide, nitrogen gas, chlorofluorocarbons (CFCs), hydrofluorocarbons (HFCs), hydrochlorofluorocarbons (HCFCs), fluoroolefins (FOs), chlorofluoroolefins (CFOs), hydrofluoroolefins (HFOs), hydrochlorfluoroolefins (HCFOs), acetone, and low-boiling hydrocarbons;
  (ii) the cell stabilizer component comprises a silicone surfactant or an anionic surfactant; and
  (iii) the catalyst component is selected from the group consisting of tertiary amines, organometallic derivatives or salts of bismuth, tin, iron, antimony, cobalt, thorium, aluminum, zinc, nickel, cerium, molybdenum, vanadium, copper, manganese and zirconium, metal carboxylates, metal hydroxides, and phosphines.
9. The flexible polyurethane foam of claim 6, wherein the foam exhibits a compressive strength at 10% to 50% deformation of 0.32 MPa to 0.71 MPa.
10. The flexible polyurethane foam of claim 6, wherein the thermal stability of the foam is represented by an initial decomposition at 299° C.
11. The flexible polyurethane foam of claim 6, wherein the thermal transition behavior of the foam is represented by a glass transition temperature of 30.4° C. to 32.1° C.
12. The flexible polyurethane foam of claim 6, wherein:
  (i) the polyol composition is present in the blend composition in an amount of 100 parts by weight;
  (ii) the ratio of hydroxy groups in the polyol composition to isocyanate groups in the at least one polyisocyanate component is 1:1.2;
  (iii) the at least one blowing agent is present in the blend composition in an amount of 2 parts by weight;
  (iv) the at least one cell stabilizer component is present in the blend composition in an amount of 2 parts by weight; and
  (v) the at least one catalyst component is present in the blend composition in an amount of 0.2 parts by weight.
13. A rigid polyurethane foam prepared from a blend composition comprising:

(i) the polyol composition of claim 1;
(ii) at least one polyisocyanate component, wherein the ratio of hydroxy groups in the polyol component to isocyanate groups in the at least one polyisocyanate component is less than 1;
(iii) at least one blowing agent;
(iv) at least one cell stabilizer component; and
(v) at least one catalyst component.

14. The rigid polyurethane foam of claim 13, wherein the at least one polyisocyanate component comprises the formula R(NCO)$_n$, wherein n is 1 to 10, and wherein R is 2 and 40 carbon atoms, and wherein R contains at least one aliphatic, cyclic, alicyclic, aromatic, branched, aliphatic- and alicyclic-substituted aromatic, or aromatic-substituted aliphatic and alicyclic group.

15. The rigid polyurethane foam of claim 13, wherein:
(i) the blowing agent is selected from the group consisting of water, carbon dioxide, nitrogen gas, chlorofluorocarbons (CFCs), hydrofluorocarbons (HFCs), hydrochlorofluorocarbons (HCFCs), fluoroolefins (FOs), chlorofluoroolefins (CFOs), hydrofluoroolefins (HFOs), hydrochlorfluoroolefins (HCFOs), acetone, and low-boiling hydrocarbons,
(ii) the cell stabilizer component comprises a silicone surfactant or an anionic surfactant, and
(iii) the catalyst component is selected from the group consisting of tertiary amines, organometallic derivatives or salts of bismuth, tin, iron, antimony, cobalt, thorium, aluminum, zinc, nickel, cerium, molybdenum, vanadium, copper, manganese and zirconium, metal carboxylates, metal hydroxides, and phosphines.

16. The rigid polyurethane foam of claim 13, wherein the foam exhibits a compressive strength at 6% to 25% deformation of 0.88 MPa to 2.61 MPa.

17. The rigid polyurethane foam of claim 13, wherein the thermal stability of the foam is represented by an initial decomposition at 299° C.

18. The rigid polyurethane foam of claim 13, wherein:
(i) the polyol composition is present in the blend composition in an amount of 100 parts by weight;
(ii) the ratio of hydroxyl groups in the polyol composition to isocyanate groups in the at least one polyisocyanate component is 1:1.2;
(iii) the at least one blowing agent is present in the blend composition in an amount of 2 parts by weight;
(iv) the at least one cell stabilizer component is present in the blend composition in an amount of 2 parts by weight; and
(v) the at least one catalyst component is present in the blend composition in an amount of 2 parts by weight.

* * * * *